Figure 1:
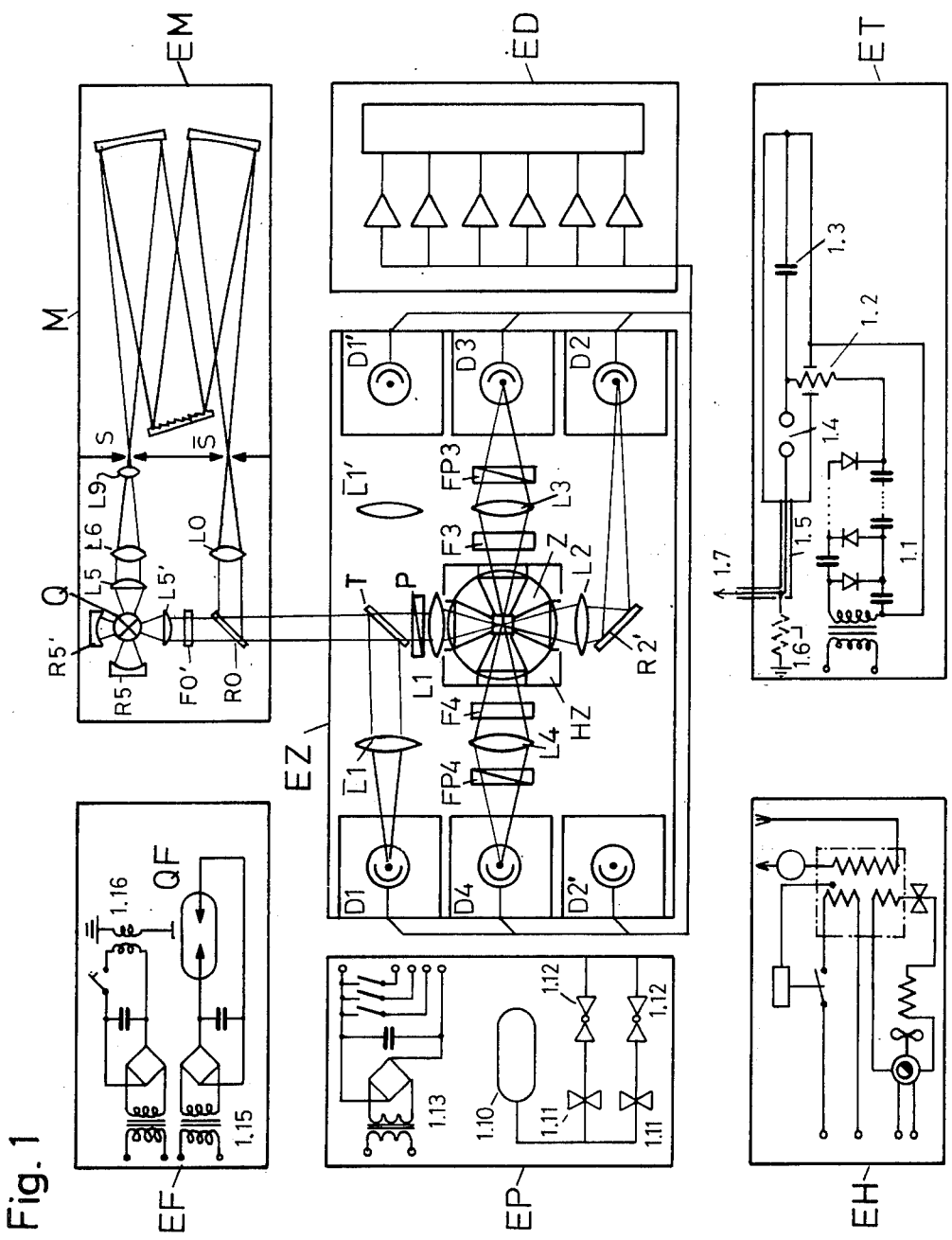

United States Patent [19]

De Maeyer et al.

[11] 4,076,420

[45] Feb. 28, 1978

[54] APPARATUS FOR INVESTIGATING FAST CHEMICAL REACTIONS BY OPTICAL DETECTION

[75] Inventors: Leo C. M. De Maeyer; Carl-Roland Rabl, both of Gottingen; Thomas M. Jovin, Schloss Berlepsch; Detlev Riesner, Hannover, all of Germany; Rudolf Rigler, Stockholm-Danderyd, Sweden; Lutz Bodo Veil, Gottingen, Germany; Hans Lehrach, Vienna, Austria

[73] Assignee: Max-Planck-Gesellschaft zur Forderung der Wissenschaften e.V., Gottingen, Germany

[21] Appl. No.: 498,816

[22] Filed: Aug. 19, 1974

[30] Foreign Application Priority Data

Feb. 22, 1974 Germany .............................. 2408646

[51] Int. Cl.² ...................... G01N 21/00; G01N 1/10; G01J 3/30
[52] U.S. Cl. .................................. 356/73; 23/253 R; 356/85; 356/86; 356/96; 356/103; 356/114; 356/246

[58] Field of Search ....................... 356/72, 73, 75, 85, 356/86, 87, 96, 244, 246, 103, 114; 23/253 R

[56] References Cited

U.S. PATENT DOCUMENTS

| 3,558,232 | 1/1971 | MacCosham | 356/244 |
| 3,751,171 | 8/1973 | Hughes, Jr. et al. | 356/244 |
| 3,806,259 | 4/1974 | Boostrom et al. | 356/244 |

Primary Examiner—Vincent P. McGraw
Attorney, Agent, or Firm—Flynn & Frishauf

[57] ABSTRACT

A reaction kinetics measuring system which provides for the application of a great variety of reaction initiating methods, as temperature or pressure or electrical field jump methods, mixing methods, flash photolysis method, and combinations of said methods, and for various optical detection methods, as absorption or fluorescence or scattered light or polarized light detection methods. The system features quickly and easily interchangeable optical elements in a number of optical paths, and a multitude of selectively usable measuring cells to adapt the system to the reaction initiating and detection methods used so that reliable and exactly reproducible results are obtained, which are comparable even if obtained under widely differing conditions.

101 Claims, 79 Drawing Figures

Fig. 7
Fig. 5c
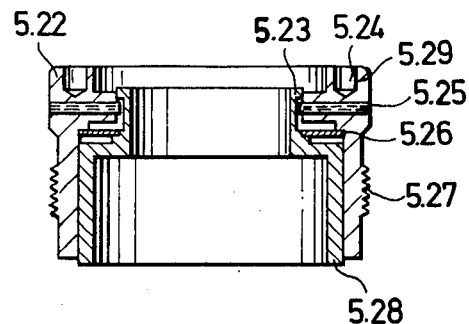
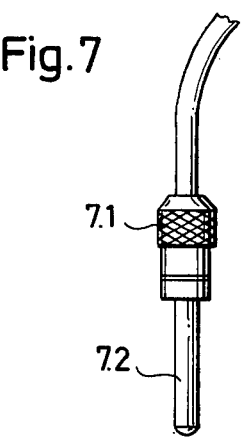
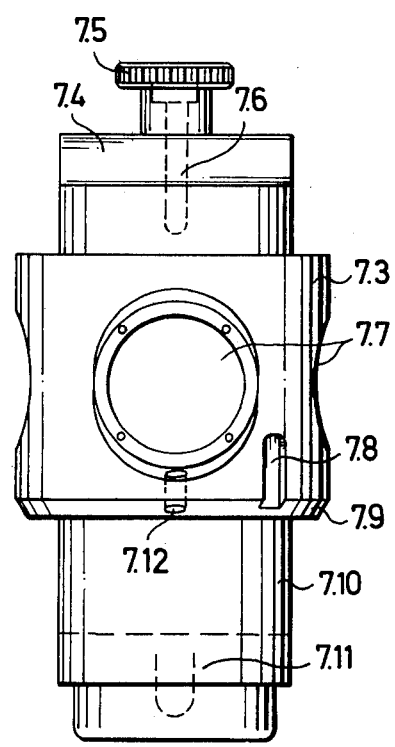
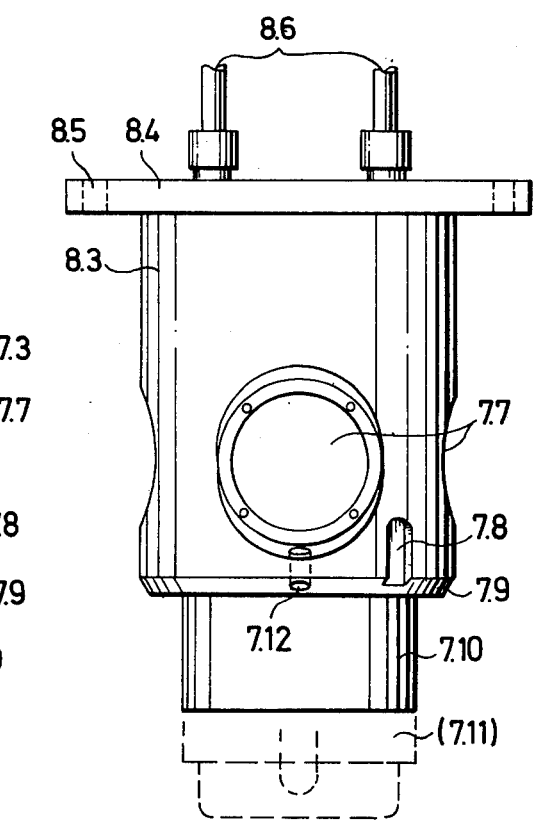
Fig. 8

PRA

PRB

PRC

PRD

Fig. 19.A)
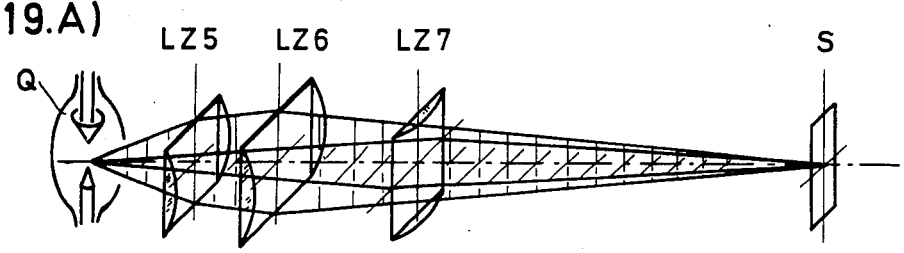
B)
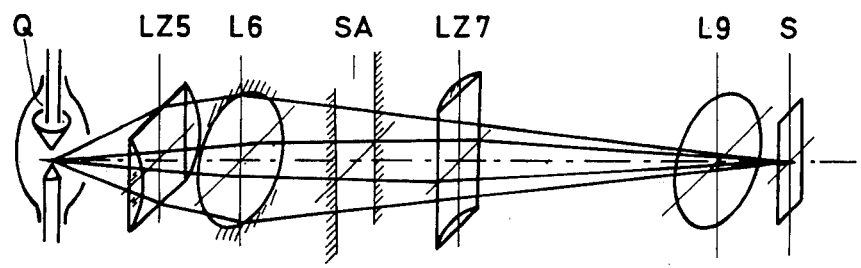
C)
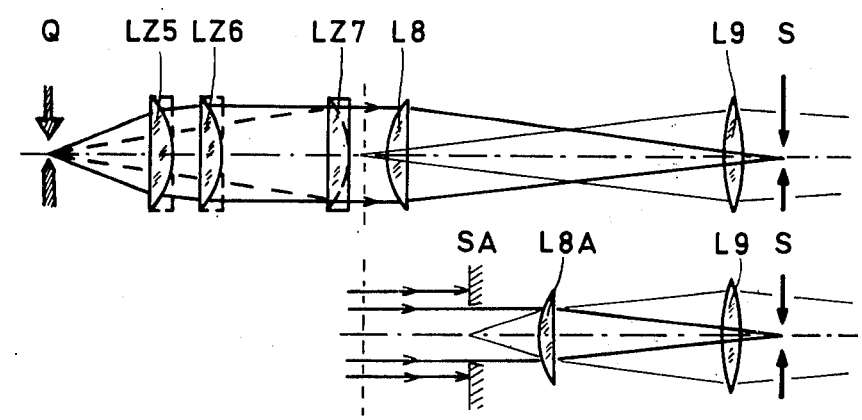
D)
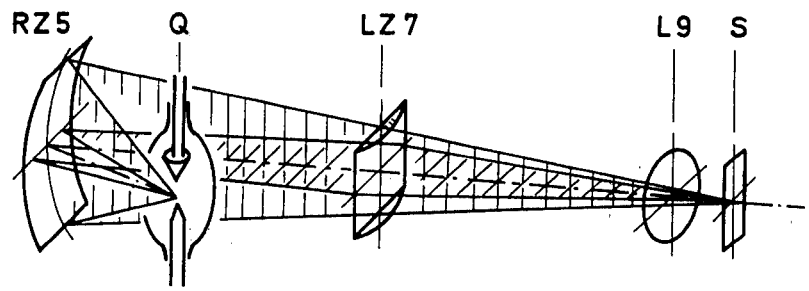

Fig. 22B
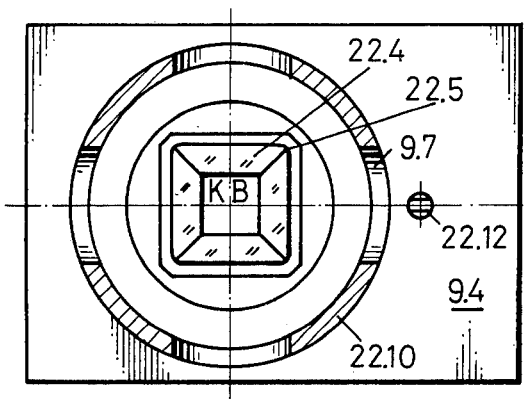
Fig. 22A    Fig. 22C
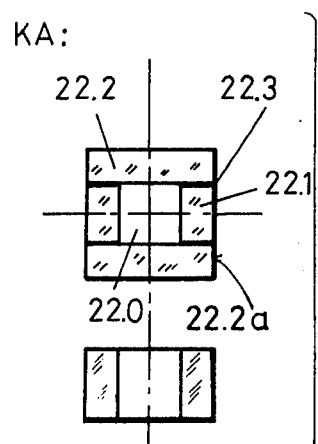
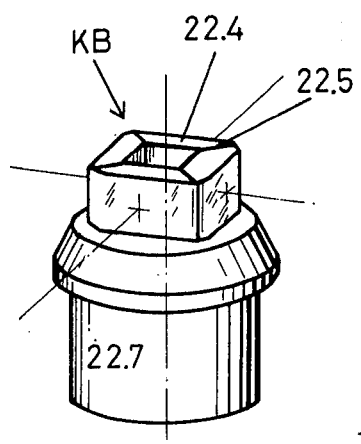
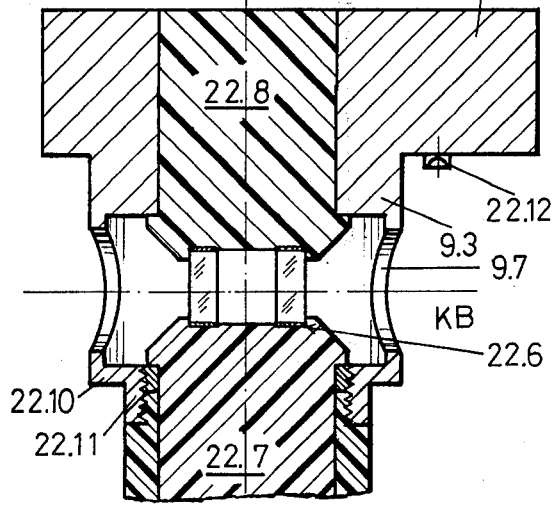

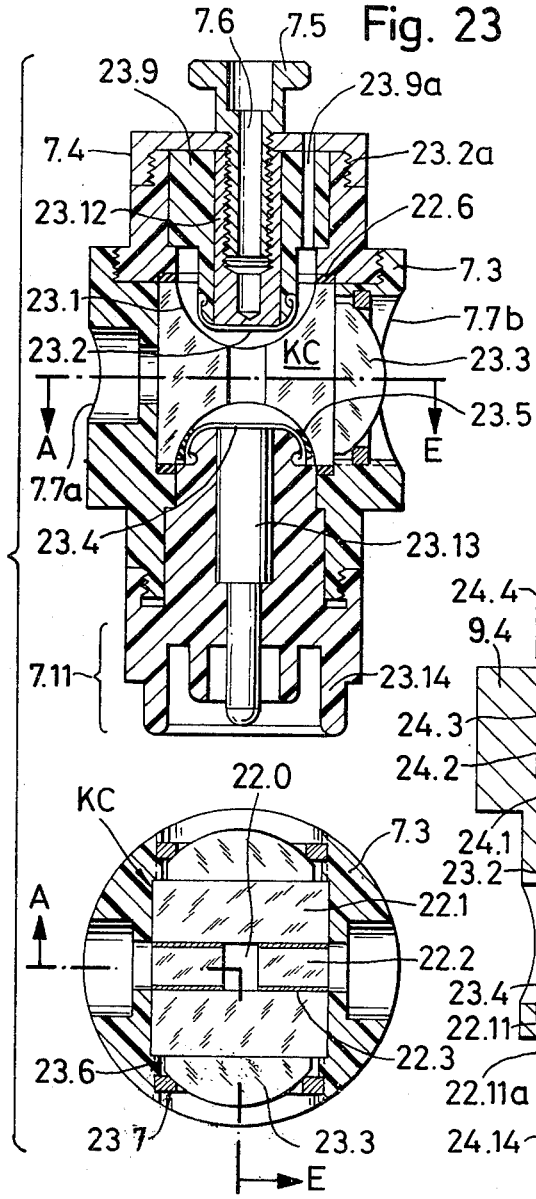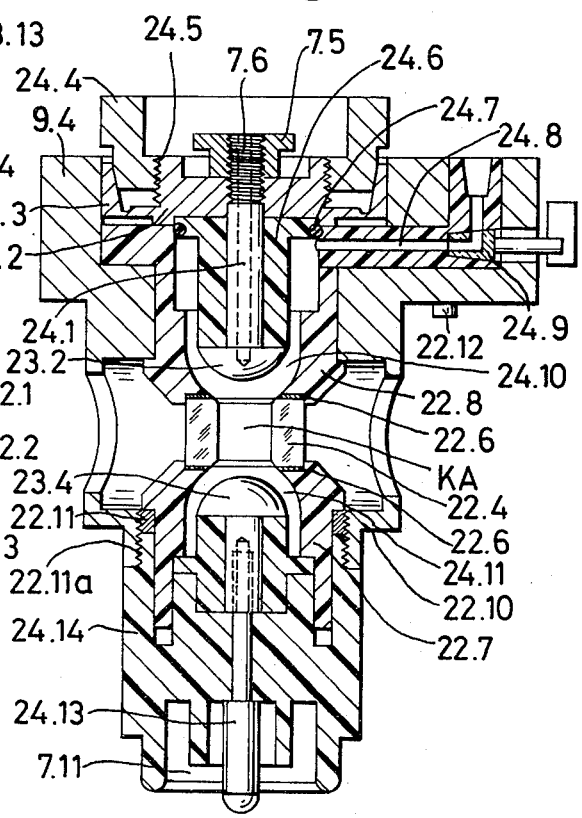

Fig. 26
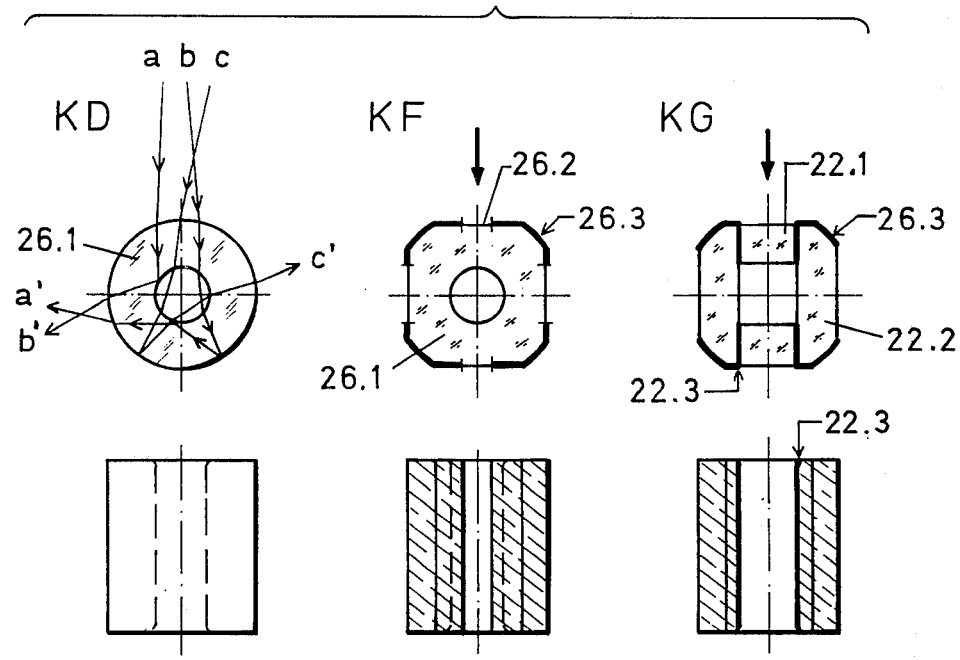
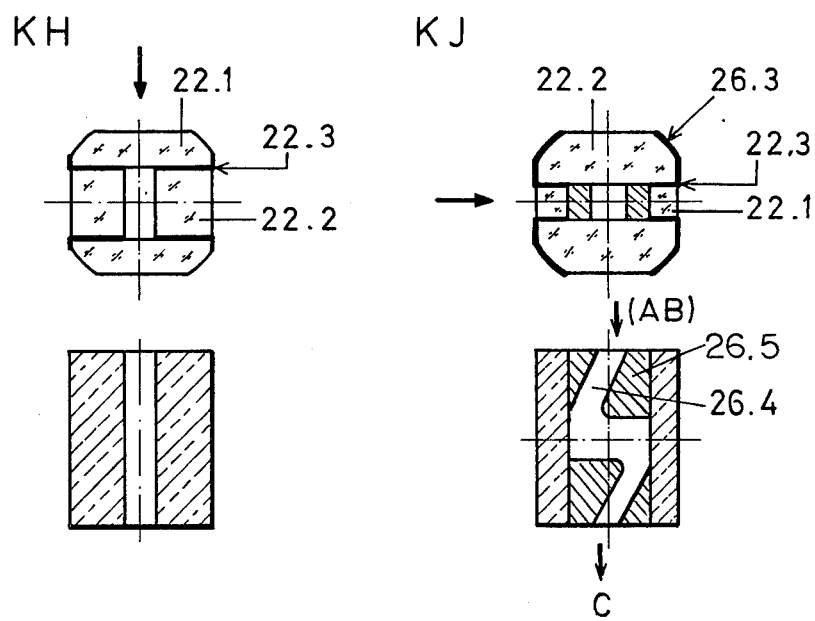

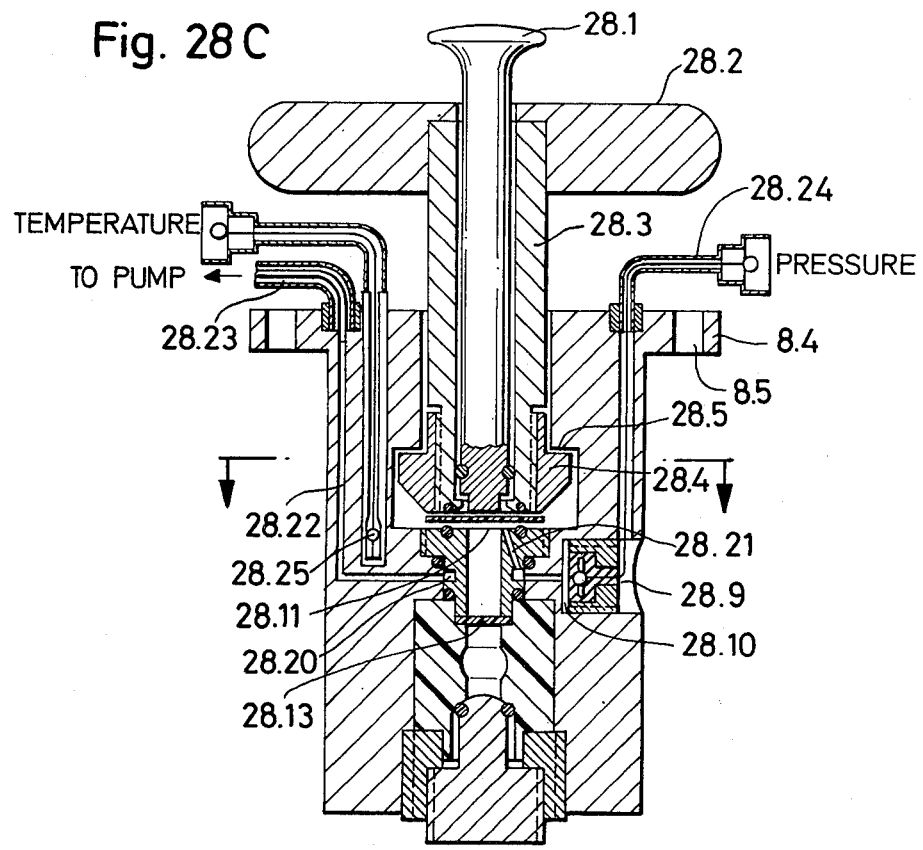
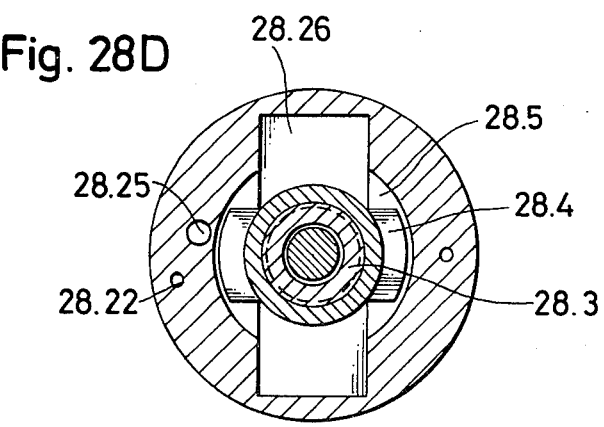

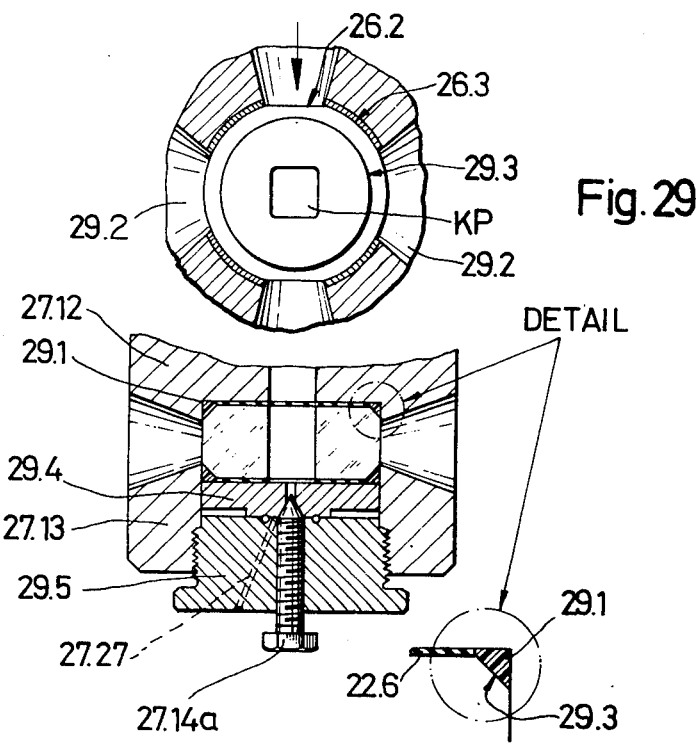
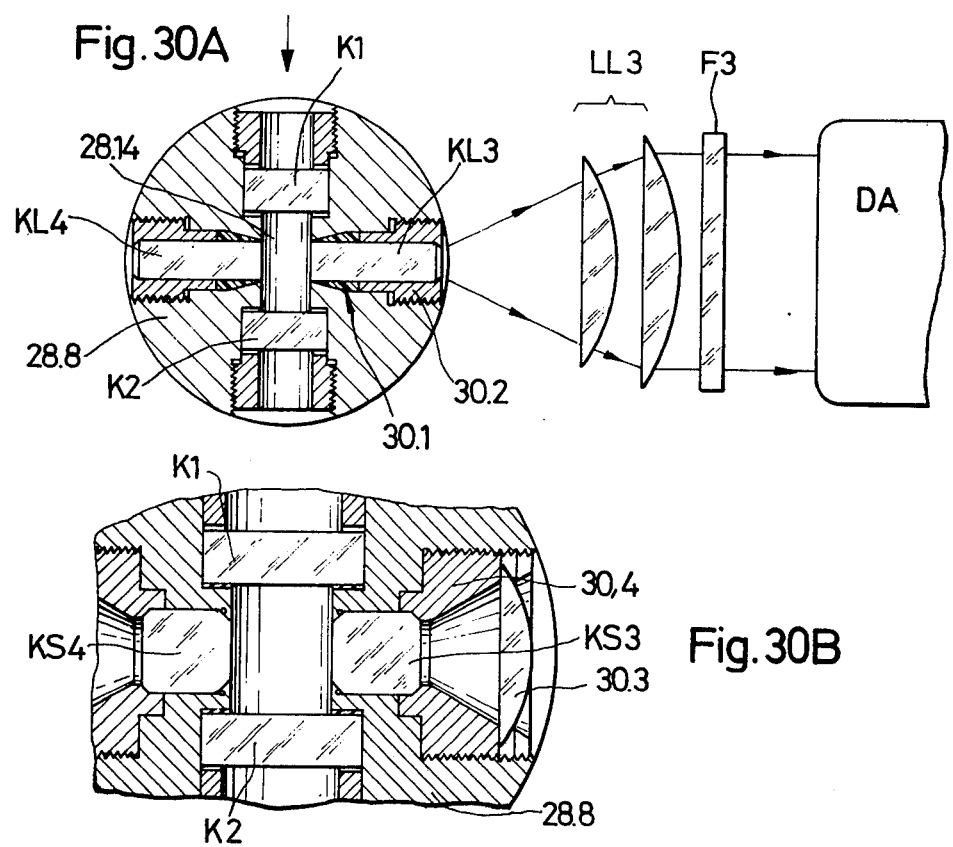

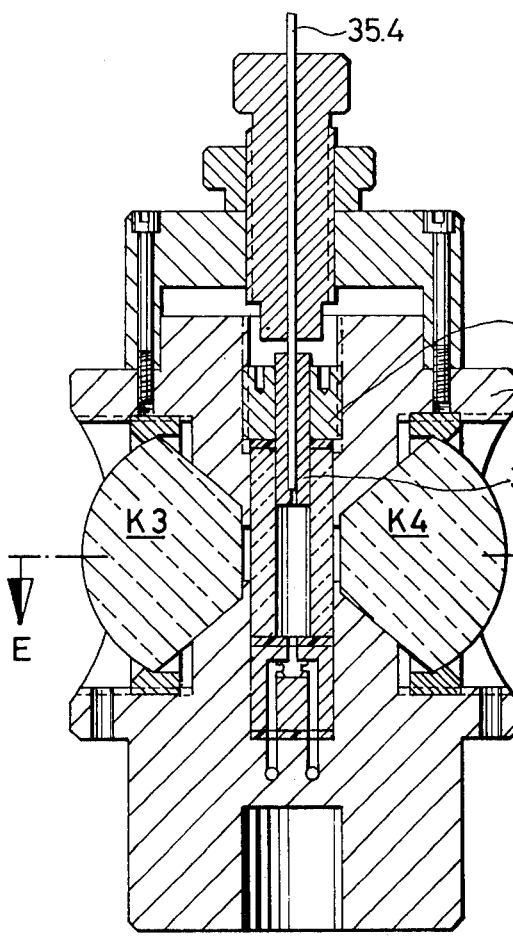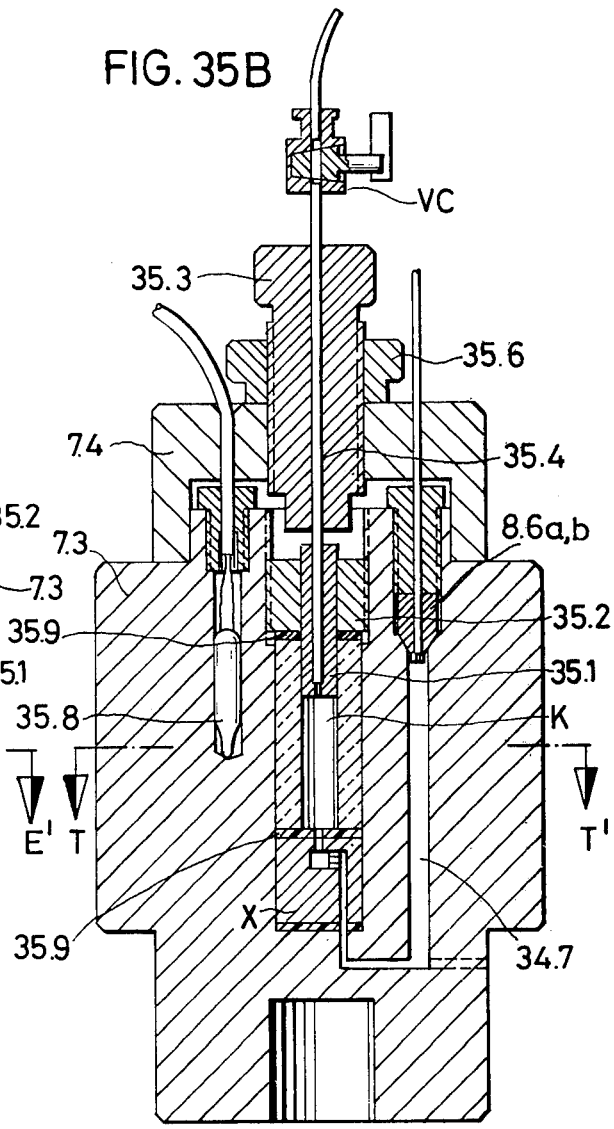

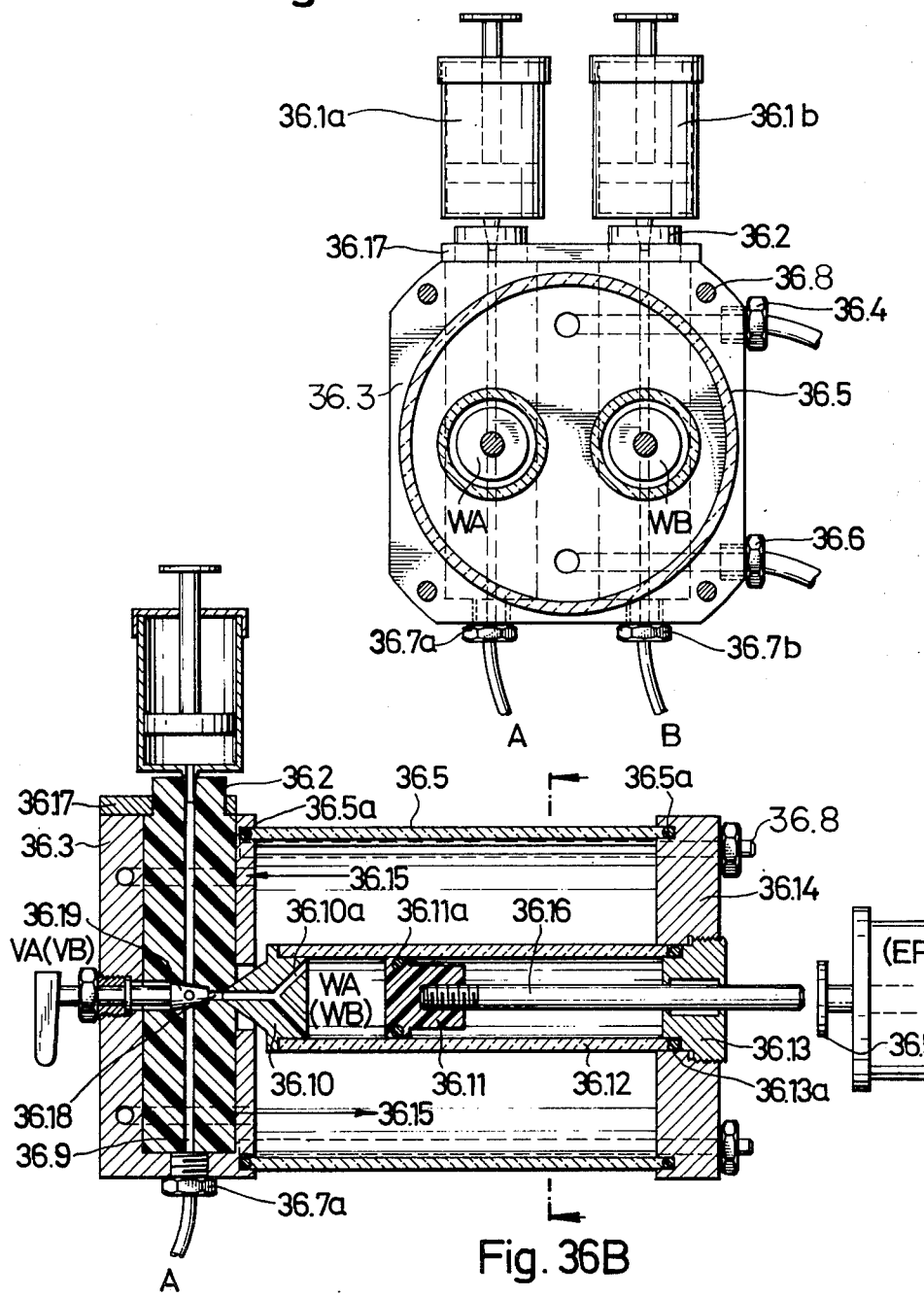

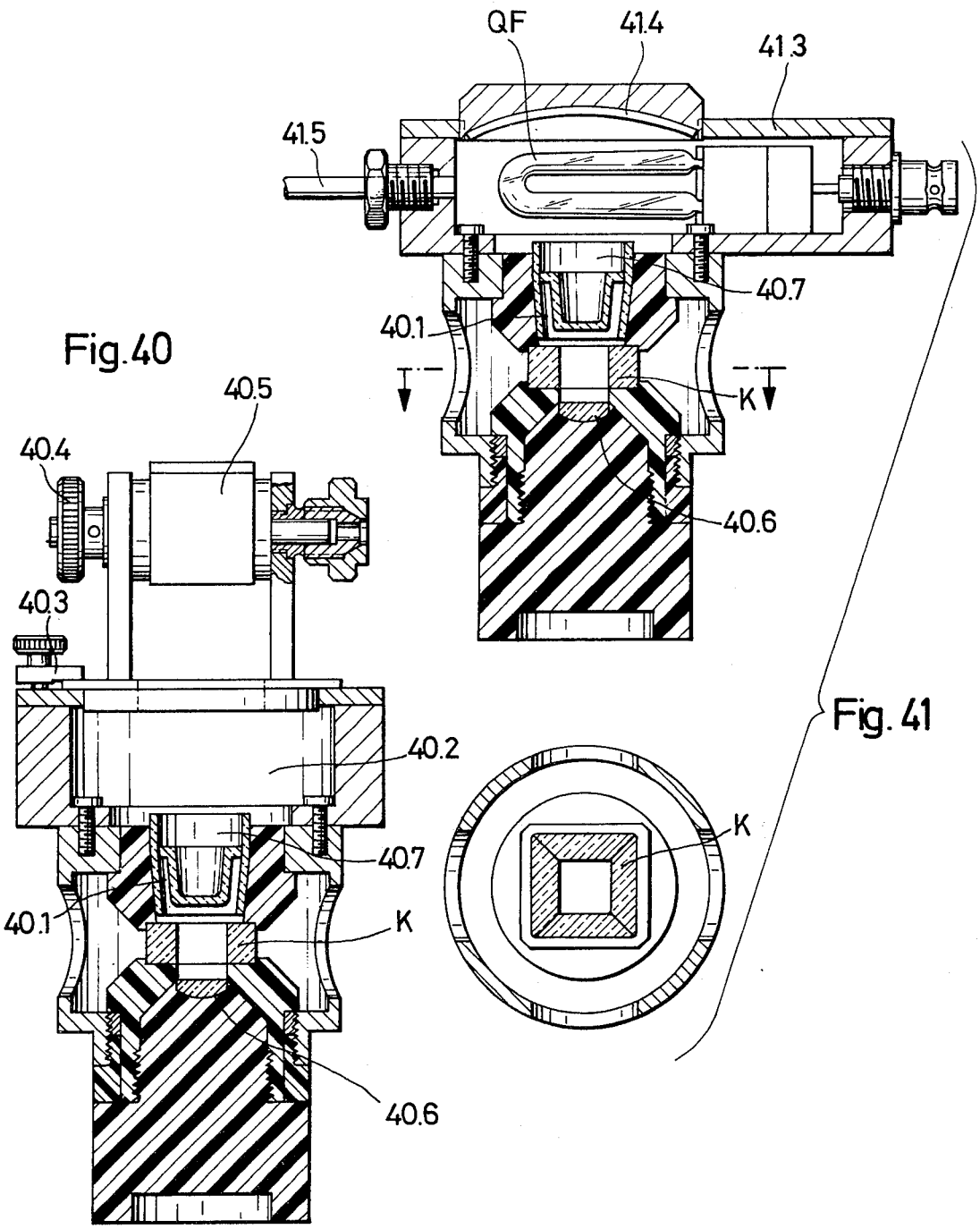

APPARATUS FOR INVESTIGATING FAST CHEMICAL REACTIONS BY OPTICAL DETECTION

BACKGROUND OF THE INVENTION

The present invention relates to an apparatus for investigating the kinetics of fast chemical reactions in solution using relaxation and/or mixing methods with spectrophotometric observation of the time course of reaction.

Various measuring techniques are known for these investigations. They are based on the direct observation of the equilibrium following an initial non-equilibration process state of a chemical system. This initial state can either be established by mixing several reactants (rapid mixing, especially stopped-flow techniques) or by external perturbation of a previously existing equilibrium state ("relaxation techniques").

The article *Rev. Sci. Instr.* 22, 619 (1951) describes a mixing technique in which the reactants are quickly mixed in a chamber containing a number of mixing jets. The mixture then flows into a "flow"-tube through which a light beam passes. The light intensity behind the flow-tube is a measure of the concentration of the reaction product, and is recorded as a function from the distance of the mixing chamber, which gives the elapsed time of reaction (continuous flow method). In another flow technique the reacting mixture is stopped within a few milliseconds by a movable piston which has a stop position. After the flow is stopped, the time course of reaction is measured by the absorption of visible or ultraviolet light, or other optical parameters (stopped-flow method: J. Physiology 117, 49 P (1952)).

In contrast to flow techniques, relaxation techniques start from the equilibrium state of the chemical system. A non-equilibrium state which deviates only by a small extent from the former equilibrium state is produced by a sudden change of temperature, pressure, or electric field strength. Use of these methods offers the advantages of a considerably smaller amount of substance, a higher time resolution and an easier mathematical analysis of the results. These methods are characterized as temperature-, pressure-, and field-jump techniques, depending on the kind of perturbation applied. The initial non-equilibrium state can also be achieved by electromagnetic irradiation, especially with high intensity light (flashlight photolysis). A general survey of the various techniques used for studying fast reactions will be found in *Techniques of Chemistry*, Vol. VI, Part II, ed. G. G. Hammes, Wiley-Interscience, 3rd edition (1974).

In case of the temperature-jump methods the sudden temperature increase is usually produced by discharging a high voltage capacitor. The discharge current passes through the electrically conducting test substance via a spark gap and two metal electrodes which are in electric contact with the test substance. Within a few microseconds or less it is possible to achieve temperature changes of several degrees centigrade. Another method used is to quickly heat the test substance by irradiating it with a microwave or a giant laser pulse. For measurements in the long-time range of 10secs or more, fast switching or liquid thermostatting of the sample cell has been used (*Europ. J. Biochem.* 4, 373 (1969)).

A review of the arrangements used for temperature-jump methods is given in the paper of A. Yapel and R. Lumry "A Practical Guide to the Temperature-Jump Method for Measuring the Rate of Fast Reactions", published in *Methods of Biochemical Analysis*, ed. D. Glick, Vol. 20, p. 169–350, Interscience N.Y. For studying intermediate, e.g. in enzyme reactions, a combination of the rapid mixing and the temperature-jump method can be used, e.g. as described in *Rev. Sci. Inst.* 37, 746 (1966).

Pressure-jump methods use an autoclave cell chamber or, for measurements in the $\mu$sec-range, a shock-tube arrangement. The fast pressure change is usually produced by suddenly bursting a metal disk. (W. Knoche in *Techniques of Chemistry*, loc. cit.)

In the case of electric field-jump methods the non-equilibrium state is produced by suddenly applying a high electric field. This results in a dissociation of weak electrolytes. (L. De Maeyer in *Methods in Enzymology*, vol. 16, eds. Kustin, Colowick, and Kaplan, Academic Press (1969); L. De Maeyer and A. Persoons in *Techniques of Chemistry*, loc. cit.)

Optical methods are usually used for observing temperature-jump and field-jump techniques. For pressure-jump techniques conductivity changes are mostly measured, but optical absorption can also be used *Analyt. Biochemistry* 28, 273 (1969).)

For producing a non-equilibrium state by radiant energy the side of a transparent reaction vessel is exposed to radiation from the short, powerful gas discharge of a flashlamp. A continuous or pulsed probing light beam passes the axis of the vessel. A pulse laser can also be used instead of the flashlamp. A review of photochemical flashlight devices is given by G. Porter and M. A. West in *Techniques of Chemistry*, loc. cit.

For a review of apparatus with special reference to commercial set-ups see also: Z. A. Schelly and E. M. Eyring in *Journal of Chemical Education*, 48, A 639 and A 695 (1971).

The existing techniques are based on the combination of a specific perturbation method with a specific observation method. Consequently, measurements using the temperature-jump, pressure-jump, field-jump, flashlight- and flow-techniques always required a specially designed apparatus. Changing the parameter of observation (absorption, fluorescence of polarimetric methods) involved at least troublesome modifications and readjustments of the apparatus. Performance of experiments with various physical parameters of perturbation and observation was therefore largely restricted, especially comparative measurements using various parameters.

The need for designing special apparatus was very common in order to obtain maximal sensitivity (which is generally required in research problems). To illustrate this point apparatus for combined flow-temperature jump measurements should be mentioned. If such an apparatus is derived from a satisfactory flow apparatus satisfactory temperature-jump measurements cannot be obtained, and vice versa. On the one hand, the concentration changes involved in temperature-jump measurements are considerably smaller than those in flow-measurements. They are often less than 1% and their time course has to be determined quantitatively in periods which are up to 1000 times shorter. As a consequence, the signal-to-noise-ratio should improve but it deteriorates at short time periods because of the too low light intensity. On the other hand, highly spcialized temperature-jump apparatus are very sensitive to mechanical vibrations which occur in flow experiments. Therefore, they show troublesome instabilities of the light flux if used for combined flow-temperature jump measurements. An apparatus optimized for the combined measurements, however, does never give the same sensitivity as a pure temperature-jump or a pure stopped-flow apparatus when used for uncombined measurements. Thus the number of apparatus needed for optimized work is still increased.

OBJECT AND SUMMARY OF THE INVENTION:

It is therefore an object of the invention to construct an apparatus for investigating fast chemical reactions by optical detection, wherein measurements can be performed with various parameters of perturbation - temperature-jump, field-jump, pressure-jump, flash-photolysis, rapid mixing, and combinations thereof, and also with various parameters of optical observation of the time course of reaction - absorption, fluorescence, scattered light, parameters of polarization, namely fluorescence polaization, also with special attention to the various time ranges of reactions. It is further an object of the invention to perform investigations of many different types with the same chemical system under reproducible and accurately comparable conditions, and with small sample volumes. The new apparatus comprises at least one light path (light source, monochromator, and imaging means), means for supporting a sample cell in this light path, wherein the sample cell forms a chamber for holding a liquid sample of the investigated chemical system, at least one photodetector, and means for performing an external perturbation according to the relaxation and/or the rapid mixing method. According to the invention, the new apparatus provides a thermostattable sample cell holder which permits easy interchange and thermostatting of sample cells, a set of sample cells which have similar exterior shape but are specially designed for the application of various sample volumes, various parameters of optical observation of the time course of reaction (absorption, fluorescence, scattered light, parameters of polarization), and various parameters of perturbation (temperature-jump, field-jump, pressure-jump, flash-photolysis, rapid mixing, or combinations thereof), and easily interchangeable or variable optical means for adaptation of the measuring light path to the dimensions of the cell chamber of the respective sample cell, to the parameter of optical observation, and to the time range of observation.

The invention will be described by way of example with reference to the accompanying drawings, wherein:

Fig. 1: Basic design of the new apparatus with excitation units

Figure 2:
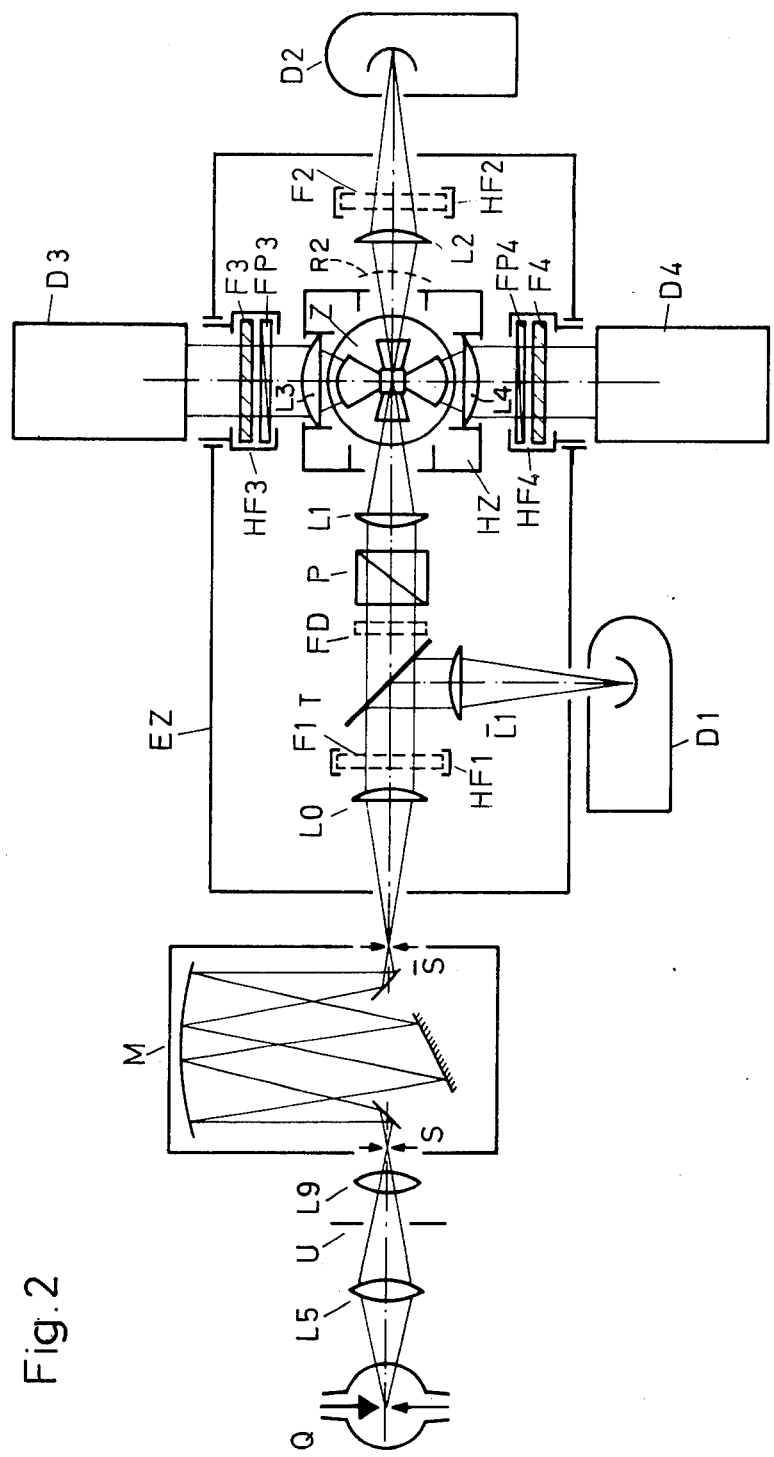

FIG. 2: Example of the optical arrangement of the apparatus

Figure 3:
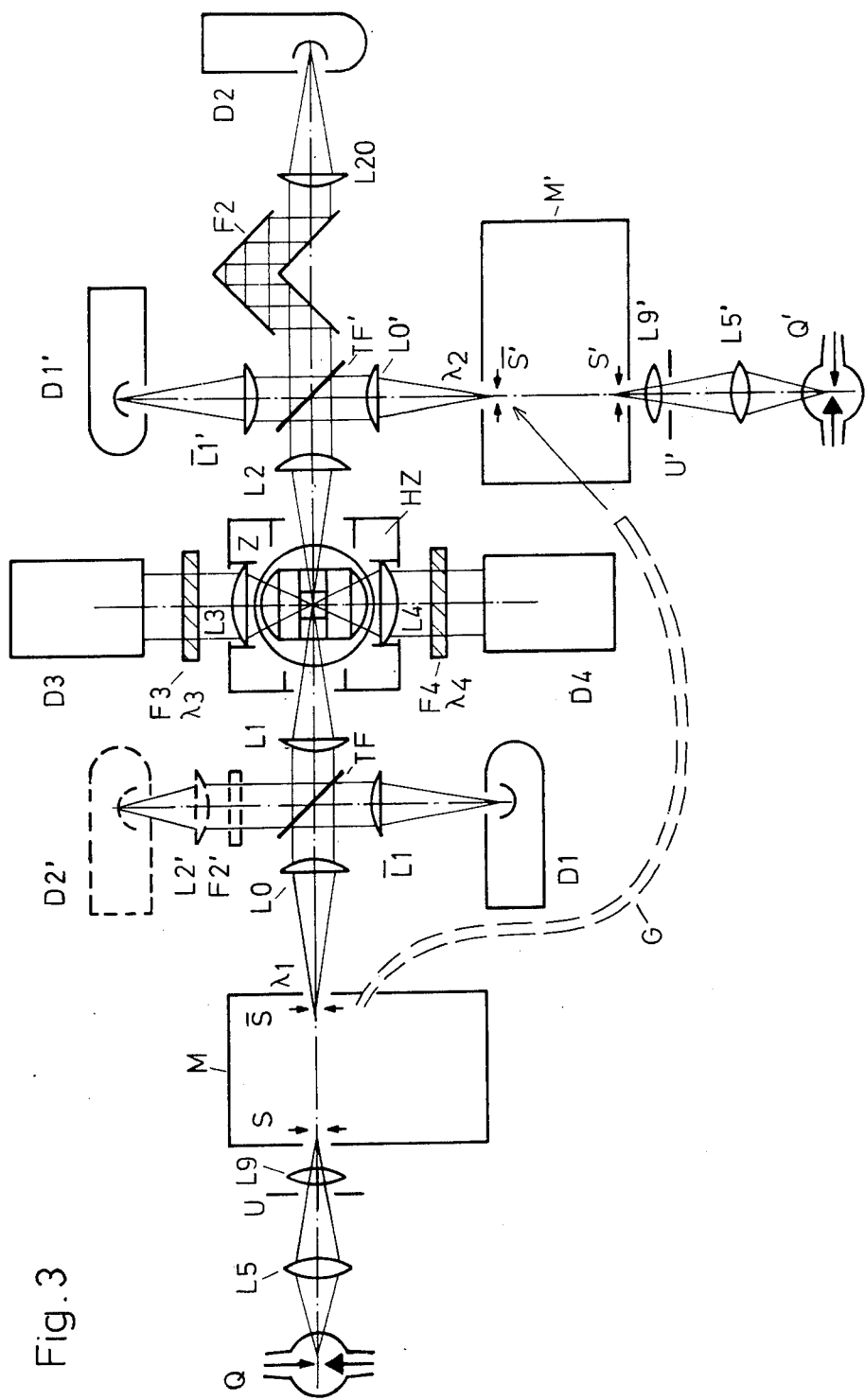

FIG. 3: Modified optical arrangement of the apparatus

Figure 4:
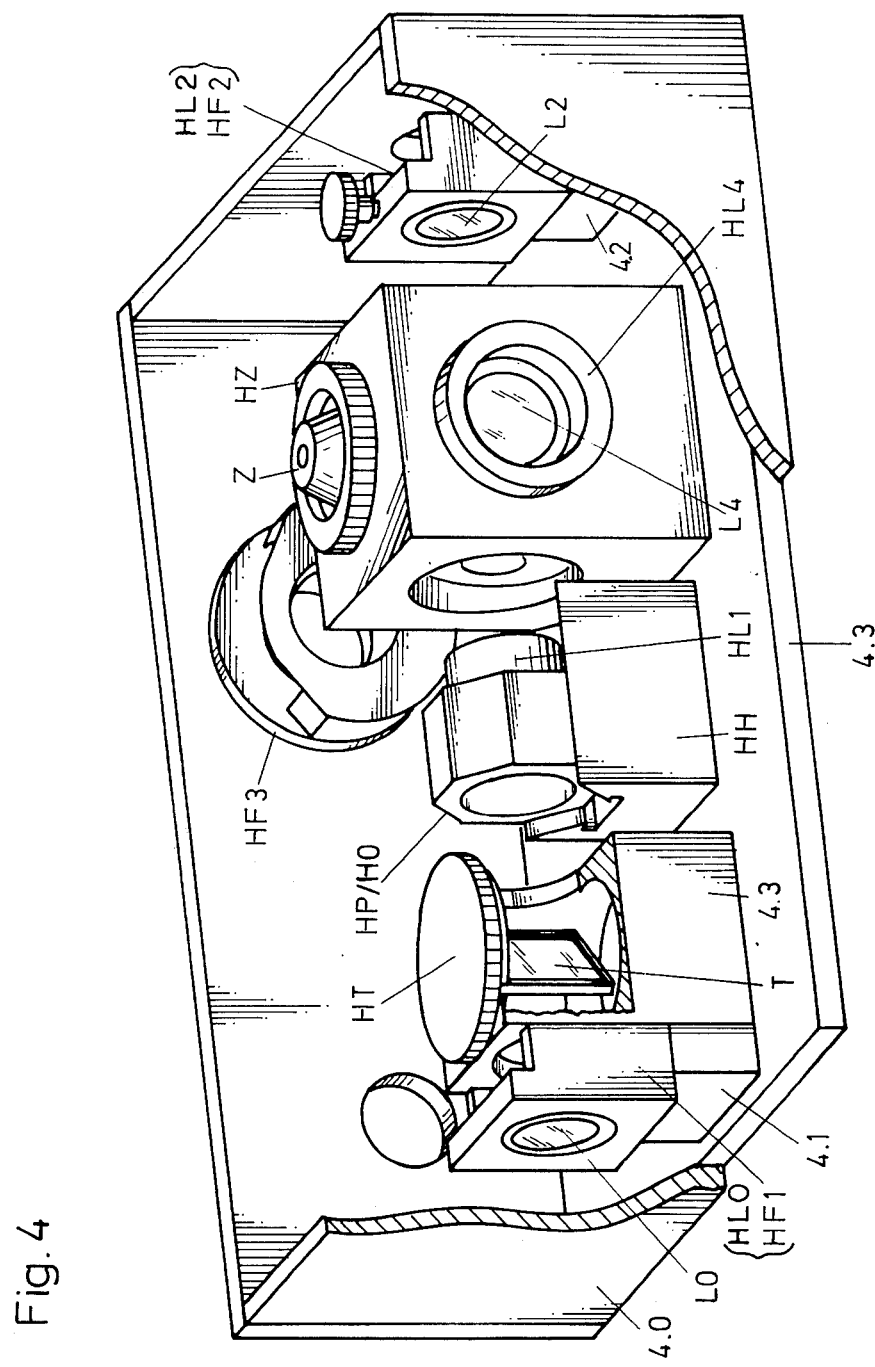

FIG. 4: Example of sample cell unit EZ in FIG. 2

Figure 5A:
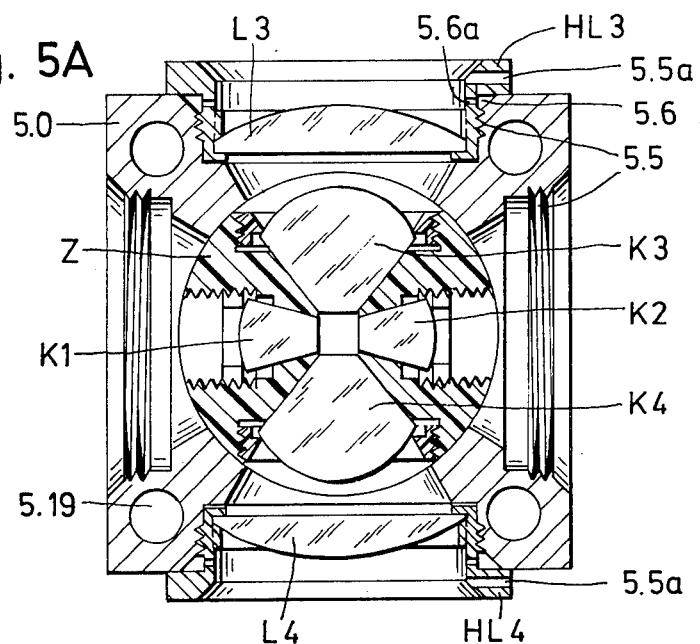

FIGS. 5A and B: Horizontal and vertical cross sections of the sample cell holder HZ for the version according to FIG. 4

Figure 5B:
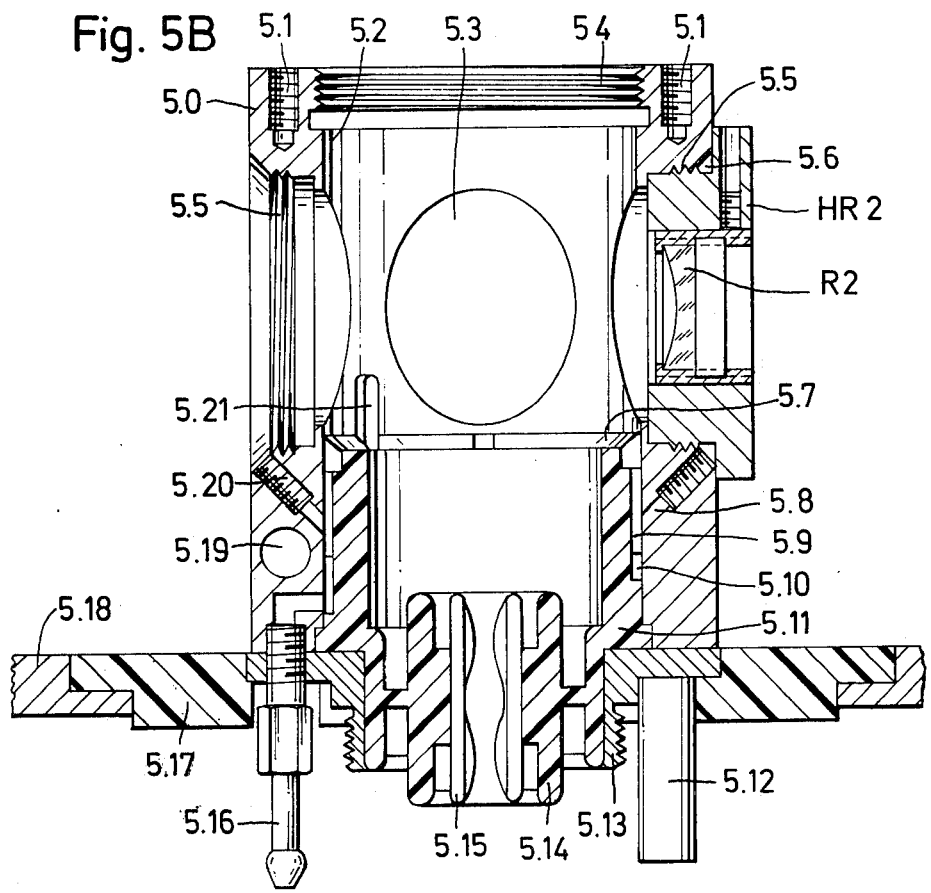

FIG. 5C: Mounting ring for sample cell holder as shown in FIGS. 5 A and B

Figure 6:
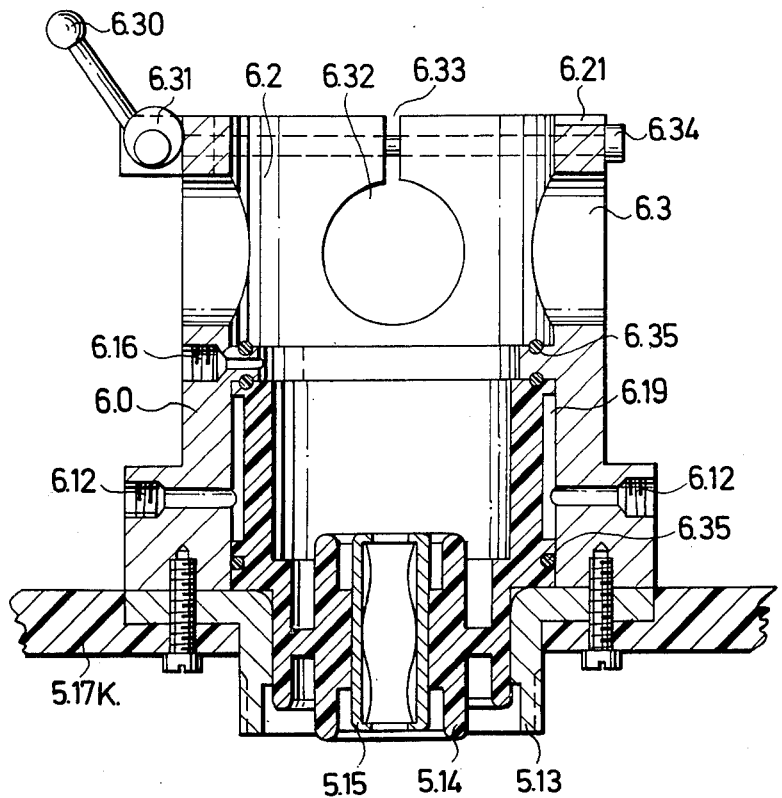

FIG. 6: Vertical cross section of a modified sample cell holder

FIG. 7: Outer shape of a sample cell, model A, with temperature sensor

FIG. 8: Outer shape of a sample cell, model B

Figure 9:
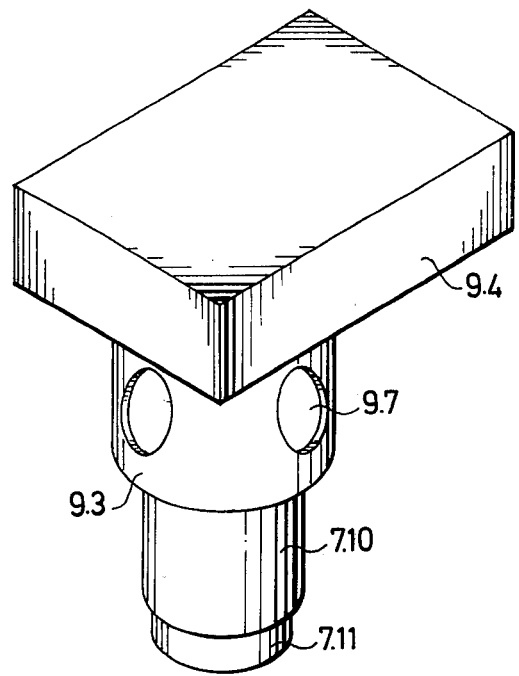

FIG. 9: Outer shape of a sample cell, model C

FIG. 10: Adaptor for spectrophotometer cells designed as a sample changer

FIG. 11: Adaptor for spectrophotometer cells with a reference position

Figure 14:
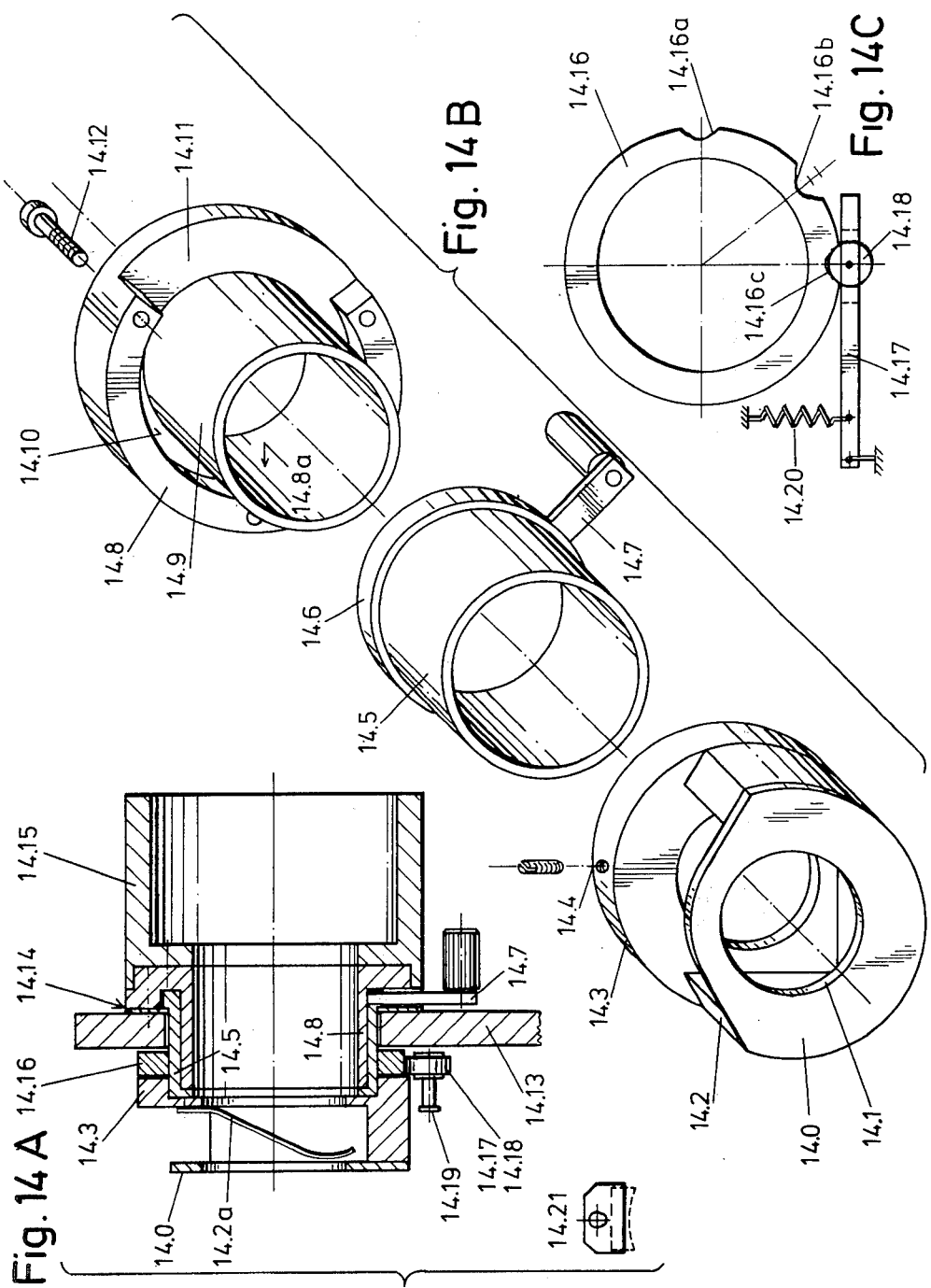
Figure 15:
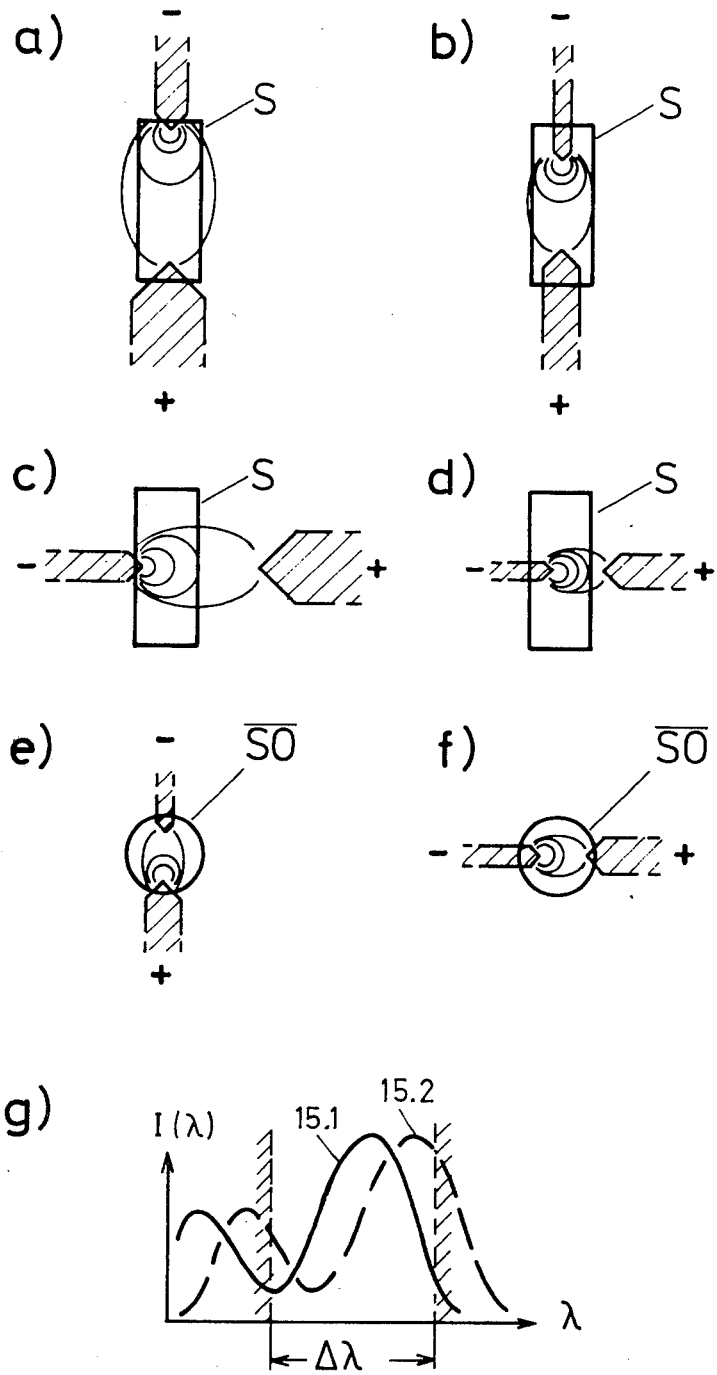
Figure 16:
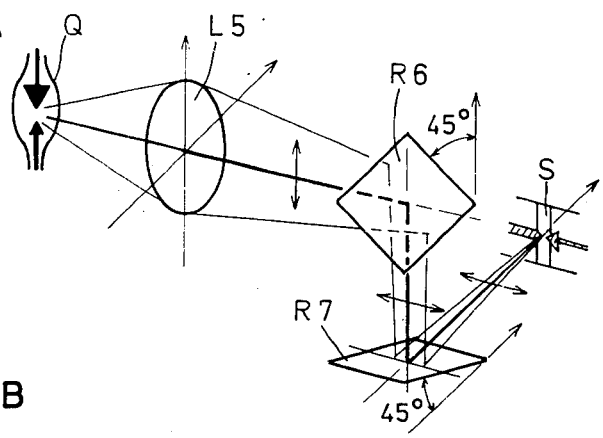
Figure 16:
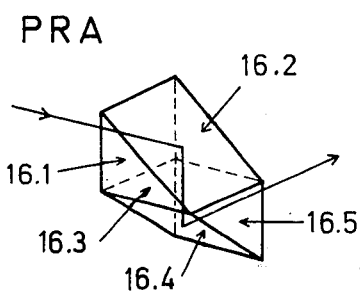
Figure 16:
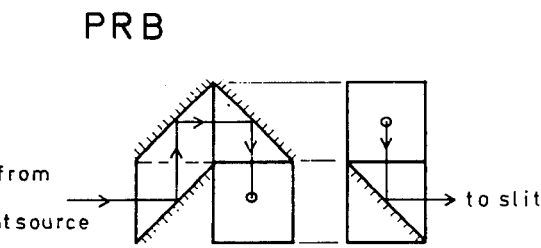
Figure 17:
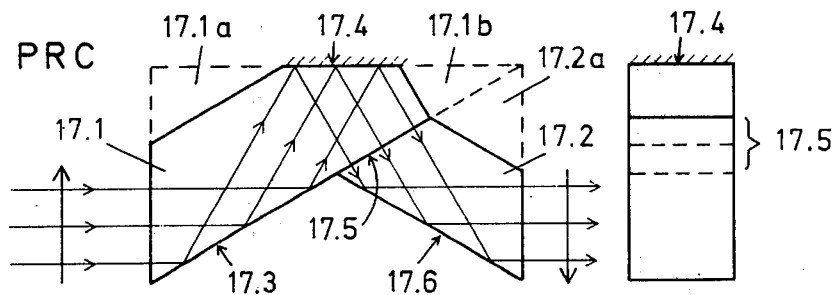
Figure 17:
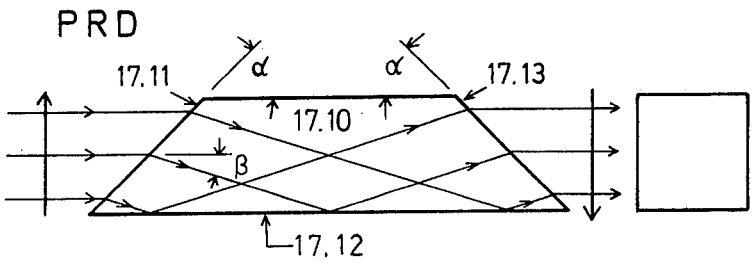
Figure 18:
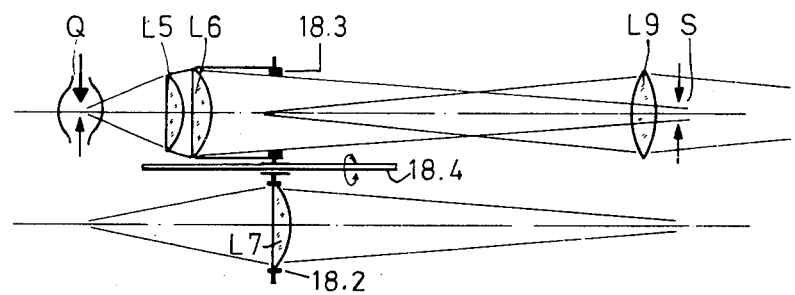
Figure 18:
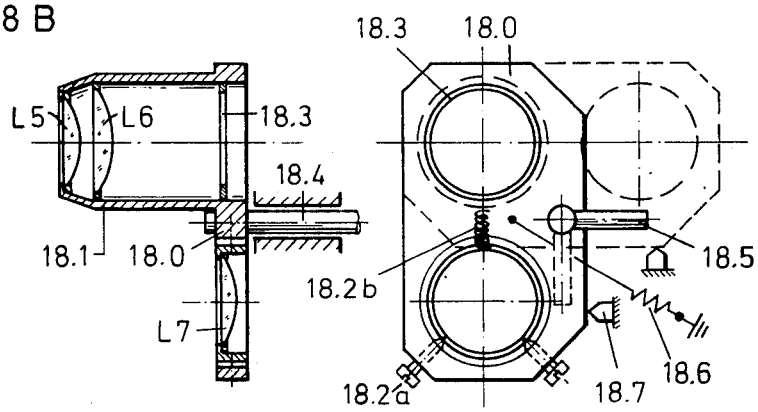
Figure 18:
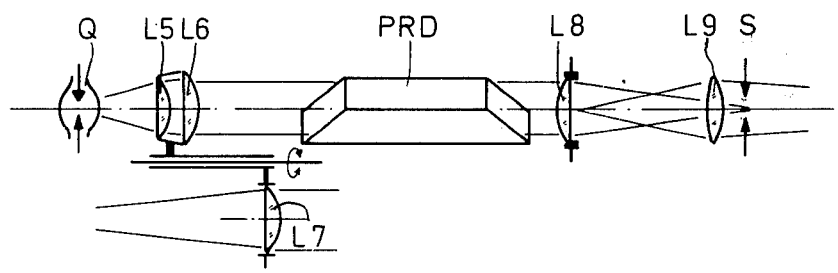
Figure 18:
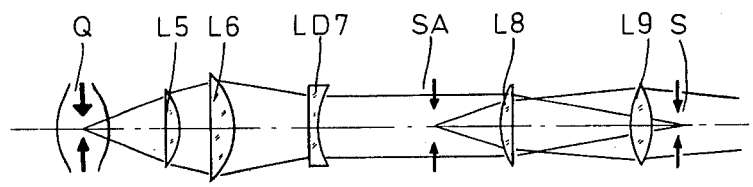

FIG. 12: Variable optical element and corresponding holder in the light path in front of the sample cell FIG. 13: Rotary mounting for a polarizing prism in the primary light path FIG. 14: Rotary filter holder for analyzer filter in the secondary light path FIG. 15: Representation of the image of the light source on the monochromator entrance slit, in various orientation and with various image magnifications FIG. 16: Arrangements for rotating the image of the light source in a deflected light path FIG. 17: Arrangements for rotating the image of the light source in a straight light path FIG. 18: Lamp condenser arrangements for changing the image ratio of the light source, also combined with an arrangement according to FIG. 17 B.

FIG. 19: Alternative lamp condenser arrangements for stabilizing the light flux

Figure 20:
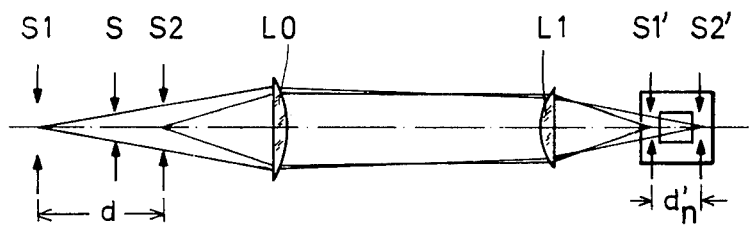
Figure 20:
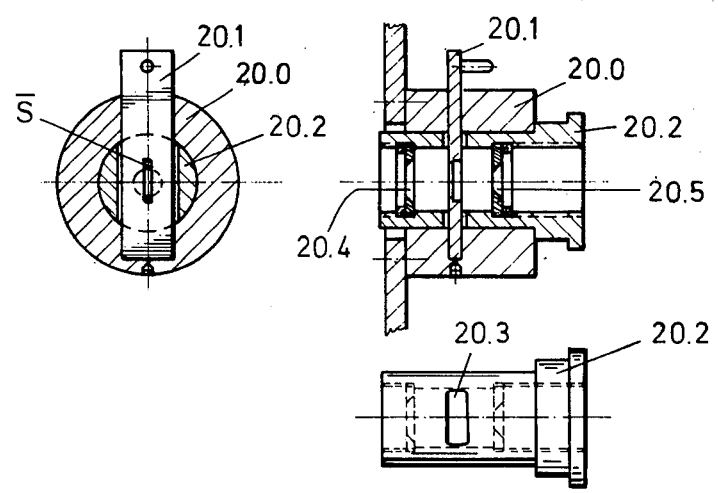
Figure 21:
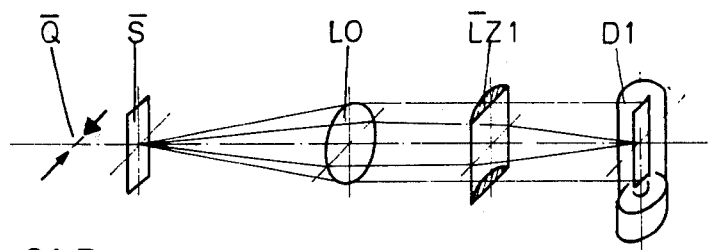
Figure 21:
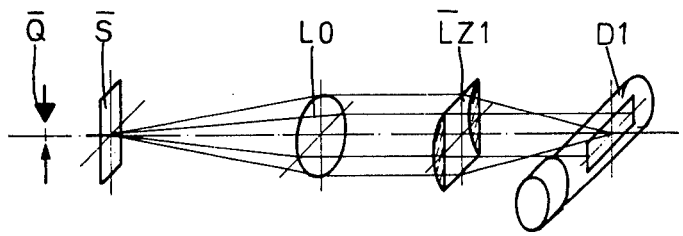

FIG. 20: Arrangement of radiant field diaphragms on both sides of the monochromator exit slit FIG. 21: Arrangements for illumination of the photocathode of a photomultiplier with a rectangular inner cathode FIG. 22: Universal cell chamber for standard cells FIG. 23: Temperature-jump cell with large aperture in the secondary light path FIG. 24: Temperature- and field-jump cell with airtight sealing and connections for admission of protective gas FIG. 25: Temperature-jump microcell FIG. 26: Various cell chambers for microcells FIG. 27: Pressure-jump cell FIG. 28: Modified pressure-jump cell FIGS. 29 and 30: Modified cell chambers, especially for the cells of FIGS. 27 and 28

Figure 31A:
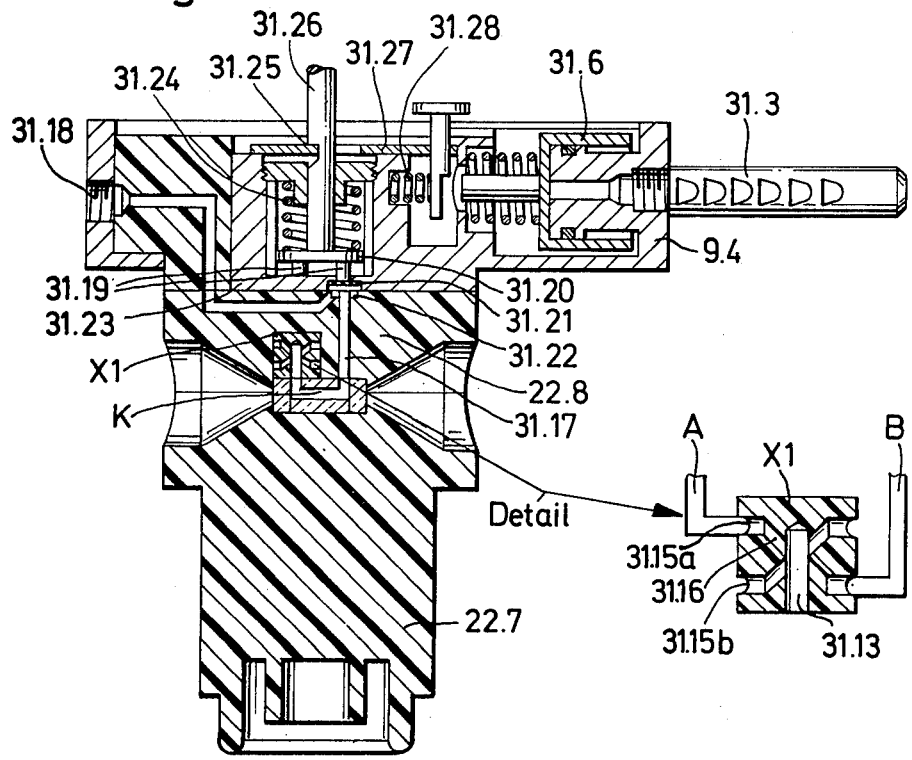
Figure 31B:
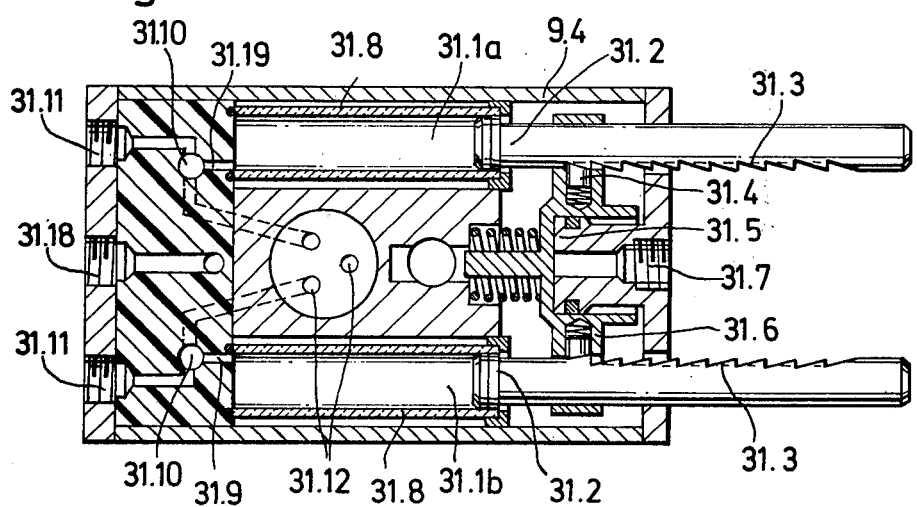
Figure 32A:
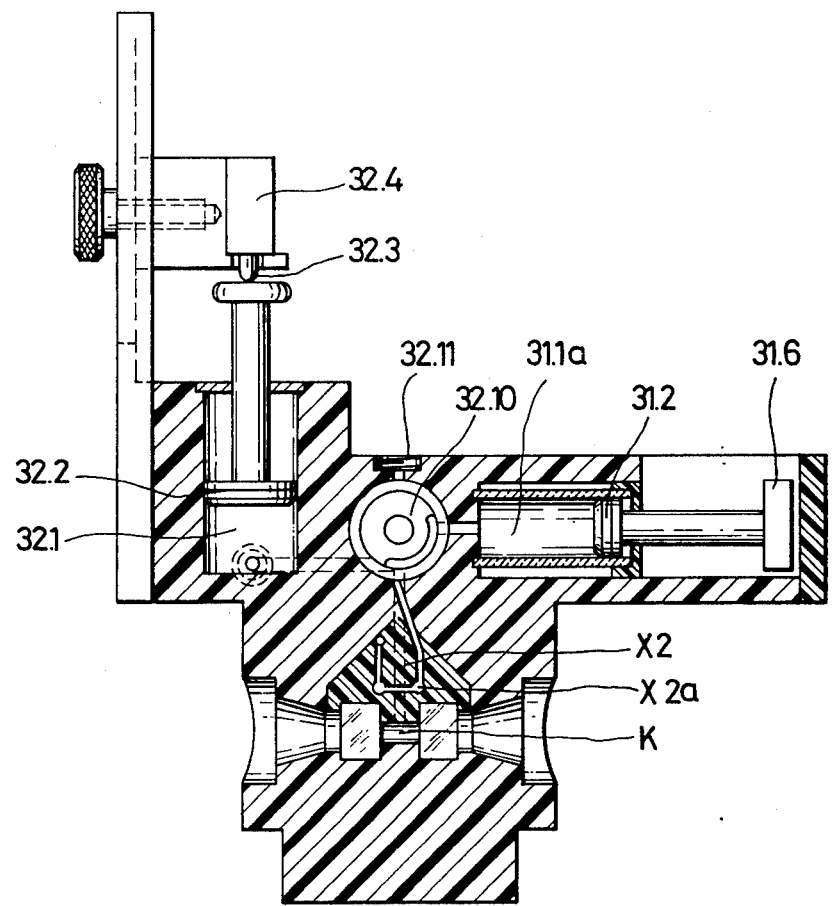
Figure 32C:
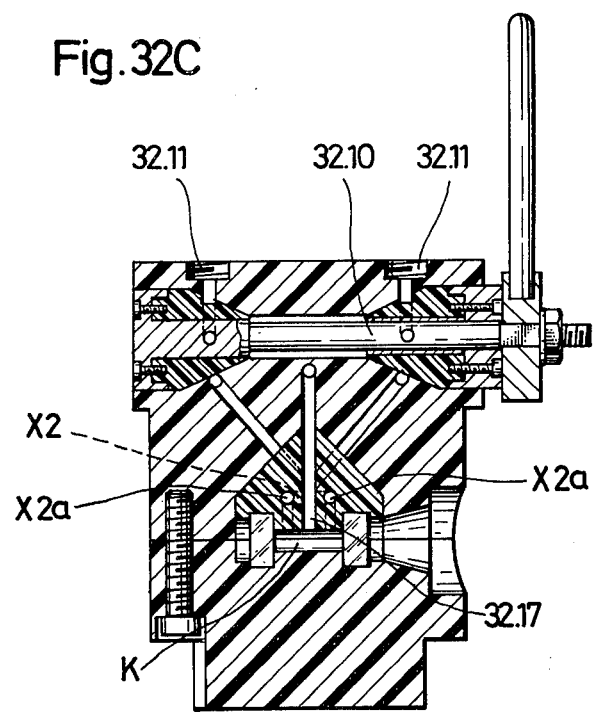
Figure 32B:
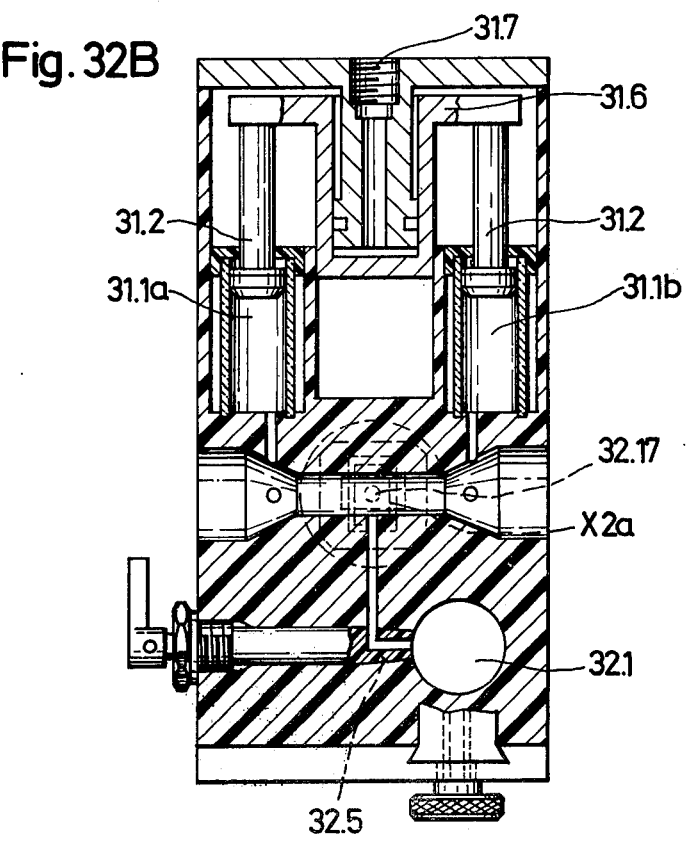

FIGS. 31 and 32: Cells for flow method, with built-in injection device

Figure 33:
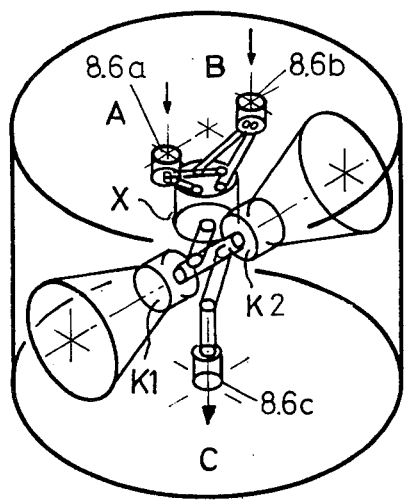
Figure 33:
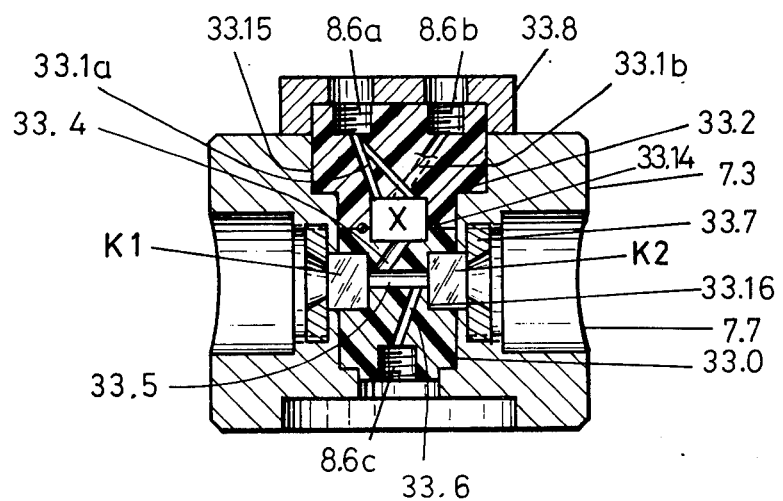
Figure 33:
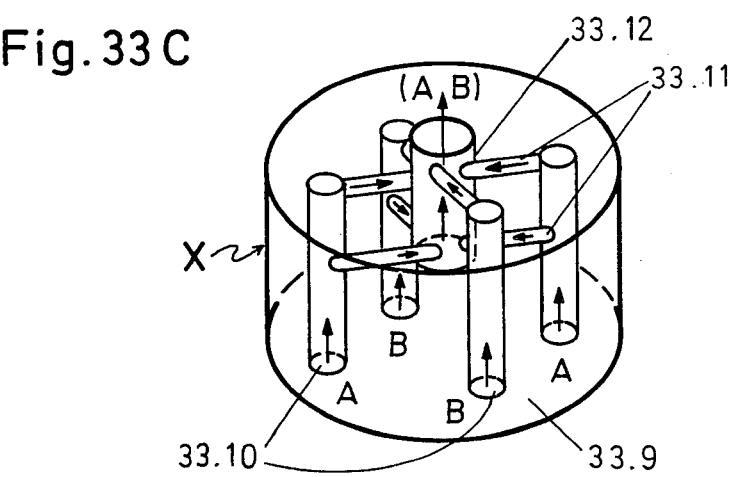

FIGS. 33 to 35: Cells for flow method, with 2 and 4 optical windows, for use with separate injection devices FIG. 36: Injection device for flow cells shown in FIGS. 33, 34, 35, 37 and 38

Figure 37A:
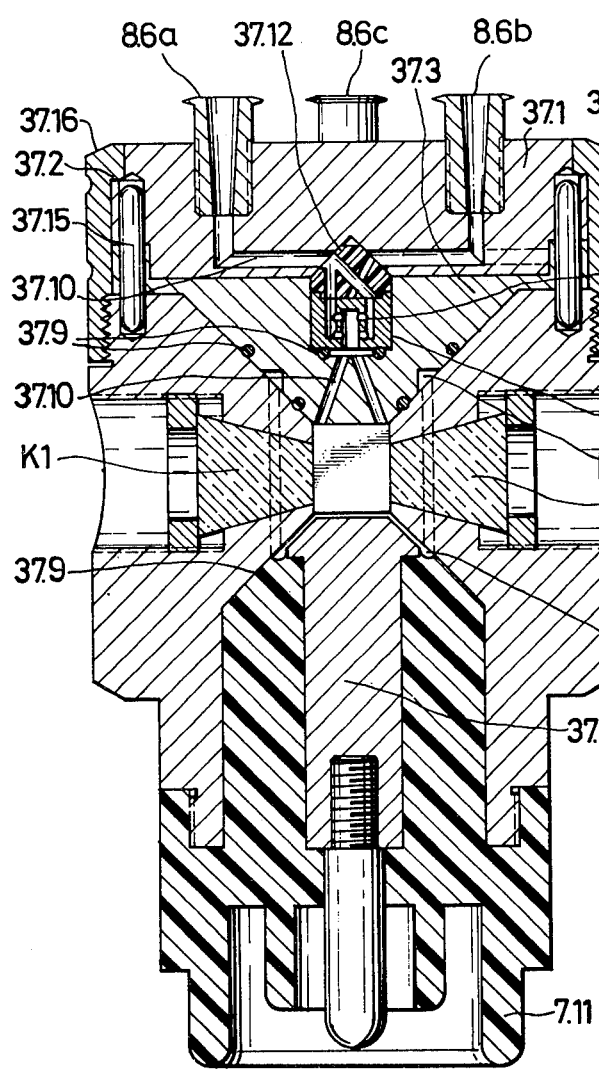
Figure 37B:
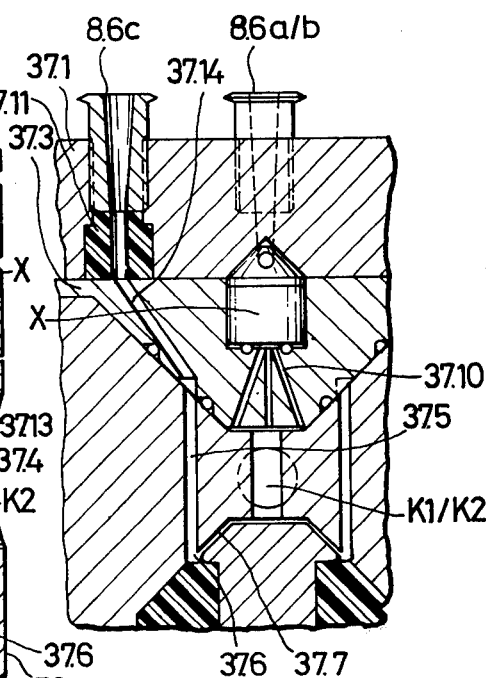

FIG. 37: Combined flow-temperature jump cell for absorption measurements

Figure 38A:
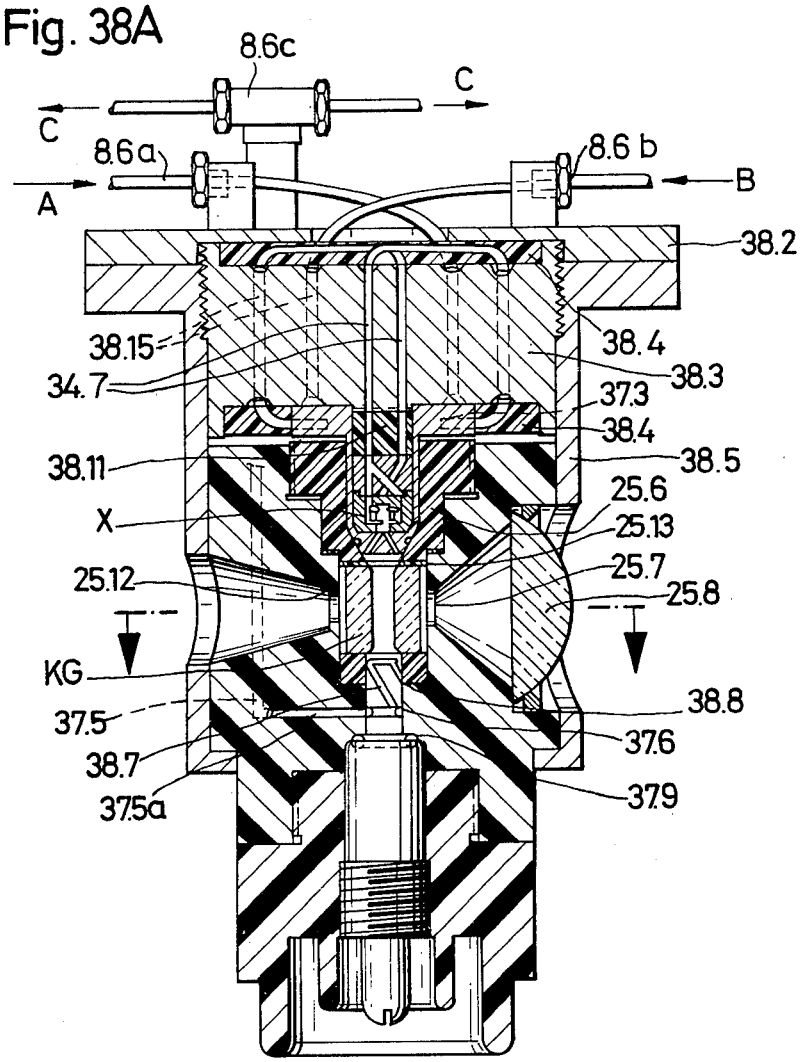
Figure 38B:
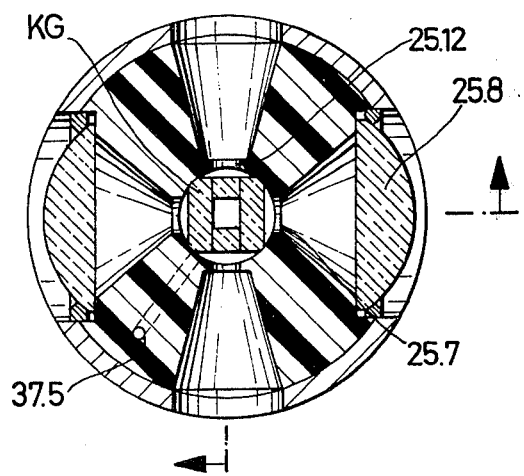

FIG. 38: Micro-cell for flow and temperature-jump measurements

FIG. 39: Device for slow temperature-jump measurements

FIGS. 40 and 41: Cells for flashlight excitation

In all drawings the same symbols are used for units and elements which have the same function. Frequently used parts are denoted with letter symbols which are completed by an index number if necessary. other parts are denoted by a two-digit code number, the first number of which indicates the number of the figure where the part is mentioned first (e. g. 7.11 = High voltage plug-in connector in FIG. 7). The letter code is as follows:

A,B = sample solutions A and B to be mixed
C = reaction product
D = photodetector, general
D1 = reference photodetector
D2 = absorption photodetector
D3,D4 = photodetectors in the secondary lightpath
D1',D2' = additional photodetectors E = functional unit, general
ED = signal processing unit for photodetectors
EH = thermostat
EL = power supply and control unit for flashlight excitation
EM = illumination unit for generating one or more monochromatic light beams
EP = excitation and control unit for pressure-jump and/or flow technique
ES = independent injection device for flow techniques
ET = excitation and control unit for temperature-jump and/or field-jump techniques with high voltage pulse
EZ = cell unit with optical elements
F = spectral filter (F1, F2, . .)
FD = depolarizer
FP = polarimetric analyzer filter
G = flexible light pipe
H = holder or mounting, general
HO = holder for mounting HL1, interchangeable with holder HP
HF1,.. = holder for filter F1,..
HH = device for insertion of holder HP, denoted as prism bed
HL1,.. = mounting for lens L1,..
HP = holder for polarizing prism P and mounting HL1
HZ = cell holder
K = cell chamber or cell (variations: KA,KB,..)
K1,..,K4 = individual cell windows
L = lens (L0,L1,..)
LZ = cylindrical or sphero-cylindrical lens (LZ1, LZ5,..)
M = monochromator
Q = light source
QF = lamp for flashlight excitation
P = prism, usually polarizing prism
PR = prism which rotates the image of a light beam around its axis (variations PRA to PRD)
R = mirror or reflector
S = monochromator entrance slit
S = monochromator exit slit
S1,S2 = radiant field diaphragms at both sides of the monochromator exit
T = beam splitter
TF = dichroic mirror or beam splitter cube
U = optical shutter
V = valve
WA,WB = syringes for injection of sample solutions A and B
X = mixing chamber
Y = collecting syringe for sample solutions
Z = sample cell FIG. 1 shows a simplified diagram of the new apparatus which contains:

1. A sample cell unit EZ for inserting sample cells Z of similar outer shape designed for different mixing and relaxation measurements. These cells are inserted into a holder HZ allowing easy changing, good reproducible positioning and the supply of various perturbation energies. The sample cell unit comprises also optical elements such as lenses, filters and polarizers according to the optical parameter of observation. A thermostat EH is also provided.

2. A series of excitation units: A unit ET for the temperature-jump and/or the field-jump method comprising a high voltage power supply 1.1, a charging resistor 1.2, a high voltage capacitor 1.3 (preferably interchangeable) which may also be constructed as a coaxial cable, a spark gap 1.5, an additional resistance 1.6 which can be adapted to the characteristic impedance of the coaxial cable, and a high voltage connection 1.7 to the sample cell holder HZ. A unit EP for the pressure-jump and/or the flow method comprising a compressed air reservoir 1.10 with reducing valves 1.11, magnetic control valves 1.12, a schematically simplified control circuit 1.13, and suitable connections for compressed air.

A unit EF for the flashlight pulse method comprising a flashlamp QF with a power supply 1.15 and an ignition circuit 1.16.

3. An illumination unit EM for generating one or more high intensity monochromatic light beams.

4. A series of photodetectors D1,D2,D3,D4,D1',D2' connected to a signal processing unit ED.

All functional units and elements are shown as simplified schemes. The illumination unit EM may be constructed as usual. It contains a light source Q with a lamp condenser consisting of the lenses L5 and L6, a mirror R5, and a field lens L9 for illuminating the entrance slit S of a grating monochromator M with high light intensity. For the light source Q powerful high pressure and tungsten lamps are used. Each lamp can be equipped with its own lamp housing and condenser in order to facilitate the changing of the light source. The light beam passing through the slit S is collimated by a lens L0 and directed into the primary light path of the cell unit by a deflection mirror R0. A second lamp condensor, which consists of the elements L5' and R5' can be used to superimposed a second monochromatic light beam. In this case the deflection mirror R0 is replaced by a dichroic mirror or a colour dividing cube. The second light beam can be filtered by an interference filter F0'.

In the sample cell unit EZ part of the primary light enters a reference detector D1 via a beam splitter T and a lens L1. Insertion of a polarizing prism or foil filter P into the lightpath is optional. The light passing through the sample cell is collected by a second lens L2 and directed onto an absorption photodetector D2 via a deflection mirror R2'. The beam splitter T and the mirror R2' can be rotated through 90° in order to direct the light beams onto the photodetectors D1' and D2' instead onto the photodetectors D1 and D2. This switching possibility can be provided, e. g. for measurement with secondary electron multipliers in the ultraviolet spectral range and for measurements with semiconductor photodiodes of high quantum yield in the visible spectral range. (The photodetector D2 is on the axis of the main lightpath normally. It is shown opposite the detector D2' for graphical reasons only. The mirror R2' is then required when the detector D2' is used.) In a secondary light path, which passes through the sample cell at an angle of 90° with respect to the primary lightpath, the photodetectors D3 and D4 can be used for fluorescence and scattered light measurements. The light is collected by the lenses L3 and L4 and filtered by the filters F3 and F4 which normally have wide-band light transmission characteristics. For measurements of fluorescence polarization additional polarimetric analyzer filters FP3 and FP4 are used. For the photodetectors D1, D2, D3, and D4 use of photomultiplier circuits with dynode switching is recommended.

For measurements using the "dual wavelength technique", in which two monochromatic light beams are superimposed for simultaneous recording of the concentration changes of different chemical species, the beam splitter T and the deflection mirror R2' are replaced by suitable dichroic mirrors or colour dividing cubes and the photodetectors D1, D1', D2 and D2' are used simultaneously. Separate reference detectors D1 and D1' should be used for each wavelength, since it is impossible to obtain identical images of the light source at different wavelengths. Changes in the position of the light source (e.g. millisecond period oscillations of the plasma arc of high pressure lamps) therefore lead to different variations of the light flux in each channel. This is far more critical with kinetic measurements than with known statical spectrophotometers.

An example of a recommended optical arrangement is shown in FIG. 2. It is basically similar to the arrangement for temperature-jump measurements already used in the U.S. patent application Ser. No. 487,592 now U.S. Pat. No. 3,972,627, however, several modifications have been made. Contrary to FIG. 1, the monochromator M is equipped with internal deflection mirrors. The light source Q, the monochromator input and exit slits S and S, the sample cell Z with its holder HZ and the absorption photodetector D2 are axially aligned. An optical shutter U, which is closed during the measuring intervals, is placed in front of the monochromator (e.g., during the cooling phase after a temperature-jump). Thus, the exposure of the sample solution so light is reduced and the lifetime of the monochromator and the photodetectors is increased. A second shutter should be provided at the right hand of the beam splitter T. A filter F1, held in a filter holder HF1, can be placed in the collimated light path behind the lens L0, e.g. for suppressing the second diffraction order of the monochromator in measurements in the visible range. A depolarizer FD (e.g. Hanle's quartz-wedge type depolarizer) can be inserted directly behind the beam splitter T. This eliminates the elliptic polarization of the measuring light caused by the grating monochromator and the beam splitter. The spherical mirror R2 (in broken line) can be inserted behind the sample cell for fluorescence measurements without simultaneous recording of absorption changes, thus doubling the primary light intensity. In the case of fluorescent samples which show high absorption of the primary light, a filter F2 with its holder HF2 keeps the photodetector D2 free from fluorescent light. In the secondary light-path the sample cell Z is equipped with lens-ground conical windows (K3 and K4 shown in the cross sectional drawing FIG. 5A). According to the above cited patent application, these windows and the lenses L3 and L4 in the cell holder HZ form immersion optical systems of very high optical efficiency, i. e. with numerical apertures of approximately 0.75 and inner diameters which are approximately equal to the cross sectional dimension of the cell chamber. The cell windows in the primary light path (K1 and K2 in FIG. 5A) may also be lens-ground, where the radius of curvature is chosen for optimal stray light characteristics, i. e. the light reflected at the lens-ground surfaces images the center of the cell or the inner side of the respective opposite window onto itself. The filter holders HF3 and HF4 can be rotated through 90° around the axis of the secondary light path and can hold broad-band emission filters F3 and F4 as well as additional analyzer filters FP3 and FP4 used in measurements of fluorescence polarization. In fluorescence measurements the filter holder HF1 can be used for determing the residual monochromator stray light in the secondary light path by removing the filter F3 or F4 from its normal position and inserting it into the holder HF1. All filter holders have to give sufficient space to hold several filters at the same time.

All lenses and cell windows are made of high quality fused silica which is practically free from strain and fluorescence. Lenses coated for minimal reflection at specific wavelengths can be used in the case of very high requirements for freedom from stray light. This is facilitated by the easy changing of the lenses (to be described below).

The beam splitter T is made of a thin plain-parallel plate of fused silica. Such a plate does not show any absorption in contrast to a semi-transparent beam splitter mirror where the self-absorption can amount to 50% or more in the UV. The reference light intensity is about 10% of the incoming light intensity, which can be considered as optimal for fluorescence measurements. If absorption measurements are also taken into account, a division ratio of 80:20 or 70:30 instead of 90:10 proves to be more favourable. This could be achieved using two or three quartz plates. This arrangement, however, deteriorates the image quality of the light beam and is unfavourable with respect to polarization and effects of interference. An optimized beam divider has been obtained by coating a single quartz plate with a reflecting grating or a raster structure. The raster constant should be about 0.1 to 1 mm (preferably about 0.3 mm). A very small raster constant leads to diffraction patterns, whereas a very large raster constant leads to non uniform splitting of the beam. The raster elements should also be totally reflecting, so that the self-absorption of the coating is negligibly small, and the coated surface should be approximately 10 to 20% of the total surface. Furthermore, the structure of the raster should be positioned so that it is never parallel to the pattern resulting from the orientation of the depolarizer FD. In modified arrangements where the beam splitter is used for deflecting the primary light beam instead of the reference light beam, the coated surface should be 70 to 80%.

FIG. 3 shows a modified version of FIG. 2 which can be used for combined fluorescence and absorption measurements using an extension of the "dual wavelength technique". In kinetic investigations of complex biochemical systems the optimal wavelength $\lambda_1$ for absorption measurements often differs from the optimal wavelength $\lambda_2$ for fluorescence excitation. For highly complex systems simultaneous measurements of different parameters are of special interest in order to obtain as much information as possible and for accurate correlation of the measured data which are needed for complete kinetic analysis.

In comparison with FIG. 2 the following additional elements are used in FIG. 3: One light source Q' with a monochromator M' and lenses L5', L9', and L0' which serve as a second monochromatic illumination unit for the wavelength $\lambda_2$. Further elements are the photodetectors D1' and D2' and the lenses L1' and L2' whose positions have been changed from those shown in FIG. 1, because the two light beams of different wavelengths $\lambda_1$ and $\lambda_2$ are introduced into the sample cell Z from opposite directions. The beam splitter T and the mirror R2' are replaced by the dichroic mirros TF and TF' which, in the 45° position shown, transmit, e. g., 90% of the wavelength $\lambda_1$, whereas 90% of the wavelength $\lambda_2$ are reflected. In order to secure a collimated light path at the mirror TF', the distance between the sample cell Z and the lens L2 is reduced and a collecting lens L20 is inserted in front of the photodetector D2. The filter F2 transmits the wavelength $\lambda_1$ and suppresses the wavelength $\lambda_2$. (The filter F2 shown in FIG. 3 is a high efficiency reflection interference filter used for measurements in the short UV range.) The fluorescence excitation occurs mainly at the wavelength $\lambda_2$. The proportion of the fluorescence signal from an excitation at the absorption wavelength $\lambda_1$ is low if the wavelengths $\lambda_2$ and $\lambda_1$ are chosen appropriately; it can be determined separately if the shutter U' is closed. It can be subtracted from the radiation which is excited at the wavelength $\lambda_2$ in the signal processing unit ED connected to the photodetectors (FIG. 1) The arrangement of the absorption detector D2' with its filter F2' (broken lines) will be needed for dual-wavelength measurements of absorption if the sample cell has only two windows, e.g. in stopped-flow experiments.

The light source A' and the monochromator M' can be omitted in FIG. 3 if the monochromator M is provided with a second exit slit which can be moved with respect to the fixed exit slits singular form to give the light of wavelength $\lambda_2$. A flexible UV-transmitting light-pipe G (broken lines) is connected to the movable exit slit and directed into the right-side light path at the place of the monochromator slit $\overline{S}'$. Monochromators according to Czerny-Turner without internal deflection mirrors (see FIG. 1) are especially suitable for this purpose. The entrance aperture of the light-pipe itself can serve as the additional monochromator exit. For sample cells with a round entrance aperture the waveguide G may furthermore transform a rectangular cross section into a round one.

For pure absorption measurements using the dual wavelength technique a further simplification is possible; after insertion of appropriate lenses, the waveguide G transmits the light of wavelength $\lambda_2$ into the secondary light path (e.g. through the lens L4) which usually serves for fluorescence measurements. Since the light paths are separate it is possible to omit the special interference filters for suppression of interactions between the two channels, especially the dichroic mirrors. A second beam splitter, independent of the wavelength, should be provided in the light path of the second light beam. - In stopped flow measurements, however, an arrangement of FIG. 3 with superimposed parallel light paths will be more appropriate with respect to the sample volume required.

Figure 12A:
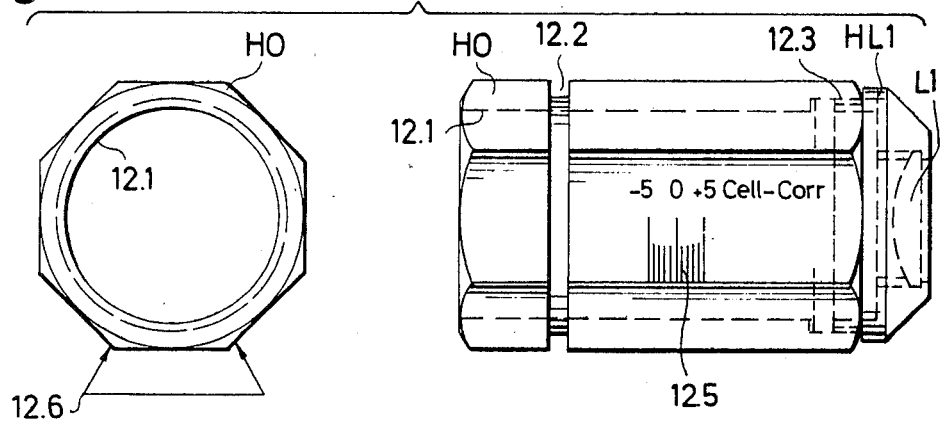

FIG. 4 shows the mechanical outline of a version of the sample cell unit EZ according to FIG. 2. All optical elements following the monochromator and the cell holder HZ, are enclosed in a solid box 4.0 (of, e.g., 300 × 200 × 100 mm). The box is provided with a loose light-tight cover (not shown). The cover has a circular bore above the cell holder with a smaller inserted cover for easy access to the sample cell. All lenses L0 to L4 are inserted in easily interchangeable mountings HL0 to HL4. The lens mountings HL0 and HL2 are provided with means for lateral adjustment of the lens position. Each of them forms a constructional unit with the filter holder HF1 or HF2, respectively. They can be removed from mounting blocks 4.1 and 4.2 by releasing a screw, e. g. in measurements of scattered light by laser irradiation. A perfectly reproducible positioning is obtained by alignment pins. The mounting block 4.2 should be provided with two axially displaced inserting positions. The lens $\overline{L1}$ (masked by the beam splitter T) can also be adjusted laterally to the light path. The beam splitter T together with its holder HT can be replaced by dichroic mirrors or equivalent elements. The beam splitter is mounted in a block 4.3 which is also held in position by means of alignment pins and can be removed by releasing a screw. The prism bed HH is fixed in the same way. The prism holder HP can be moved axially in the prism bed. The polarizing prism P and the lens mounting HL1 are inserted in the prism holder HP (FIGS. 12 and 13). If the prism is not used, the holder HP replaces the holder HP. The box 4.0 has lateral bores for the entrance and exit of light through light-tight flanges or tubes (not shown) which can be connected to the monochromator and the photodetectors, e. g. a tube 14.15 is connected to the photodetectors D3 or D4 (FIG. 14).

A proved version of the sample cell unit uses the following optical data, which are also modifications of the patent application Ser. No. 487 592. Lens L0: Focal length $f_o = 75$ mm at a distance of 80 to 90 mm from the monochromator exit slit $\overline{S}$ with a free lens aperture of 29 mm. The grating or prism of the monochromator (aperture ratio e.g. 1:35) is imaged on the polarizing prism P at a distance $f_o$ from the lens L0. A Glan-air type prism with a free aperture of about 20 mm is recommended for the polarizing prism. A larger focal length $f_o$ would require a more complicated prism with a larger cross section, however, for measurements without the polarizing prism $f_o = 100$ mm can also be used at a distance of 105 to 110 mm from the monochromator. A slightly convergent lightpath is obtained which allows a relatively large distance between the lens L0 and the cell holder HZ, so that after removal of the prism bed HH enough space is available for further modifications of the primary light path (such as for a fast modulator in modulated light systems). The lens L0 will be still designated as a "collimating lens", even if the light beam behind this lens is not strictly collimated. Several different focal lengths are available for the lens L1, e. g. $f_1 = 25, 35, 50,$ and $75$ mm, for adapting the image of the monochromator exit slit to the respective sample cell (discussed below). As a standard focal length $f_1 = 50$ mm is used. The free aperture of the lens L1 for the case where $f_o = 75$ mm is 19 mm. For the lens L2 a focal length $f_2 = 50$ mm with a free aperture of 29 mm is recommended; if $f_1 \leq 35$ mm L2 is replaced by a lens of a shorter focal length. The concave mirror R2 should be made of fused silica, coated on the back with concentric spherical surfaces. Compared to a 1st surface mirror this offers the advantages of a higher degree of reflection, slower ageing and easy cleaning. The focal distance of the lens $\overline{L1}$ can be $\overline{f_1} = 100$ or $150$ mm. The lenses L3 and L4 correspond to those shown in the above cited patent application (respective lenses L7 and L8). By means of further lenses and stray light diaphragms an intermediary image of the chamber volume of the sample cell can be obtained in the secondary light path, especially if sample cells with a chamber shown in FIG. 22 and the following figures are used. A more compact mounting at reduced variability of the optical set-up can be obtained by using shorter focal lengths in the primary light path, e. g. $f_o = 50$ mm and $f_1 = 35$ mm. Other variations use mirror optical arrangements where the focal lengths are independent on the wavelength; however, they require a more complicated construction.

For fluorescence measurements on strongly absorbing samples using the front-on technique (c. f. above cited patent application) the sample cell in FIGS. 2 and 4 is rotated by 90°. The lens L1 is removed from the light path. Instead, one of the two lenses L3 or L4 is inserted into the cell holder on the side of the incoming light, thus imaging the aperture of the lens L0 (or the grating aperture of the monochromator) onto the cell chamber. A dichroic mirror is mounted close to the cell holder at the approximate position of the lens L1. The light beam coming from the monochromator passes through this mirror and the emitted fluorescent light is reflected either vertically or horizontally through an angle of 90°. An additional, usually closed, connecting flange with a further filter holder is provided as an alternative position for one of the two emission photodetectors D3 or D4. This arrangement yields a considerably increased light gain compared to the former front-on arrangement in which the beam splitter T is replaced by the dichroic mirror and the emission photodetector is placed opposite to the reference detector D1.

In arrangements shown in FIG. 3, additional optical elements — such such as the dichroic mirror TF', the filter F2, and the lenses L0',L1', and L20 - can be enclosed in an accessory beam splitter unit outside the sample cell unit shown in FIG. 4. Such a beam splitter accessory completes the standard equipment of the new apparatus according to the block building system described below.

CELL HOLDER AND SHAPE OF SAMPLE CELLS

The cell holder HZ shown in FIG. 5 has 4 window bores 5.3 which should be conically reduced on the inside. The lenses L3 and L4 have mountings HL3 and HL4 which are screwed into threads 5.5. Lateral bores 5.5a in the lens mountings allow the thread to be tightened and released by means of a simple key. The same applies to the mounting HR2 of the mirror R2. The cell holder has a metal body 5.0 with a cylindrical bore 5.2 and a flat cone 5.7 for insertion of cells of "type A" and "type B" as shown in FIGS. 7 and 8. "Type A" cells, especially temperature-jump and field-jump cells, are fixed by a mounting ring (e. g. according to FIG. 5C) with a thread 5.27 which fits into a counter thread 5.4. They have a conically shaped taper 7.9 which is tightly pressed against the cone 5.7. "Type B" cells, especially flow and pressure-jump cells, have a flange 8.4 which is screwed on the top of the cell holder by 2 or 4 screws fitting tap holes 5.1. Perfect adjustment of the optical axis is obtained by two opposite slot springs or slot blocks 5.21 which fit into slotted gaps 7.8 of the cells.

For temperature-jump and field-jump measurements the bottom side of the cell holder is equipped with a high voltage connector with a spring socket 5.15 and a profiled high voltage insulator 5.14 which secures a high dielectric strength. A high voltage plug-in socket 7.11 on the bottom of the cell possesses the corresponding positive profile (e. g. in FIG. 23). It is connected to the excitation unit ET by a coaxial cable 1.7 with a similar coaxial plug (not shown) which is fastened with good electric and thermal contact to a connecting flange 5.13. The coaxial cable is covered with a heat insulating hose which lowers the loss of heat by conduction. The insulation of the plug should be made of the same material as the cable insulation (e. g. polyethylene). Thermoplastic sealing of the insulating material is recommended. - For flow- and pressure-jump measurements easily removable, pressure resistant hose connections 8.6 are provided on the top of the cell (FIG. 8).

For liquid-thermostatting of the cell holder a system of holes 5.19 is provided five of which can be seen in the cross sections. The thermostat EH (FIG. 1) is connected to liquid connection tubes 5.12. A plate of plastic material 5.17 serves for thermal insulation of the bottom of the box 4.0. The high voltage connection and the free surface of the cell holder can be covered with foamy plastic. For experiments below the dew point or in the UV at 200 nm or below, a purging gas system is used which consists of a connection 5.16, a circular channel 5.10 and four ascending channels 5.8 and 5.9 each with outlets directly below the windows. The inner channels 5.9 ventilate the aperture of the cell windows 7.7 via the bores 7.12 in the body of the cell. The channels 5.8 leading to the outside, together with the lens mountings HL3 and HL4 and one conical gap 5.6, form a distribution system with jet bores 5.6a around the lenses L3 and L4. positions 5.20 which are not used can be closed. For temperatures which differ considerably from room temperature the gas is first led to a head exchanger which is connected in series to one of the thermostatting connections 5.12.

Samples cells for the temperature-jump and the field-jump methods of "type A" shown in FIG. 7 are usually made of plastics, preferably of hard high-polymers. Special care has been taken to obtain perfect mechanical, thermal and electrical contact between the cell holder and the upper part of the cell with a metal cover 7.4, which mounts the grounded upper electrode (e. g. FIG. 23). In previous constructions difficulties occurred because of the different thermal expansion coefficients of the plastic body and the metal cell holder. Thus, the cell was either jammed, or it was too loose which led to vibrations because of the mechanical forces caused by the temperature-jump (magnetic forces, and pressure shock-waves when the solution was heated). This problem is completely overcome by the conical fittings 5.7 and 7.9, together with the mounting ring of FIG. 5C which contains an axial spring element 5.26 between an inner ring 5.28 and an outer ring 5.22. The spring elements can be a flat or slightly profiled circular disk of bronze or steel plate. Position 5.25 are safety pins. Thermal contact is guaranteed by greasing the sliding cylindrical surfaces between the rings 5.22 and 5.28. Electrical contact is established by the spring disk 5.26 itself, by the close fit of the ring 5.28 to the cell cover 7.4 and the contact between the threads 5.4 and 5.27. The mounting ring has a knurl 5.29 and bores 5.24 for a socket key which is only needed for flow cells. The movement of the spring element is limited by stops provided with the rings 5.22 and 5.28.

For measurements of temperature, FIG. 7 provides a thermometer probe 7.1, e. g. a platinum resistor connected to a digital instrument. The probe has a pin 7.2 which fits into a bore 7.6 in the head of the cell with a close-fit air gap of e. g. 1/100 mm.

FIG. 6 shows a modified cell holder which is suitable for the insertion of sample cells of "type C" shown in FIG. 9. The middle (9.3) and lower parts (7.10) of these cells are similar to the cells shown in FIGS. 7 and 8. Up to four lateral window apertures 9.7 and, if necessary, a high voltage plug connector 7.11 are provided on the bottom. A box-shaped body 9.4 is mounted on the top of the cell which allows sample cells of different construction to be used. FIG. 6 shows a version of a cell holder where the cylindrical part 9.3 of an inserted sample cell is fastened in the upper part of a vertical bore 6.2 by turning the lever 6.30 of an eccentric shaft 6.31. Lateral bolts 6.34 transmit the force produced by the rotation of the shaft 6.31 to the opposite side of the bore 6.2 which will be elastically deformed since two cross holes 6.32 are provided with slotted gaps 6.33. The elastic deformation gives a tight contact between the cell holder and the cell. Reproducible positioning of the sample cell is obtained by an alignment pin (22.12 in FIG. 22) which fits into a slot 6.21 in the upper part of the body 6.0. The lenses L3 and L4, with the corresponding mountings, can be inserted into two lateral holes 6.3. Threaded connections 6.12 and a circular channel 6.19 around the high voltage insulator may be sealed (e. g. by means of O-rings 6.35) and can be thermostatted. A bore 6.16 serves as input for the purging gas. The high voltage connections 5.13, 5.14, and 5.15 correspond to those in FIG. 5.

SPECIAL PROBLEMS WHEN COMPARING KINETIC AND STATIC DATA

For all optically studied chemical reactions a comparison of the kinetic data with the equilibrium data obtained with static spectrophotometers is needed. This is especially true for a correct correlation of the absorption, excitation, and emission bands of the individual reactants and the resulting analysis of the reaction amplitudes. Whilst static spectrophotometers work with low optical bandwidth to give a high spectral resolution, fast kinetic investigations need measurements with large optical bandwidths to obtain light intensities which give a satisfactory signal-to-noise-ratio at a high time resolution. Integration over the optical bands of the reactants is inevitable. Of course, many static spectrophotometers can be adjusted to give larger optical bandwidths, however, satisfactory linear processing of the resulting light intensities cannot be achieved by their photodetectors. In kinetic apparatus light beams of much higher convergence are used, too.

In most cases the conversion to low optical bandwidths proves to be a complicated mathematical problem, since the transmission characteristics of the whole optical arrangement, as well as of the monochromator and the filters, has to be known precisely. This applies especially to the spectral characteristics of the light source and photodetectors. The use of light sources with line spectra, especially high pressure mercury lamps, facilitates the procedure if a highly selective insulation of one stronger individual spectral line can be achieved (e. g. mercury line 404.7 nm). However, this does not always apply. Frequently, there are several spectral lines within the pass-band of the monochromator and the conversion becomes even more difficult for a continuous light source (e. g. mercury-band spectra between 280 and 300 nm). For complete calibration of the apparatus a large number of parameters has to be considered and the transmission characteristics has to be known in steps of 2 nm or less for different monochromator slits, light sources, photodetectors, filters, polarizers, etc.

As already mentioned, in kinetic measurements rather different measuring conditions have to be used for different time ranges, for different parameters of perturbation and observation, and for different sample volumes, especially when both mixing and relaxation techniques are applied. In the improvement as described below these problems have been overcome by the utilization of variable, interchangeable optical elements in the light path. This enables optimal adjustment of the instrument for the respective time range and the respective sample cell. Although it would be ideal to have interchangeable sample cells for all different perturbation parameters which have identical optical characteristics, it is often necessary to work with different optical bandwidths and light beams of different convergence. An accurate quantitative comparison of the different kinetic measurements may thus prove to be as difficult as for the correlation of the kinetic data with the static data. As in many other physical measuring problems governed by a law of information theory, simultaneous high resolutions of optical spectrum, time and amplitude and small amounts of the sample are incompatible.

ADAPTORS FOR INSERTING CONVENTIONAL SPECTROPHOTOMETER CELLS

In order to facilitate a comparison between the different kinetic and static data, FIGS. 10 and 11 show adaptor accessories for using conventional spectrophotometer cells in the sample cell unit of the new apparatus. The adaptors match the cell holders of FIGS. 5 and 6. Thus, comparative static data can be obtained which show the influence of bandwidth and beam convergence in comparison to measurements at small bandwidths and almost parallel lightpaths as obtained with static spectrophotometers. Moreover, it is possible to investigate the influence of bandwidths variation, change of beam convergence, etc. for a precise comparison of different kinetic data. Using conventional cells for these kinds of measurements offers the advantage of easy handling, whereas inserting kinetic cells into the lightpath of static spectrophotometers may be difficult.

Figure 10A:
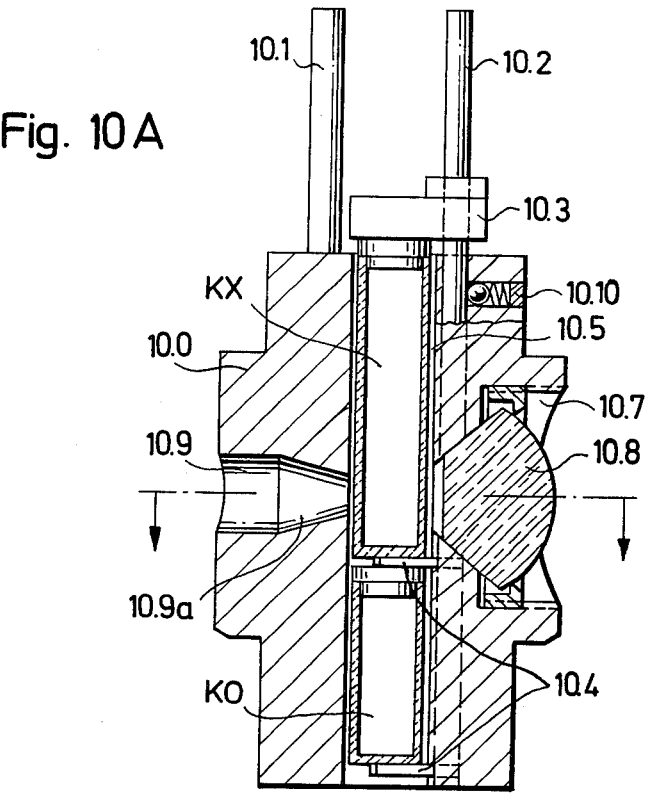
Figure 10B:
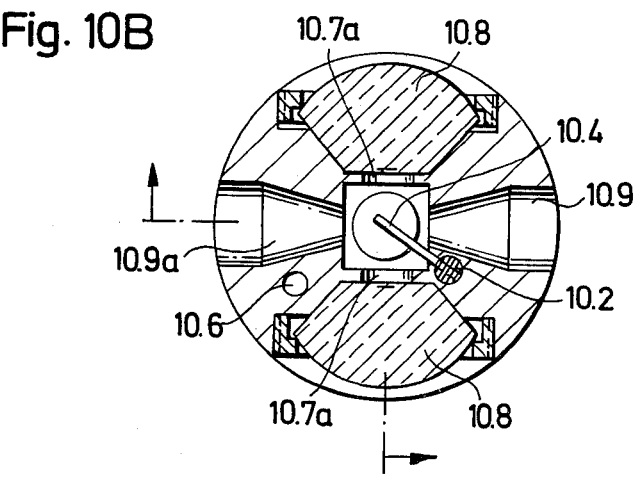

The cell adaptor shown in FIG. 10 is constructed for conventional rectangular cells, especially for cells with outer dimensions of ½ × ½ inches or inner dimensions of 10 × 10 mm. The vertical cross section of FIG. 10A is deflected in the vertical axis. It shows the primary lightpath on the left hand side and the secondary lightpath on the right hand side of the drawing. FIG. 10B shows a horizontal cross section without the cell. A metal body 10.0 with a handle 10.1 is placed thightly into the cell holder HZ by which it is thermostatted. A bore 10.6 is provided for the temperature sensor 7.1 shown in FIG. 7. A rectangular bore 10.5 is provided for insertion of a cell KX. A reference cell KO of smaller height can be inserted below the cell KX if necessary. For fluorescence measurements, the reference cell KO can be replaced by a fluorescence standard (fluorescent glass or plastic). The change between measuring and reference positions is effected by a lift with a push-bar 10.2, mounting device 10.3 and 10.4 and a ball stop device 10.10. The window bores 10.7 in the secondary lightpath possess diaphragm apertures 10.7$a$ directly in front of the cell. These diaphragm apertures may be either conical or oval. Furthermore, the window bores are equipped with conical lenses 10.8, similar to the conical cell windows K3 and K4 shown in FIG. 5A. The window bores 10.9 in the primary lightpath may be either conical or cylindrical with stepwise reduced diameters; the diaphragm apertures 10.9$a$ may be circular or oval. Interchangeable diaphragms may be used, too. The thickness of the cell windows is different from the cell windows K1 and K2 shown in FIGS. 5A, 22, and other cell constructions described below; however, it is possible to compensate for these differences by a so-called "cell correction" in the primary lightpath, as described in FIG. 12. The size of the lenses 10.8 in the secondary lightpath has to be chosen so that comparable conditions are obtained without further corrections.

The adaptor can also be modified to match the dimensions of other spectrometer cells.

Figure 11A:
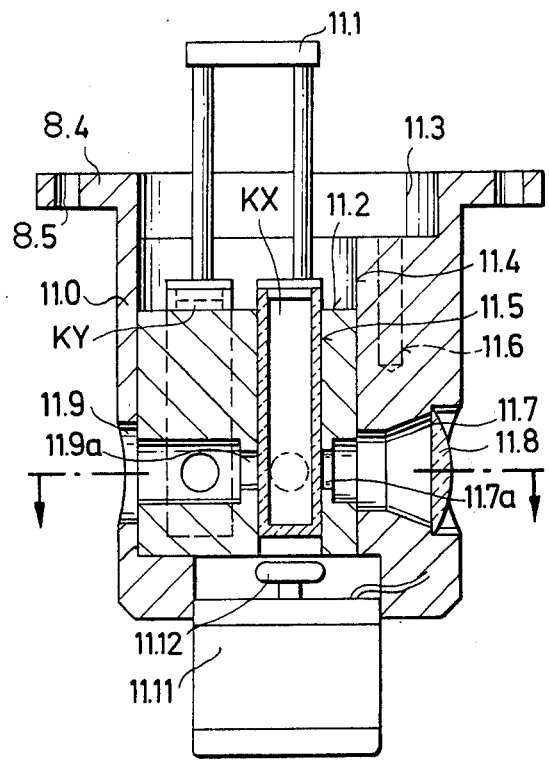
Figure 11B:
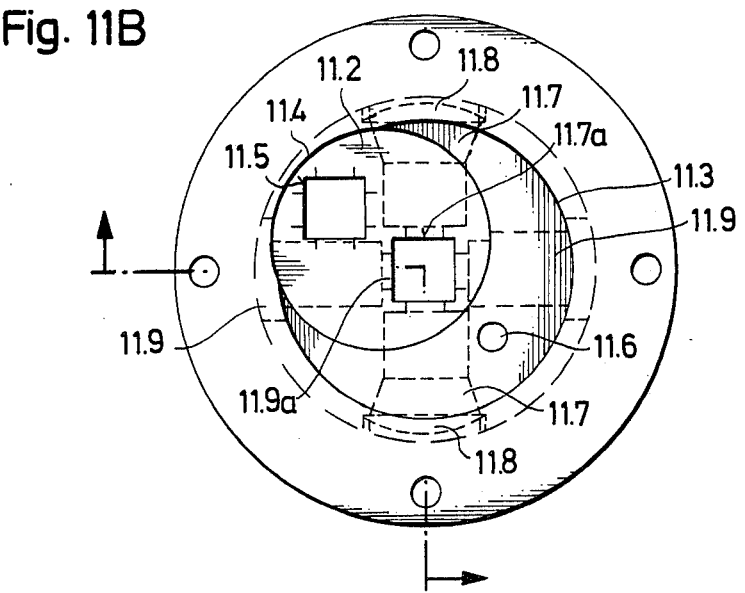

FIG. 11 shows an adaptor which is constructed as a sample changer for two rectangular cells KX and KY with an inner width of, e.g., 7 × 7 mm. This size is very close to the inner dimensions of many kinetic cells. FIG. 11A shows a vertical cross section which represents half of the construction in the primary and secondary lightpaths. FIG. 11B shows a horizontal plan with the window bores and without the cells. A metal body 11.0 with a mounting flange 8.5 corresponds to sample cells of "type B" shown in FIG. 8. An eccentric cylinder bore 11.4 and a cylindrical bore 11.3, which overlap each other, serve for insertion of a cylindrical rotary body 11.2 with a handle 11.1 and two rectangular bores 11.5. A ball stop device (not shown) enables adjustment of the optical axis. The window bores in the primary and secondary lightpaths (11.9, 11.7) may again be either conical or cylindrical with stepwise reduced diameters. In the secondary lightpath the lenses 11.8 are used to improve the light gain for fluorescence measurements. Furthermore, a thermometer bore 11.6 and a small motor 11.11 with a magnetic stirrer 11.12 are provided below the cell KX. A second magnetic stirrer under the cell KY can also be driven via a transmission element. These magnets can be used to drive smaller magnetic stirrers within the cells, to guarantee thorough mixing of the sample solution when performing titrations. Eddy currents can be minimized by slotting the bottom of the rotary body 11.2.

The adaptors of FIGS. 10 and 11 have been found very useful for executing static titration-series experiments, especially those involving measurements of fluorescence intensities and fluorescence polarization, which precede the kinetic investigations. In FIG. 11 the smaller aperture and thus lower light gain in the secondary lightpath can be accepted. In measurements of fluorescence polarization this results in a different value of the large aperture correction which may be adjusted by electronic means of the signal processing unit ED already described in the patent application Ser. No. 487,592. A similar sample changer can be constructed for three cells if one of the four window bores is omitted, e. g. for measurements of absorption and fluorescence intensities.

VARIABLE LENS MOUNTING IN THE PRIMARY LIGHT PATH

Figure 12B:
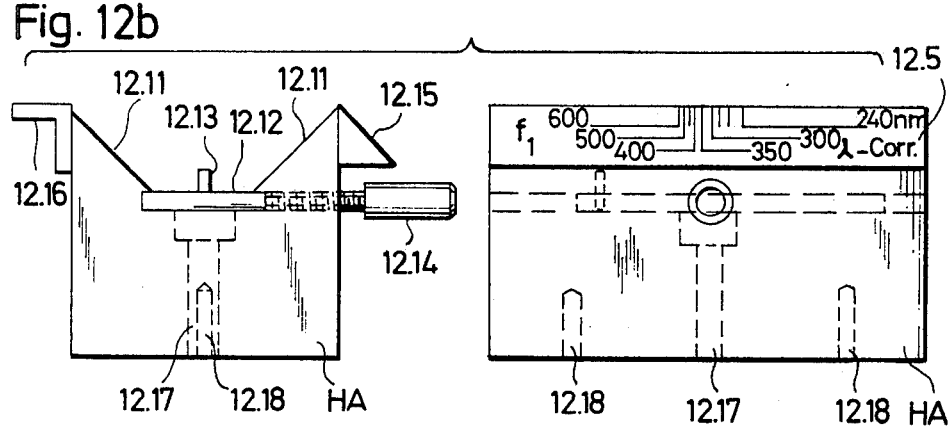
Figure 13:
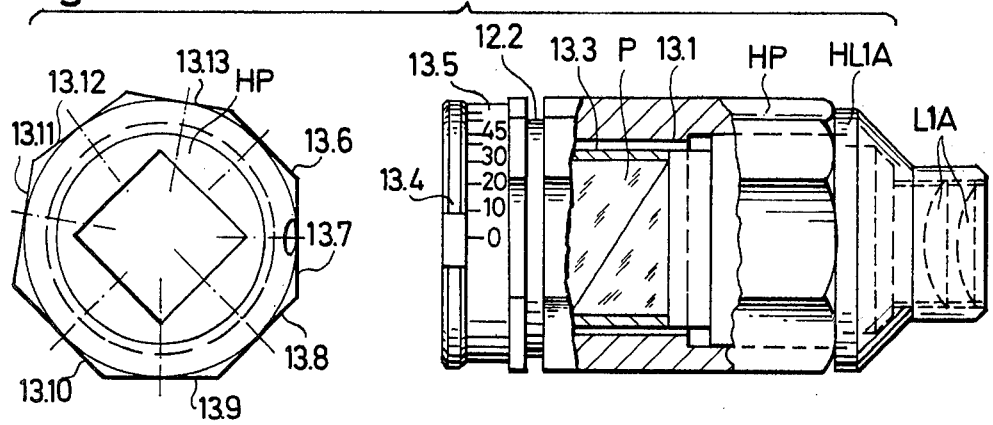
Figure 25:
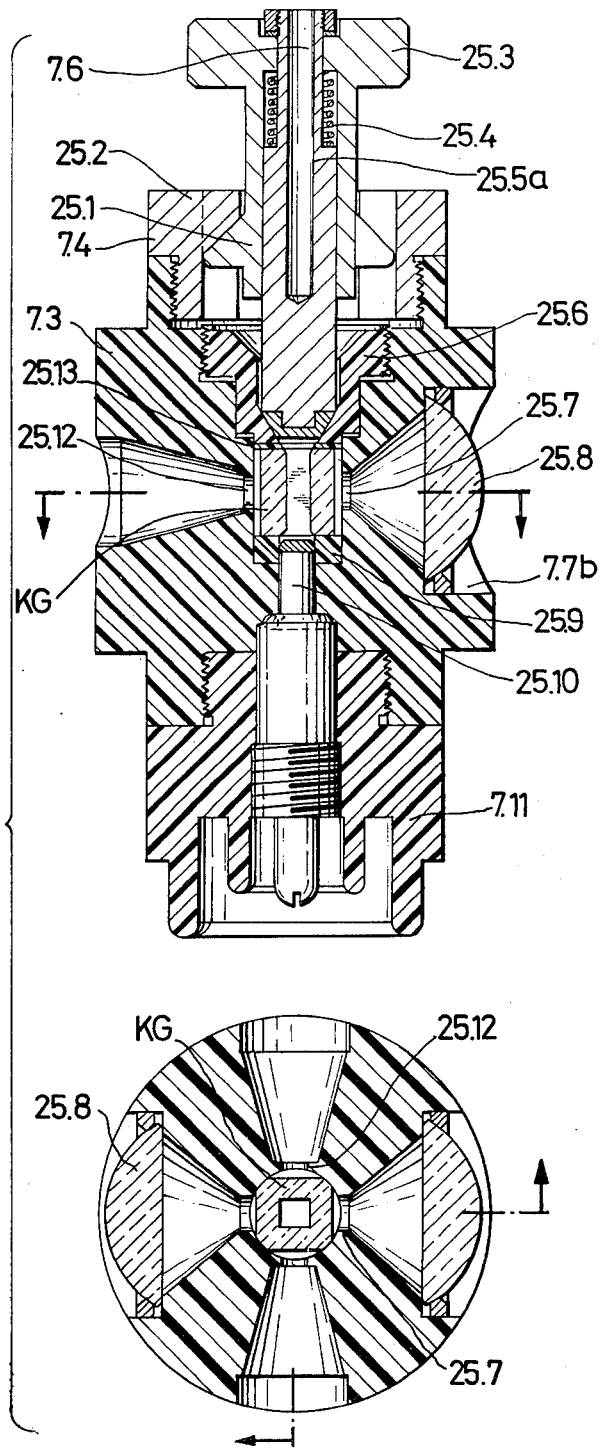

Detailed representations of the prism bed HH and the prism holder HP of FIG. 4 are given in FIGS. 12B and 13, respectively; FIG. 12A shows a holder HO which is used instead of the prism holder HP for measurements without the polarizing prism P. Each of the holders HO and HP fit the lens mounting HL1 and thus the lens L1 by a thread 12.3 or a plug-in socket. As already mentioned, lenses L1 with various focal lengths should be provided. Due to the thread 12.3, the lens L1 can be interchanged easily two versions of which are shown at the right hand sides of FIGS. 12A and 13. The latter one (denoted as L1A) is a double lens system of short focal length and high aperture ratio of up to 1:1.2 which is very useful for measurements with microcells in the microsecond range (e. g. FIG. 25). All lenses L1, L1A,... have their own mountings HL1, HL1A,..

The holder HO is shaped as a regular octogon in its cross section. It is inserted into the prism bed HH so that two planes 12.6 of the holder which are at right angles are placed on two planes 12.11 of the prism bed which are inclined at angles of 45° with respect to the vertical axis. In a simplified version the holder HO is constructed as a cylinder or as a cylinder with two or three plane surfaces 12.6. The prism bed is equipped with a mobile plate 12.12. A pin 12.13 on the plate 12.12 fits into a slot 12.2 of the holder HO. The plate can be stopped by knurled screw 12.14. A bore plate 12.12 gives access to a screw in a bore 12.17 so that the prism bed can be removed from the cell unit of FIG. 4. Similar to other removable components, the position of the prism bed is determined by alignment pins that fit two bores 12.18.

WAVELENGTH AND CELL CORRECTION

A correction for the wavelength dependence of the image plane of the monochromator exit slit $\overline{S}$ in the sample cell can easily be achieved by shifting the holder HO and the lens L1. For the commonly used focal length of, e. g., $f_1 = 50$ mm, the correction can be indicated directly on a scale 12.15 which is fixed either to the holders HO and HP or to the prism bed HH. For other focal lengths further scales or a millimeter scale 12.16 can be provided, too, on the holder or the prism bed. A second scale 12.5 opposite the scale 12.15 indicates the correction of the lightpath in the sample cell (cell correction). In the case of a sample cell with plain parallel window surfaces, each millimeter of the light path in water corresponds to a focal difference of 0.25 mm compared to air. For fused silica the difference is 0.33 mm. or many standard cells this difference amounts to +5 mm, by which the lens distance has to be increased. Because of the high aperture of the light path, this difference is much more critical than for static spectrophotometers. Cells with lens-ground windows, whose curvature is roughly concentric with the center of the cell, as the window K1 in FIG. 5A, do not show any difference with respect to air. If, however, the sample solution is not homogeneously heated in temperature-jump measurements or if the cell windows are slightly deformed in pressurejump measurements, it is favorable to focus the primary light beam nearer onto the exit aperture of the cell which corresponds to a negative cell correction.

The lenses L0, $\overline{L1}$, and L2 could also be moved for correcting the chromatic error. The lenses L0 and L1 may be moved separately or together. In the commonly used spectral range of 240 to 600 nm it is sufficient to move only one lens if the instrument is optimally adjusted for an average wavelength of, say, 300 nm. Different adjustments are necessary for measurements in the lower UV range around 200 nm which require a deuterium lamp as a light source and nitrogen as a purging gas. A correction of the distance of the lens L0 can then be achieved by shifting the monochromator on an optical bench. As to the lenses $\overline{L1}$ and L2, the photodetectors can be moved from their marked standard positions. Two or three inserting positions can also be provided for the lens holder HL2 on the mounting block 4.2.

MOUNTING OF POLARIZING PRISM P

The prism holder HP shown in FIG. 13 can easily be interchanged with the holder HO for measurements involving effects of polarization. For quick interchange of both holders, two pieces of the commonly used lens L1 with its mounting HL1 may be supplied with the apparatus. The holder HP has a slot 12.2, too, for axial positioning by the pin 12.3, as well as a scale 12.5 for cell corrections. The polarizing prism P should be arranged in a mounting 13.3 which can be rotated in the bore 13.1. The rotary position of the prism can be changed by a knurled collar 13.4, and is read directly from a graduated ring 13.5 with a scale of 0° to 90°. The profile of the holder HP has the form of an irregular octagon. The normal vectors of the five planes 13.6 to 13.10 and of the three planes 13.11 to 13.13 subtend angles of 45°, whereas the vectors of the planes 13.6 and 13.13 subtend an angle of 35.3°. The prism is adjusted so that the electrical vector is exactly vertical at the 0° position of the continuous scale 13.5 and at upside position of the plane 13.13. When the holder HP is inserted into the prism bed HH, the following orientations are obtained which are preferred for polarimetric measurements:

Table I

| Orientation | $I_v:I_H$ | scale 13.5 | upside plane |
|---|---|---|---|
| 0° | 1:0 | 0° | 13.13 |
| 45° | 1:1 | 0° | 13.12 |
| 90° | 0:1 | 0° | 13.11 |
| 35.3° | 2:1 | 0° | 13.8 |
| 54.7° | 1:2 | 90° | 13.8 |

The ratio $I_v:I_H$ is the ratio of vertical to horizontal intensity. The values in the first column of Table I are indicated on the planes listed in the last column. The scale 13.5 is lettered such that the rotary angle of the prism is obtained as the sum of the respective fixed angle and the value on the continuous scale. Wavelength and cell correction is performed at the 0° position. The prism holder can be rotated or replaced by the holder HO without changing the axial position.

In an alternative version of the prism holder HP, the prism is mounted in a hollow bearing with a ball stop or similar device, so that the main stop positions indicated in Table I can be easily set. The bearing is mounted on a swivel arm or plate so that it may be moved into the light path. Such a swivel device is especially useful for the depolarizer FD. The lenses L1, L1, etc. may also be arranged on a revolving device. For the wavelength and cell corrections a suitable axial sliding device has to be provided.

MOUNTING OF EMISSION FILTERS AND POLARIZATION ANALYZERS

FIG. 14 show the rotary filter holder HF3 (HF4) in the secondary lightpath. FIG. 14A shows a complete cross section of the mounted filter holder, whereas FIG. 14B gives a perspective representation pf its essential parts, i. e. the filter pocket 14.0, the rotor 14.5, and the stator 14.8 of the revolving device. FIG. 14C shows the corresponding stop device to be used for adjustment of the preferred rotation angles 0°, 53.7° (or 55° with respect to the large emission aperture), and 90°.

The filter pocket 14.0 has a bore 14.1 which fits the free aperture of the lenses L3 and L4. An oblique gap 14.2 in the side of the filter pocket facilitates the insertion of the filters which are held in position by means of springs 14.2a. The collar 14.3 of the filter pocket is fastened to the outer ridge of the rotor 14.5 by means of threaded pins 14.4. When the rotary device is mounted, the rotor is placed onto a cylindrical socketpiece 14.9 of the stator 14.8. The stator is screwed (14.12) to a bore in the side wall 14.13 of the box 4.0 which is parallel to the primary light path (FIG. 4). By insertion of a disk 14.14 the collar 14.6 of the rotor is held in a slot 14.10 of the stator allowing easy rotation. The stator has a gap 14.11 for the rotor handle 14.7, which allows the rotor to be rotated by 90° or slightly more. The stop devide consists of a stop ring 14.16 with gaps 14.16a, 14.16b, and 14.16c corresponding to the above mentioned rotation angles. A pulley 14.18 (e. g. a small ball bearing) fits into these gaps. The pulley is mounted on a spring-loaded lever 14.17, 14.20. The gaps 14.16a, 14.16a, 14.16b, and 14.16c are made by a cylindrical cutter which corresponds to the diameter of the pulley 18.18, and undercut by a smaller cylinder cutter. This procedure secures a quick, backlash-free catching of the pulley and avoids erroneous adjustments of the stop angles. If an arbitrary rotation is required, a small block 14.21 (made of, say, PTFE) can be put onto the axis 14.19 of the pulley 14.18 (FIG. 14A). For this purpose the rotor handle 14.7 can be equipped with an additional angular graduation.

A light protection tube 14.15, with a bore for light-tight insertion of a photodetector in the emission light path D3 or D4, is mounted on the stator 14.8. The shown rotary filter holder is a typical hollow bearing with the added feature that it allows a rotary movement through the wall 14.13 with complete exclusion of room light, and still allows a fixed mounting of the protection tube 14.15 to the box of the sample cell unit EZ. Contrary to known constructions, no gear drive is needed. Additional lenses in the secondary lightpath may be inserted into the bore 14.8a.

IMAGING OF LIGHT SOURCE AND CONDENSOR ARRANGEMENTS

FIGS. 15 to 19 describe the imaging of the light source Q onto the monochromator entrance slit S and the measures which influence this image so that a high light gain and a highly stable light flux can be obtained. These arrangements have been specially designed for using high-pressure discharge lamps.

The lamp condensor, comprising lenses L5, L6, etc., and/or a mirror R5, and a filed lens L9 (FIGS. 1 and 2), is usually designed as a high aperture system in order to obtain a maximum gain of light. However, a large aperture ratio of the condensor is equivalent to a corresponding large image magnification. At the monochromator entrance slit S, positional fluctuations of the light source Q result in a modulation of the light flux which becomes a limiting factor of the resolution of the instrument. Positional fluctuations and oscillations are typical with high-pressure lamps and are due to instabilities of the plasma arc. This effect increases with increasing image magnification. Because of the required high differential sensitivity of the kinetic apparatus, modulations of the light flux are much more critical than with static spectrophotometers. The periods and time constants of these instabilities are mainly in the ms-range. For these reasons a slit illumination according to FIG. 15A gives a higher light intensity than one according to FIG. 15B but it is more sensitive to arc oscillations. Therefore, the first illumination is appropriate for measurements in the $\mu s$-range, where the optical noise becomes the major limiting factor, and the other one is more appropriate for measurements in the ms-range, where the stability problem becomes dominant. Accurate tests with kinetic measurements lead to the result that, in a time range of $1:10^6$, or more, no uniform value for an optimal magnification of the lamp condensor can be indicated. This fact has been disregarded until now. An arrangement for quick change of the condensor aperture and magnification used with the new apparatus will be described in FIG. 18.

Due to the fact that kinetic measurements often extend over a very wide time range, there is still the need for a better compromise between light stability and optical noise. This better compromise is obtained if the image of the light source Q onto the monochromator slit S is rotated by 90° which is shown in FIGS. 15C and 15D. In this case the light gathering power of the monochromator is not totally exploited so that, at constant condensor magnification, a loss of the light gain must be accepted. From the drawing it can be seen that oscillations of the light arc in FIG. 15C will have a much smaller influence than in FIG. 15A. The light arc starts at the top of the cathode marked by a minus sign (−) and moves perpendicularly to the lamp axis. If the displacement is not too large, the light flux passing through the monochromator will remain approximately constant. The proportion of the light gathering power of the monochromator which is not utilized for a gain of light intensity, represents an "auxiliary light gathering power" which is used to compensate for the displacement of the arc. The loss of light flux is lower than one may expect from a first glimpse. The area of the highest light intensity is concentrated near the cathode, as can be seen from the shown lines of equal intensity. On the other hand, the light arc is especially unstable in the neighbourhood of the anode which is marked by a plus sign (+). Consequently, if the neighbourhood of the cathode is imaged onto the slit S, one obtains a gain in stability of 5 to 10 at a moderate loss of light intensity (e.g. 30 or 40%). In case of a smaller image according to FIG. 15B the luminous power amounts to only one fifth compared to FIG. 15A, whereas the stability can increase by a factor of 30 or more. The condition for this gain in stability is the utilization of an extremely high stabilized lamp power supply, since the stability gain obtained by optical means would be masked by the instability of the power supply otherwise.

Finally, FIGS. 15E and 15F show a circular monochromator exit slit $\overline{SO}$ which is needed with several microcells (cf. FIG. 33, also FIG. 26 KJ). The entrance slit is still a rectangular one and may be opened somewhat wider than the exit slit. In this case, too, a gain in stability can be obtained by a rotated image (FIG. 15F) if a mercury lamp is used. This will be seen from FIG. 15G: The image of the monochromator entrance slit on the exit slit is set off in the monochromator perpendicularly to the slit axis and proportionally to the wavelength. In the case of FIG. 15E, and with the small condensor magnification shown, a perpendicular displacement of the light arc gives an insignificant modulation of light at the entrance slit. The real modulation effect occurs at the exit slit. Because of the spectral offset the use of mercury lamps, which give a line spectrum, results in a modulation of intensity as well as of the frequency if adjacent spectral lines are not adequately separated (shifting of curve 15.2 compared to curve 15.1; Δλ denominates the width of the exit slit converted into wavelengths). In FIG. 15F (rotated image) the directions of spectral offset and of lateral lamp positioning are perpendicular to each other. Exact positioning of the lamp and of the wavelength setting to optimum intensity is improved which reduces the influence of arc displacements.

Continuous light sources: The illuminations of FIGS. 15C, D, and F are not always superior to the other illuminations if a continuous light source is used, e.g. a Xenon high-pressure lamp instead of a Mercury one. Let us assume a rectangular entrance slit S and an arc image parallel to the slit axis. The width of the entrance slit may be twice or three times the effective width of the arc image. The exit slit $\overline{S}$ may be either rectangular or circular and have a somewhat smaller slit width. The absorption of the sample is measured in the maximum of the absorption band. Oscillatory displacements of the lamp arc give now at the monochromator output a small frequency modulation, which can mostly be neglected, but only a 2nd order effect in the light intensity. (It can be shown that the wavelength dependent transmission characteristics of the whole instrument can be appropriately levelled, e.g. by tuning the wavelength to a shoulder of the absorption band of the sample.)

This method of optical light flux stabilisation is the most powerful one if the light gathering power of the sample cell (window surface times the square of the numerical aperture) is small compared to the light gathering power of the monochromator. The disadvantage of the Xenon lamps is the lower UV-intensity as compared to Mercury lamps.

In order to cope with the multitude of measuring problems which may occur, it is therefore appropriate to indicate adequate means to obtain an image of the lamp axis either parallel or perpendicular to the axis of the slit, and to vary the condensor magnification according to the time range of interest.

In conventional monochromators the slit arrangement is vertical. Operating high-pressure lamps requires, almost without exception, the vertical position, too. For high stability operation this is even obligatory. Smaller monochromators can be mounted in a position rotated by 90° around their axis. In the case of larger high-intensity monochromators this procedure is complicated and may affect the mechanical stability. Therefore, it might be appropriate to construct a special high-intensity monochromator with horizontally arranged slits. However, in a reaction kinetic apparatus designed for universal applications the vertical slit position is more important than the horizontal one. The horizontal position may be preferred with field-jump cells where the distance between the electrodes has to be as small as possible, as well as for sample cells with a flat cell chamber K according to FIG. 22. Cells with circular window apertures, as in FIGS. 28 and 33 and also in the cross section of FIG. 5A, will be insensitive to the slit position. But for a sample cell of FIG. 23 with a cell chamber KC the vertical position is the better one. The vertical slit is almost obligatory for microchemical sample cells of FIGS. 25, 34, and following with capillary cell chambers according to FIG. 26. A monochromator with horizontal slits would then require an additional device for rotating the light beam behind the monochromator.

Following up the statements in the preceding paragraph, it is more adequate to provide a device for rotating the image of the light source in front of the monochromator. The possibility to work with a non-rotated image should not be excluded. In a special version of a commercial spectrophotometer the rotation is performed by means of an asymmetric ellipsoidal condensor mirror together with a plane deflection mirror. This arrangement does not allow to change the image ratio or orientation. Furthermore, the system is very costly and easily damaged if a high-pressure lamp explodes. The arrangement shown in FIG. 16A fulfills the same requirements with less complicated means, and in case of damage only a conventional condensor lens has to be replaced. The condensor lens L5 or a combination of such lenses is arranged as usual. A deflection mirror R6 guides the light into the vertical axis where a second deflection mirror R7 directs the light onto the monochromator entrance slit S. This double deflection into a horizontal axis, which subtends an angle of 90° with the condensor axis, rotates the image of the light source Q by 90°. The field lens L9 is not shown for the sake of a clear representation. In order to minimize the number of reflections a monochromator without internal deflection mirrors is recommended (e.g. similar to FIG. 1). Fused silica prisms with reflective coatings as 2nd surface mirrors are preferred because they have low absorption and withstand high light intensities. An appropriate version is shown in FIG. 16B where a double prism, specified as the reversion prism PRA, is derived from a combination of two simple deflection prisms with an entrance plane 16.1, two hypotenuse planes 16.2 and 16.4 with reflecting backsides, and an exit plane 16.5. FIG. 16C shows a modified reversion prism PRB which is a combination of the prism PRA with a rhomb. The rhomb adds two further deflections in order to have the incoming light beam in the same plane as the outgoing light beam. Therefore, the prism combination PRA can be easily replaced by a single deflection prism for switching from a rotated to an unrotated image and reverse.

FIG. 17A shows a combined prism PRC which rotates the image in a straight undeflected lightpath. Preferably two optically contacted prisms are used: one larger 30°-prism 17.1, from which the corners 17.1a and 17.1b are cut off, and an equilateral prism 17.2, from which the corner 17.2 is cut off. The planes 17.3 and 17.6 subtend an angle of 30° with the main axis. Other shapes and prism angles can be used, too. The incoming light is totally reflected by the plane 17.3, reflected by the plane 17.4, which has a reflective coating, passes the contact plane 17.5, and is again reflected by the plane 17.6 back to the orignal lightpath. If this arrangement is oriented vertically, the image is reversed. A rotation of 45° around the axis rotates the image by 90°. The prism can be mounted so that it can be rotated around its main axis, in order to obtain an image of the light source Q which may be parallel or perpendicular to the slits S. The prism can also be removed from the light path without changing the focal points of the optical system, if fused silica with a refractive index of $n = 1.5$ is used.

FIG. 17B is a simpler reversion prism PRD according to Amici. The entrance plane 17.11 and the exit plane 17.13 subtend equal angles $\alpha$ with the main axis. The incoming light is refracted by an angle $\beta$, totally reflected at the basis plane 17.12, passes the exit plane, and returns to the light path with its original angle. The prism is rotated by 45° around its main axis in order to rotate the image by 90°. This prism has to be used in a parallel or quasi-Parallel light path.

The prisms PRC and PRD can also be used in the primary light path of the sample cell unit EZ, in order to image a vertical monochromator exit slit $\overline{S}$ horizontally into the sample cell, or reverse.

For changing the image ratio of the light source onto the entrance slit S, one could use a given condensor lens system and vary both the distances of the light source and of the image. This, however, involves accurate readjustments of the distances and of the lamp position. One could also provide a set of plugin condensor tubes with different lenses L5 or lens combinations L5, L6, which have adjusted distances. A maore adequate arrangement is shown in FIGS. 18A and B. A double-lens system L5, L6 and a single lens L7 with mountings 18.1 and 18.2 are arranged on a sliding or revolving plate and can be switched arbitrarily into the lightpath. The revolving plate consists of a plate 18.0 and a rotating axis 18.4 with a lever 18.5, a spring 18.6 and stop positions 18.7. The distances of the lenses L5, L6, and L7 from the light source Q and from the entrance slit S are chosen such that for an average wavelength of, e. g., $\lambda = 300$ nm or 350 nm no correction of the distance between light source and entrance slit is necessary when the condensor is changed. A condensor aperture diaphragm 18.3 in the lightpath of the lenses L5 and L6 corresponds to the mounting 18.2 of the lens L7 with respect to its distance from the field lens L9. Alternatively, a fixed aperture diaphragm can be arranged closely to the right hand side of the revolving plate. Thus the illumination of the monochromator aperture remains unchanged, too. The mounting 18.2 of the lens L7 is provided with an adjustment device, which consists of two screws 18.2a and of a compression spring 18.2b with a pin, which is opposite to the screws 18.2a. Once the lens L7 has been adjusted there is no disalignment of the condensor optics when switching the lenses. Thus the optimal condensor magnification can be found easily during measurements, without impediment by a lamp house which is too hot for making more complicated manipulations.

FIG. 18C shows a combination of the two arrangements shown in FIGS. 17B, 18A, and 18B. Since the prism PRD has to be used in a collimated lightpath, the condensor is provided with an additional lens L8. The field lens L9 images the mounting of the lens L8 onto the grating (or prism) of the monochromator. If the focal length of L8 is appropriate, the lens L8 can also serve as the field lens, and the lens L9 is omitted. The prism PRD is mounted in a rotating tube, so that the horizontal or the vertical image of the light source Q onto the slit S can be arbitrarily set by turning a lever. A version of the system according to FIG. 18C is equipped with lenses of the following focal distances: L5, L6, and L7 plane-convex lenses $f = 50$ mm, L8 plane-convex lens $f = 75$ mm, and L9 bi-convex lens $f = 50$ mm at 10 mm in front of slit S. For a third image ratio, another lens L7 of, e. g., 100 mm can be provided or the lens L8 may be interchanged with a plug-in tube, too.

Condensor arrangements for obtaining a stable light flux of high intensity without rotating the light beam around its axis are shown in FIG. 19. Instead of sperical lenses, a combination of cylindrical lenses LZ5, LZ6, and LZ7 (FIG. 19A), or a combination of cylindrical and spherical lenses is used (FIG. 19B: LZ5, L6, LZ7; FIG. 19C: LZ5, LZ6, LZ7 with L8 or L8A). Broken lines in FIG. 19C give rays and lens shapes in a plane perpendicular to the lamp axis. These combinations give an anamorphotic image of the light source Q onto the slit S, where the enlargement in the direction of the lamp axis is considerably larger than in the direction perpendicular to the lamp axis (e. g. image ratios of 3:1 and 1:1, respectively). Following the aforementioned statements, movements of the arc perpendicular to the axis have reduced effect, too, and the highly unstable regions around the anode can be easily excluded in the image at the monochromator entrance or exit. These arrangements are useful both for lamps having line spectra and continuous spectra. The image ratio onto the monochromator entrance slit S can be changed, too, by interchanging spherical lenses in the right hand part of the condensor system, e.g. the lenses L8 and L8A in FIG. 19C. These lenses may be mounted in a rotary device or in preadjusted plug-in tubes. (The same device could also be used instead of or together with with FIG. 18A.) Sphero-cylindrical lenses could be used instead of separate lenses LZ7, L8, and L8A, too. - Special attention has been paid for the correct illumination of the monochromator grating (or prism) by the field lens L9. This field lens is not shown in FIG. 19A. In FIG. 19B, the lens L9 images the top and the bottom sides of the lens mounting of L6 onto the grating. In the direction perpendicular to the lamp axis, however, an additional aperture diaphragm SA is provided with respect to the refractive power of the cylindrical lens LZ7. In the upper arrangement of FIG. 19C, the mounting of the lens LZ7 may be imaged onto the grating for sake of simplicity (rays in thin lines). If the lens L8 is replaced by a lens L8A of shorter focal length, an additional smaller aperture diaphragm SA must be provided at the left hand side of L8A (lower arrangement, partial). This additional aperture diaphragm is switched into the light path together with the lens L8A. A special field lens L9 could also be omitted if the lenses L8 and L8A have appropriate larger distances from the left hand part of the condensor system and act as combined condensor and field lenses. The light path must then be slightly convergent behind the lens LZ7. - FIG. 19D shows an anamorphotic mirror system where the mirror RZ5 is a 1st or 2nd surface mirror the profile of which has the shape of an elliptical or circular cylinder. The axis of curvature is perpendicular to the lamp axis. Due to its relatively small width this mirror can be easily mounted near to the lamp, and may be made of stainless steel coated with aluminum. A cylindrical lens LZ7 of a larger focal length, with its axis parallel to the lamp axis, completes the imaging system. The image ratio onto the entrance slit S may be changed and reduced by inserting an additional spherical lens closely to the right hand side of the lens LZ7 (or by replacing the lens LZ7 by an appropriate sphero-cylindrical lens), by reducing the distance to the slit S, and changing the field lens L9. The cylindrical lens LZ7 could also be replaced by a second cylindrical mirror. Instead of cylindrical mirrors, non-spheroidal elliptical mirrors could be used, too, which, however, may be more costly.

Arrangements as described above, in combination with the interchangeable lens L1 in front of the sample cell, give in the shorttime range high luminous densities which exploit the light gathering powers of the monochromator and the sample cell as far as possible. For measurements in the long-time range, where the light flux stability becomes more important, the light gathering powers are exploited only to an extent that arc movements have minimal effect.

LATERAL LIMITATION OF PRIMARY LIGHT BEAM

Certain microcells, e.g. of FIG. 33, have a smaller light gathering power than the monochromator. The image parameters in the primary light path must then be selected according to the sample cell. In particular, the lateral limitation of the light beam must be achieved already before the beam splitter and not in the sample cell. Otherwise the reference light beam would not correspond to the light beam which passes through the sample cell, and the compensation of the remaining light flux instabilities by the reference detector D1 would become even more difficult. This condition has been neglected or incompletely fulfilled with many conventional instruments but it is a very strong one with the new apparatus.

A frequently used method of the lateral limitation of the light beam is to select the hight and the width of the monochromator exit slit according to the cell dimensions and to the image ratio of the exit slit onto the cell. This method has been found to be insufficient because of the high aperture ratio of the primary light beam and the very different designs of cells used with the new apparatus. A more appropriate arrangement which limits the light beam at both sides of the monochromator exit slit $\overline{S}$ is shown in FIG. 20. According to FIG. 20A two radiant field diaphragms S1 and S2 are arranged in front of and behind the slit $\overline{S}$. The lenses L0 and L1 image these radiant field diaphragms onto the cell chamber K so that the images S1' and S2' of the diaphragms are slightly smaller than the entrance and exit apertures of the sample cell. Rectangular or circular diaphragm apertures are used according to the cell apertures. The image S2' may be even slightly smaller than S1' in order to overcome slight deflections of light rays due to small inhomogeneities of the sample solution that may occur in some experiments. In the case of fluorescence and scattered light measurements the radiant field diaphragms serve also as stray light diaphragms.

If the images S1' and S2' are in symmetrical positions to the cell, the radiant field diaphragms S1 and S2 will generally have neither the same aperture surface nor the same distance from the exit slit $\overline{S}$. Identical dimensions which simplify manufacturing and alignment are obtained if the distance of the lenses L0 and L1 is equal to the sum of the focal lengths $f_o + f_1$ which gives a lateral image ratio $v = f_1/f_o$ which is independent on the distance of the diaphragms and the images from the focal points of the lenses L0 and L1, respectively. The longitudinal image ratio becomes also independent and is $1/v^2$ in air and $n/v^2$ in a medium of a refractive index $n$ (water: $n = 1,33$). Therefore, in the case of circular diaphragm apertures of equal radii $r$ at a distance $d$ and useful cell apertures of equal radii $r'$ at a distance $d_n'$ between the apertures:

$$r' = v \cdot r,$$

$$d_n' = (n/v^2) \cdot d$$

$$(v = f_1/f_o)$$

where the light gathering power L of the cell is $$L = \pi^2 \cdot r^4/d^2 = n^2 \cdot \pi^2 \cdot r'^4/d_n'^2$$

The lenses L0 and L1 may be spaced at a distance which is approximately equal to or somewhat larger than the sum of the focal lengths $f_o + f_1$, where the latter case gives an image S2' somewhat smaller than S1'. In any case (also with more closely spaced lenses) the light gathering power defined by the size and the distance of the diaphragms S1 and S2 must be equal to or smaller than the maximal light gathering power of the respective sample cell. With microcells, the exit slit $\overline{S}$ may be even omitted which gives the maximal light flux through the cell with a given luminous density in the exit slit plane. On the other hand, the diaphragms of FIG. 20 reduce also the possible errors introduced by focal differences in the optical system. They may be used, e.g. for obtaining a quasi-achromatic light beam in the cell and onto the cathodes of the photodetectors D1 and D2 if the distance $d$ and thus the distance $d_n'$ are somewhat larger than needed for a given cell chamber K. It is appropriate to admit focal differences of up to ±2 mm in the sample cell at least for standard cells, where the windows may have inner diameters or widths of about 6 mm and a distance of, e.g., $d_n' = 7$ mm.

Generally the interior of the monochromator is not easily accessible. Thus it would be adequate to install a whole series of round and rectangular radiant field diaphragms S1 and S2 on a revolving device in order to switch these diaphragms in pairs. Variable circular and rectangular irises could also be provided. FIG. 20B shows a simpler arrangement, using a monochromator where the exit slit $\overline{S}$ can be interchanged by plug-in diaphragms 20.1 in a mounting device 20.0. The bore of the mounting device is slightly larger than usual. This bore fits a plug-in tube 20.2 with an oblong hole 20.3, which is perpendicular to the axis of the tube in order to insert the slit diaphragm 20.1, and with the two radiant field diaphragms 20.4 and 20.5 on both sides of the slit diaphragm 20.1. One special plug-in tube each with fixed radiant field diaphragms is provided for each sample cell which has an optical geometry that differs from other cells or which is used with a different set of lenses L0 and L1.

A simplified though less efficient lateral limitation of the light beam is obtained by interchanging the exit slit $\overline{S}$ (rectangular and round exit diaphragms), together with replaceable fixed aperture diaphragms in front of the beam splitter T, e.g. in the place of the filter holder HF1. Instead of fixed aperture and fixed slit diaphragms, adjustable circular and rectangular iris diaphragms may be used, too.

ILLUMINATION OF PHOTOCATHODES

The photodetectors D1 and D2 in the primary and in the reference lightpaths must have a high cathode current capability. This is very important in dynode switching photomultiplier circuits used with the new apparatus. The highest cathode currents are obtained with photomultipliers which have inner photocathodes on a metal substrate, e.g. with the type 1P28 of RCA and equivalent phototubes, where the effective cathode area is approximately 5 × 15 mm. Thus the standard method of illumination is to image the monochromator exit slit $\overline{S}$ onto the photocathodes. This, however, leads to non uniform wearing of the cathodes due to the high light intensities and results in an irregular sensitivity profile which is equivalent to a blurred, smeared and irregular lateral limitation of the light beam. This effect is extreme if the light is too sharply focussed onto the photocathodes and affects also the stability of the apparatus, especially if the inequalities of the cathode sensitivities are transverse to the axis of the lamp image.

An improved set-up for illuminating small rectangular photocathodes is shown in FIGS. 21A and B. For easier representation the photodetector D1 is shown without the beam splitter T. The arrangements of FIGS. 21A and B are provided for set-ups where the axis of the lamp image is perpendicular or parallel to the slit axis, respectively. Both arrangements use a cylindrical lens $\overline{LZ1}$ instead of a spherical lens $\overline{L1}$ of FIG. 2. The distance between the photocathode and the lens L0 should be approximately equal to the focal length $f_o$ of the lens L0. The distance between the photocathode and the cylindrical lens $\overline{LZ1}$ equals the focal length $f_1$ of the lens $\overline{LZ1}$ which is smaller than $f_o$. The cylindrical axis of $\overline{LZ1}$ is parallel to the longitudinal axis of the photocathode which is perpendicularly arranged to the axis of the lamp image. Thus the monochromator aperture (grating or prism) is imaged onto the photocathode transverse to the lamp axis in the longitudinal direction of the cathode, whereas the exit slit plane and thus the light source are imaged in the other direction and give a smaller image (which is proportional to the slit width in FIG. 21A and proportional to the slit height in FIG. 21B). Arc wandering transverse to the lamp axis has now very small effect on the photocurrent even if the sensitivity profile of the photocathode is an irregular one. Moreover, the cathode is more uniformly illuminated than with a spherical lens $\overline{L1}$ and burn-out effects are highly reduced. Due to the fact that both achievements favour each other, a considerable improvement is also obtained if the distance between the lens L0 and the photocathode is somewhat larger than the focal length $f_o$ with respect to constructional reasons. A corresponding set-up is used with the photodetector D2 behind the cell, i.e. the collecting lens L2 is moved towards the cell, or replaced by a spherical lens of longer focal length and followd by a cylindrical lens the axis of which is parallel to the photocathode axis, or replaced by a corresponding sphero-cylindrical lens.

The arrangement of FIG. 21A where the image of the lamp arc is rotated by 90° with respect to the slits S and $\overline{S}$ is still superior to FIG. 21B because a hundred percent compensation of light flux instabilities by the reference photodetector D1 alone is practically impossible. Small alignment errors of lenses, diaphragms and photocathodes and even small linearity errors of photomultipliers must be taken into account. Any set-up that improves the signal stability without reducing the primary light intensity will be also useful for using stronger lamps and/or larger condensor imaging ratios in order to obtain a higher light intensity without degrading the stability.

SAMPLE CELL CHAMBERS AND SAMPLE CELLS

An important means for constructing sample cells for kinetic studies with different parameters of perturbation, but similar optical observation of the time course of the reaction, is obtained by using uniform or similar sample cell chambers the shape of which depends mainly on the available sample volume and less on the applied parameter of perturbation. The design of such a cell chamber, especially for standard sample cells with a chamber volume of the order of 1 cm$^3$, is described in FIGS. 22A and B, which show two alternative versions KA and KB. The cell chamber is made of four planeparallel plates of, say, fused silica, or other glassy material with wide-band transmission characteristics. In case of the cell chamber KA the plates are rectangular. For measurements of fluorescent and scattered light the smaller plates 22.1 are preferred as the cell windows in the primary lightpath and the larger plates 22.2 as the cell windows in the secondary lightpath. The cell KB is constructed of four trapezoidal plates 22.4 cut with angles of, say, 45°. In both cases the plane-parallel plates are sealed (cemented or fused) together so that light-tight black layers 22.3 and 22.5, respectively, separate the lightpaths and avoid light pipe effects between adjacent plates. In case of the cell KA also the front planes 22.2a of the plates 22.2 should have an opaque coating, e.g. a black glazing.

FIG. 22C is a device which is preferred for mounting the sample chambers KA or KB into sample cells of the type C (FIG. 9). The cell chamber is clamped, after insertion of sealing elements 22.6, between two mounting pieces 22.7 and 22.8. The sealing elements are made of chemically inert rubber or plastified plastic material or of PTFE or similar. The mounting pieces may be shaped as truncated pyramids and are fixed by four rods or screws or by an outer shell 22.10 with a mounting ring 22.11 with a thread 22.11a. The detailed construction of the mounting pieces 22.7 and 22.8 depends on the parameter of perturbation and will be discussed in several examples. The cylindric shell 22.10, which is part of the center part 9.3 of the cell, has four window bores 9.7 which are opposite to each other. These bores can have threads or sockets for mounting additional optical elements such as lenses very closely to the sample chamber, in order to make full use of the high aperture for the light beams which can be achieved with the shown arrangement. Furthermore, the sample cell may be equipped with the box-type body 9.4 with an alignment pin 22.12 on its bottom side which fits into the slot 6.21 of the cell holder HZ shown in FIG. 6.

In case of cells of the types A and B (FIGS. 7 and 8) the cell chamber is mounted more directly into the cell body 7.3 or 8.3, respectively, but the mountings of FIG. 22C can also be used with these cells, and reverse.

TEMPERATURE- AND FIELD-JUMP CELLS

Sample cells designed for kinetic studies where the initial non-equilibrium state is induced by a high-voltage pulse are shown in FIGS. 23, 24, and 25. The parameter of perturbation may be either the electric field itself or the increase of temperature, which appears in electrically conducting solutions during the application of the high-voltage pulse. Generally the same cells can be sed both for the temperature- and the field-jump method. In special field-jump cells, however, the distance of the electrodes is somewhat reduced as compared to temperature-jump cells in order to obtain a higher electric field strength.

FIG. 23 shows a temperature-jump cell with an improved cell chamber KC. This cell chamber KC is almost cubic with ground hollow half-spheres 23.1 on its upper and lower sides, which fit the grounded upper electrode 23.2 and the lower high-voltage electrode 23.4. The cell chamber KC is mounted into the insulating cell body 7.3 with rubber-elastic sealing rings 22.6 by means of a threaded ring 23.8, which is locked to the cell body 7.3 by threaded pins (not shown). The electrodes 23.2 and 23.4 are preferably made from disks of noble metal (gold or platinum) soldered onto electrode rods 23.12 and 23.13, respectively, and rounded off as calottes. The lower electrode rod 23.13 and a profiled insulator 23.14 form a male high-voltage connector 7.11 which fits the female connector 5.14 and 5.15 of the cell holder HZ shown in FIG. 5. The upper electrode rod 23.12 has a very close electric and thermal contact to the cell cover 7.4. The handle 7.5 is a screw with a hole 7.6 that accepts the thermometer probe 7.1 of FIG. 7. The sample cell can be filled by removing the upper electrode and the cover from a thread 23.2a. The rod 23.12 is surrounded by a plastic piece 23.9 with a ventilation hole 23.9a through which a chemically inert gas, such as nitrogen, can be applied, too.

Two window bores 7.7a in the primary lightpath have smaller cross sections than two window bores 7.7b in the secondary lightpath, where plane-convex lenses 23.3 are mounted at the outer sides of the plane-parallel plates 22.1. These lenses, together with the lenses L3 and L4 in the cell holder, form powerful optical systems with numerical apertures of approximately 0.75 each. The cross section of the chamber 22.0 amounts to, e.g., 7 × 7 mm. The cavity between the lower electrode 23.4 and the lower half-sphere 23.1 is sealed with a rubber-elastic ring or sealing compound 23.5 which serves as a shock-absorber for shock-waves that occur due to thermal expansion of the sample solution during the temperature-jump. The cavities between the outer sides of the cell chamber KC and the cell body 7.3 are filled with an insulating sealing compound (e.g. silicone rubber), especially the cavities 23.6 around the lenses 23.3 and the mounting rings 23.7.

FIG. 24 is another temperature-jump cell which is also designed for field-jump measurements. The sample chamber KA with the windows 22.4 forms a cubic channel between axial cylinder bores 24.10 and 24.11 of the two mounting pieces 22.7 and 22.8. These bores are semi-spherically tapered versus the sample chamber. The inner edges of the windows 22.4 are slightly inclined to match the mounting pieces. Flattened semispherical metal electrodes 23.2 and 23.4 have been inserted into each of the bores 24.10 and 24.11. The lower electrode 23.4 is fixed to an insulator 24.14 by a screw-bolt 24.13 which form both the high-voltage connector 7.11. The insulator 23.14 is fastened to the lower side of the metal shell 22.10 by a thread 22.11a. The beforementioned threaded ring 22.11 is screwed into the same thread 22.11a. The upper electrode 23.2 is screwed to the pin 24.1 which has an axial bore and is connected to the metal end plate 24.2. The axial bore 7.6 accepts a temperature probe. The end plate 24.2 should have good thermal and electric contact with the square metal piece 9.4, since the thermostatting of the sample has to be effected from the sample cell holder HZ via the metal shell 22.10, via its square part 9.4, via the end plate 24.2, via the pin 24.1, and via the upper electrode 23.2. The electrical connection of the upper electrode with the grounded outer conductor 5.13 of the coaxial high-voltage connector in the cell holder has to be established via the same way. Therefore, the end plate 24.2 is constructed as a flat cylinder with spreading sectors which are separated by radial slits (not shown) in the end plate. At their outer circumference the sectors have a conical cross section 24.3. By means of a cone 24.4 with a thread 24.5 the end plate can be clamped into the metal piece 9.4. The upper electrode chamber 24.10 is sealed by a piece of plastic material 24.6 and a sealing O-ring 24.7 which is fixed on the connecting pin 24.1 between the end plate 24.2 and the electrode 23.2. The square metal piece 9.4 is provided with one or several channels 24.8 which are lined with a layer of chemically resistant glass or plastic material and which may each be closed by means of stop-cocks 24.9. Via these channels the cell may be rinsed continuously with inert gas, e.g. nitrogen or argon, so that sensitive samples, e.g. which oxidize quickly, may be investigated in the absence of air. FIG. 25 shows a temperature-jump cell for very small sample volumes, which in its outer dimensions corresponds to the cell of FIG. 23. The deflected vertical cross section gives half the absorption and half the emission lightpath. As the cell chamber the chamber KG of FIG. 26 is preferred but other chambers shown in FIG. 26 can also be inserted. The sample volume is 20 to 500 microliters and may be varied by interchanging the cell chamber which is held in a insulating body 7.3 by a mounting piece 25.6 (e.g. of fluorine plastic material known as "KEL-F"). A sealing disk 25.13 on the top and a sealing ring 25.9 on the bottom side are preferably made of PTFE ("Teflon"). Due to its fluidity this material seals the cell chamber against the high voltage electrode 25.10, the upper end of which is either conical or cylindrical (stepwise reduced diameters). In a modified construction the cell chamber is inserted from below after removing the high voltage connector 7.11 together with the electrode 25.10. The window bores in the cell body 7.3 are provided with diaphragm apertures 25.7 and 25.12 directly in front of the cell chamber. The bores 7.7b in the emission lightpath have lenses 25.8 which may also be shaped as conical lenses similar to K3 and K4 of FIG. 5A. Both electrodes 25.5 and 25.10 are overcapped with nobel metal (fine hatching). The grounded upper electrode 25.5 can easily be removed by a bayonet socket which is very useful in titrations. Perfect thermal and electric contact between the cell cover 7.4 and the electrode 25.5 is obtained by a conical bayonet socket 25.1 and 25.2 with a handle 25.3 and a pressure spring 25.4. The parts 25.1 and 25.2 can also be made as a flat or a threaded bayonet socket.

FIG. 26 shows an enlarged representation of various cell chambers which can be inserted in FIG. 25. In the dorsal projection light incidence is shown from the top as indicated by arrows. The cell chamber KD is a capillary tube 26.1 with a cylindrical bore and a cylindrical outer shell and face-ground upper and lower sides, but no special shaping treatment has been applied to the optical surfaces. The usefulness of such a capillary tube is very limited, especially in temperature-jump measurements where the refractive index of the solution changes. The cylinder-lens effect which deflects the passing light beam proves to be very disturbing if accurate measurements of absorption are needed. In measurements of fluorescence the high amount of stray light of this capillary tube KF is also disturbing. Light rays which are not exactly focussed into the center contribute a particularly high amount of stray light. This is shown for three rays a, b, and c which are only one time partially reflected at the outer surface and reach the emission lightpath as the rays a', b', and c' after repeated transmission through boundary surfaces.

The outline of the cell chamber KF is based on a cylinder capillary tube 26.1. Its outer shell has been face-ground such that its cross section has the shape of a square with rounded corners. Test experiments have shown that the face-ground front planes, together with the diaphragm apertures 25.7 and 25.12 in FIG. 25, reduce the stray light already considerably. A further reduction of stray light is achieved by application of a black glazing or a layer of black varnish 26.3 on the outer surface, except for the window apertures in the lightpaths (e.g. the plane 26.2). A further improvement is obtained with the cell chamber KG which, in principle, can be considered as an elongated miniature version of the cell chamber KA in FIG. 22A. Plane-parallel window plates 22.1 and 22.2 are fused or cemented by black intermediate layers 22.3. The corners of the larger plates 22.2 are coated with a black glazing or a black light-absorbing vernish 26.3, similar to the cell chamber KF. In fluorescence measurements the window plates 22.2 are used as the emission windows.

The cell chamber KH has an interior cross section which is shaped as an elongated rectangle. The window plates 22.1 in the primary lightpath and the window plates 22.2 in the secondary lightpath have changed their positions. This cell chamber is used particularly for measurements of absorption with an increased lightpath.

A multitude of variations for this type of cell chambers can be indicated. Cell chambers of the type KF, KG, and KH are especially suited for flow cells and combined flow-temperature-jump cells because of their small sample volume. Another drawing of FIG. 26 is a cell chamber KJ for flow experiments only which has been optimized for combined measurements of absorption and fluorescence. A Z-shaped flowpath 26.4 matches the coaxial inlets and outlets of the other capillary cell chambers and gives an enlarged absorption pathlength together with a reasonable fluorescence efficiency and small sample volume. It may be used, e.g., in the flow cell of FIG. 38 as an alternative to the cell chamber KG. Black filling glass 26.5 is used internally with rounded corners and polished surfaces in order to avoid cavitation. The Z-shape secures fast and complete cleaning from waste reaction mixture when the flow is initiated. The outlet cross section (lower side) may be somewhat smaller than shown in the drawing. Capillary cell chambers with and without rounded corners may be used (cf. also FIGS. 34C and 35D).

PRESSURE-JUMP CELLS

Figure 27:
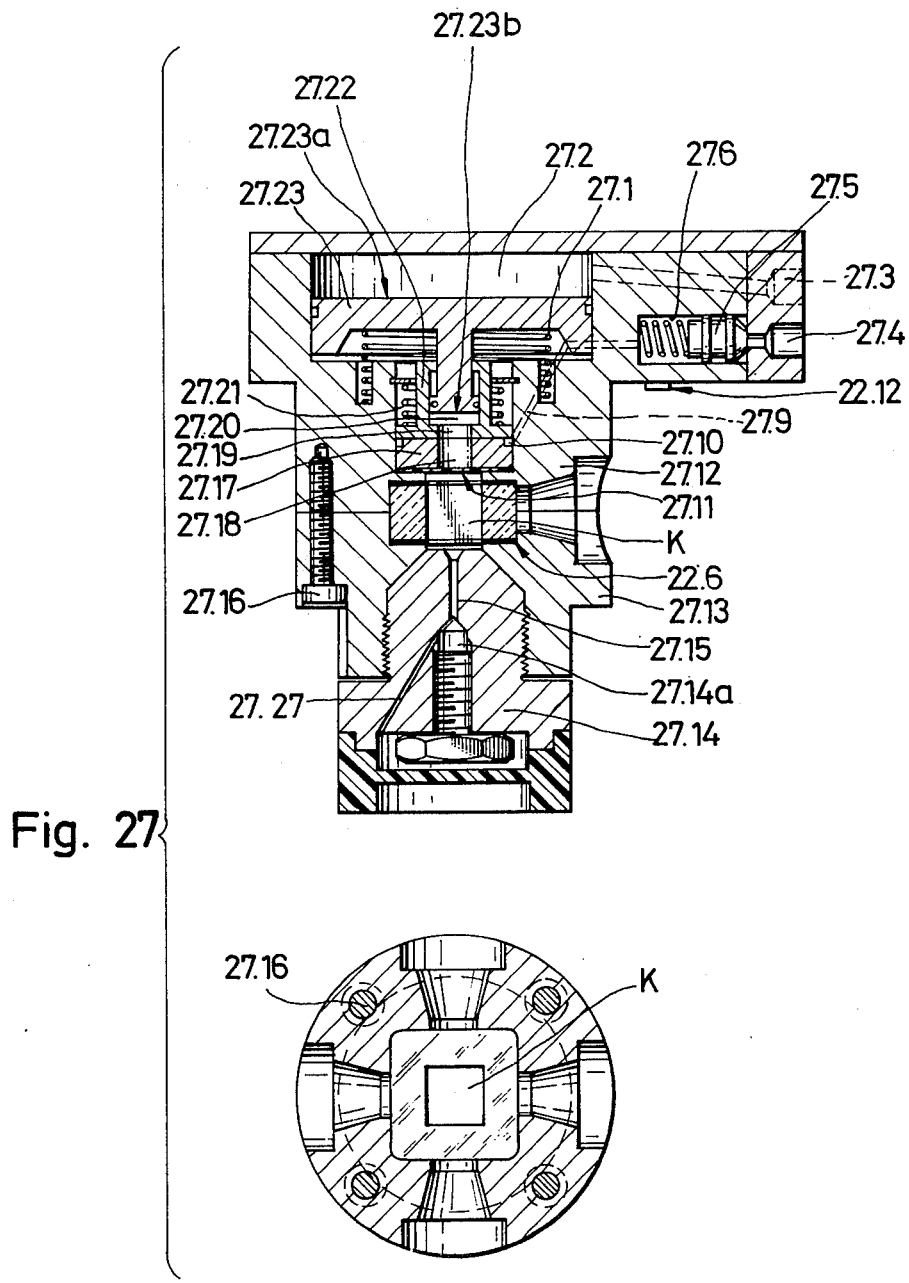

FIG. 27 shows a sample cell where the chemical reaction is induced by a change of the hydrostatic pressure. The cell chamber K corresponds to the versions shown in FIGS. 22A and B. The cell chamber is clamped between mounting pieces 27.12 and 27.13 by means of elastic sealing elements 22.6, thus forming an autoclave chamber. The lower mounting piece 27.13 is provided with a locking device 27.14 which can be removed and which allows to fill the sample solution into the cell chamber if the sample cell is turned upside down. The locking device 27.14 has a channel 27.15 which can be closed by a needle valve 27.14a. When the locking device 27.14 is closed tightly, the exceeding sample solution can flow off through the channel 27.27.

In the upper mounting piece 27.12 the cell chamber K is sealed by a membrane 27.11 (rubber elastic material such as plastified PVC or synthetic rubber). An auxiliary pressure chamber 27.18-20 above the membrane 27.11 contains a liquid of low compressibility, to which a high pressure may be applied by means of a pressure intensifying piston 27.23. The pressure is transmitted to the sample solution via the membrane 27.11. The chamber 27.18-20 is formed by cylindrical bores in two matching parts 27.17 and 27.22. The lower part 27.17 serves as a clamping plate for the membrane 27.11 and is tightly fixed to the upper mounting piece 27.12. The upper part 27.22 is a hollow piston with two bores 27.19 and 27.20, and moving in a larger bore above the clamping plate 27.17. The clamping plate 27.17 and the piston 27.22 have lapped planes which are held together by a pressure spring 27.21. Above the cylindrical bore 27.19 in the hollow piston 27.22 there is an enlarged bore 27.20 into which the pressure intensifying piston 27.23 is inserted. If the pressure is increased at the low-pressure side 27.25 of the pressure intensifying piston 27.23, the piston 27.22 is held down by the spring 27.21 and by the force exerted at the high-pressure side 27.24 on the cross section difference between the two bores 27.19 and 27.20 in the piston 27.22. However, the position of the piston 27.22 is not stable. If it is only slightly lifted from the clamping ring 27.17 by an additional force, the pressure liquid flows immediately into the space between the piston 27.22 and the clamping ring 27.17.

Thus, the volume of the chamber 27.18 is suddenly increased, whereas the force exerted on the membrane 27.11 decreases suddenly.

In order to achieve this sudden lift of the piston 27.22, the outer edge of the clamping plate 27.17 is provided with a circular slot 27.10 which is connected to a cylindrical bore 27.6 via a channel 27.9. This bore has an auxiliary piston 27.5 (instead of which an elastic membrane may be used, too). For actuating the pressure-jump, compressed air is admitted via the control connection 27.4. The auxiliary piston or membrane then compresses the pressure liquid in the channel 27.9, in the bore 27.6 and in the slot 27.10. The pressurized liquid exerts the additional force which lifts the piston 27.22.

The low-pressure side of the intensifying piston 27.23 is located in a pressure chamber 27.2, which can also be supplied with compressed air via a connection 27.3. A recuperating spring 27.1 brings the pressure intensifying piston 27.23 back to its original position when the chamber 27.2 is ventilated. The compressed air connections 27.3 and 27.4 are linked to the excitation unit EP (FIG. 1) for the execution of pressure-jump experiments via removable supply connections. The admission of compressed air is controlled by appropriate electromagnetic valves 1.12 in the excitation unit EP (FIG. 1).

As an alternative to the description above, the compression of the sample in the cell chamber K with subsequent sudden pressure drop may also be achieved without compressed air. The power which is necessary on the low-pressure side of the pressure-intensifying piston can also be exerted by a spring which is stretched by turning a lever crew, whereas the pressure release may also be initiated by conventional mechanical or electromagnetical means in order to obtain the necessary additional force on the hollow piston 27.22 or on the control piston 27.5. Finally, the compressed air connections 27.3 and 27.4 or the corresponding elements for exerting the mechanical forces may be installed at the lower flat side of the upper part of the sample cell so that they are in opposite position to corresponding connections or elements which are mounted in the cell holder HZ, and are thus connected to the excitation unit EP via the latter connections and elements.

Figure 28A:
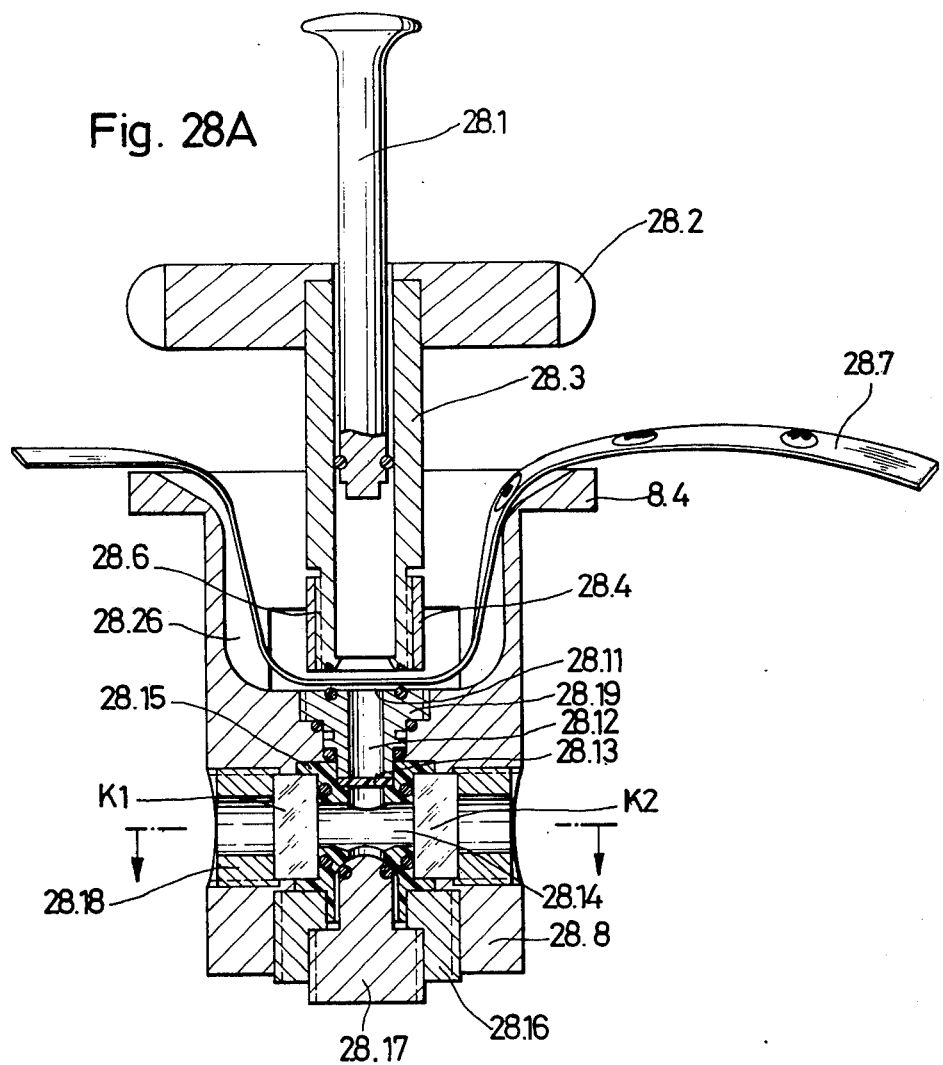
Figure 28B:
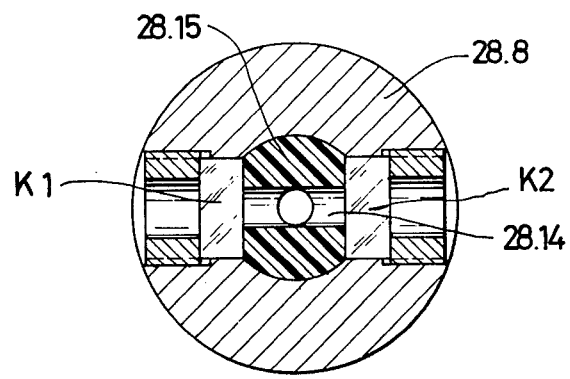

Another pressure-jump cell which may be used with the new apparatus is shown in FIG. 28, using the bursting membrane principle. This cell comprises also an autoclave sample chamber 28.14, an auxiliary pressure chamber 28.12, and an elastic sealing membrane 28.13 between these two chambers. The version shown has been designed for measurements of absorption. FIGS. 28A and B give vertical and transverse cross sections through the light path. FIGS. 28C and D are similar cross sections wherein the cell is rotated by 90° and more details are given with respect to the auxiliary pressure chamber, and the bursting, or rupturable, membrane 28.7, and the corresponding fixation means. (FIG. 28D: bayonet head and socket shown from below). A pressure-jump apparatus of similar design, using the conductometric instead of the optical detection method, has already been described in the application Ser. No. 481817, now U.S. Pat. No. 3,935,727, assigned to the assignee of the present application.

The cell body is of type "B" (FIG. 8), preferably of brass or bronce, and screwed onto the cell holder HZ by a flange 8.4 through holes 8.5. The sample chamber has an inner chamber body 28.15 of chemically inert material, such als polyacetal resin ("Dynal"), PVC, or "KEL-F", tightly inserted or shrinked into the body 28.8, and clamped by a threaded ring 28.16. It can be inserted from below, as shown, but could also be inserted from the upper or from one lateral side. Two disk-shaped windows K1 and K2 are inserted into lathe or cutter borings of the inner chamber body, mounted by threaded rings 28.18 and sealed by O-rings. The liquid sample is applied from below, i.e., the cell is turned upside down, filled, and then closed by a locking device 28.17 (which could also be made with a needle valve such as in FIG. 27). The elastic membrane 28.13 is of rubber elastic material, such as synthetic rubber or plastified PVC, inserted from the upper side, and fixed by a hollow screw 28.19 the bore of which forms the auxiliary pressure chamber 28.12.

The upper opening 28.11 of this pressure chamber can be closed off by the bursting, or rupturable, membrane 28.7. The advantage of the bursting membrane principle, especially when used in optical systems, are the short pressure release time and the very low inertial forces which practically do not cause any mechanical vibrations of the optical set-up which could affect the stability of the light source. The classical disadvantage of this method is the troublesome time-consuming interchange of membranes after each measurement. This disadvantage, however, has been overcome completely by combining an easy-to-release pressure head 28.3 to a strip-shaped membrane 28.8, - a device already described in the aforementioned application. This enables fast sequencing of measurements and application of averaging techniques which, if performed by digital data storage and computing devices, give kinetic data with a much higher degree of accuracy then before.

The principle of this device shall be briefly summarized: The pressure head 28.3 has a bayonet head 28.4 fitting a bayonet socket 28.5 in the cell body 28.8. The bayonet head has a clamping thread, either at its circumference matching a female thread in the bayonet socket, or between the bayonet head and the pressure head itself (thread 28.6). The bayonet socket has a stop in the latter case. Thus, when rotating the hand wheel 28.2, the pressure head is pressed against the membrane 28.7 which closes tightly the opening 28.11 due to a sealing 0-ring. The pressure head is released after rupturing of the membrane, thus releasing the membrane, a short section of which is pulled through in order to place a fresh zone of membrane material above the chamber opening. The hand wheel is tightened again, closing off the pressure chamber anew. Thus at least twenty pressure-jumps may be performed on a single sheet of membrane foil of half a meter length, each part of which is correctly located between the pressure head and the chamber opening, and giving highly reproducible results.

For measurements, after the cell is filled and put into the apparatus, a pressure liquid pump is connected via a flexible pressure hose and an easily removable pressure hose connection (28.23, schematic) to a pressure supply system 28.22, 28.20, and 28.21 leading to the opening 28.11 of the pressure chamber. The bore 28.22 may have a ball valve (not shown). A pressure gauge should be provided with the pump or with the cell. The pressure is smoothly increased until the membrane bursts. With a brass membrane of 0.1 mm thickness, the bursting pressure is up to 150 atm. On the pressure release, a trigger signal is obtained from a pressure transducer 28.9 which is embedded in epoxy on its outer side and sealed with silicon rubber and a membrane 28.10 on its inner side.

The measuring signal obtained from the photodetector D2 will then be recorded by an oscilloscope or a digital storage device.

In order to obtain a short pressure release time of, say, 50 μs, the length of the pressure chamber 28.12 is made as short as possible, whereas the distance between the cell chamber windows K1 and K2 may be up to 20 mm in order to obtain a reasonable amplitude with weakly absorbing samples. Larger distances may be admitted if a longer pressure release time is satisfactory. Briefly, a short distance between the opening 28.11 and the optical axis is needed. With the present construction (where the drawing gives an enlarged length of the auxiliary pressure chamber), this has been achieved by a tub-like gap 28.26 gently guiding the membrane foil which dips deeply into the cell body. Thus the external dimensions of the cell of Type "B" used in a cell holder Hz of FIG. 5 can be easily matched. A small suction pump connected to the gap 28.26 removes exceeding pressure fluid (not shown).

As to the pressure fluid, water has been found to be more appropriate than organic liquids such as oils because of two reasons. First, vapors of many organic substances form deposites on UV transmitting and -reflecting optics, especially at high UV-intensities used with the apparatus. Next, adiabatic heating due to the applied pressure is approximately ten times less than with many other liquids. Thus, thermal stability is increased. On the other hand, using water favours bubble formation at least in the pressure supply system, which could involve difficulties very similar to cavitation during the pressure jump. This difficulty has been overcome by providing the pressure supply outlet very close to the rupturing membrane itself, which, in the present construction, has been achieved by connecting the supply bore 28.22 first to an annular slot 28.20 at the outer circumference of the hollow screw 28.19, then leading upward through a slim bore 28.21 to the opening 28.11.

Furthermore, the pressure head 28.3 has been made hollow with a movable piston 28.1 which forms a simple vacuum pump. O-rings are used for sealing. Before tightening the hand wheel 28.2, the piston is pressed down facing the membrane with a very small gap. After the hand wheel and thus the pressure head are closed up, the piston is drawn back and clamped in its upper position. The pressure above the membrane thus reduced is of the order of 5 mbars. This effectively reduces acoustic noise and pressure wave interferences in the cell chamber 28.14 when the membrane is ruptured. Improvements: Precision measurements yielding informations on amplitudes and time constants of the studied chemical reactions can be improved by using a calibrated pressure transducer 28.9 and recording both the photodetector and the pressure transducer signals digitally, further feeding them to a digital computer. The contribution of the applied pressure pulse function to the measured data can then be eliminated by the inverse convolution technique.

A temperature sensing probe 28.25 is provided for convenience which measures the stationary temperature in the cell body. A fast temperature probe could also be provided in the cell chamber 28.14, e.g. mounted in the locking device 28.17 when studying chemical systems in organic solvents where adiabatic heating is significant. In some cases, an additional information could also be obtained by providing a locking device with a pair of platinum electrodes for measuring conductivity. (A set of electrodes is needed for covering different ranges of conductivities; the electrodes must also be spaced by melting them into a glass body). E.g., if the chemical reaction itself gives no change in conductivity there is still a pressure dependent change in conductivity, at least when adding some neutral salts. The change in conductivity, measured by means of an RF-bridge, may then be used as a very fast pressure probe in the sample, and fed to a digital data evaluation system.

PRESSURE-JUMP CELLS FOR FLUORESCENCE MEASUREMENTS

In FIG. 27, some problems may be involved with respect to the mechanical stability of the sample cell chamber K. Cell chambers of type KA and KB of FIG. 22 should withstand pressures of up to 200 atmospheres if fused perfectly without internal tensions and mounted correctly by the mounting pieces 27.12 and 27.13. From the manufacturing point of view, there may be some limitations especially when using fused silica. Therefore, if fluorescence measurements are not needed, the pressure-jump cell of FIG. 27 may also be constructed with disk-shaped windows K1 and K2, such as in FIG. 28.

On the other hand, pressure-jump measurements using fluorescence detection are very interesting in biochemical studies where the amount of substances is often limited. An improved sample cell chamber KP, which withstands to pressures up to 1000 atm. and which could also be used in shock-tube arrangements, is shown in FIG. 29. It may be used both with the cells of FIGS. 27 and 28 though the construction will be explained as a modified version of FIG. 27. In FIG. 29 the chamber KP is formed by a circular disk of fused silica, sapphire or equivalent material. It should have a rectangular inner bore with slightly rounded edges and a slight flat grinding 26.2 in the primary light path. Furthermore, a black glazing or a light-absorbing layer of varnish 26.3 should be applied to the cylindrical outer surface, except for the entrance (arrow) and exit apertures (emission exits 29.2). The edges 29.3 of the outer circumference are inclined by approximately 45°. The mounting into the cell body is shown in a vertical cross section. Contrary to FIG. 27, the cell has no individual mounting parts 27.12 and 27.13, which parts are now made as one unit. Instead of, the cell chamber KP is scewed into the cell body by a threaded part 29.5 and a mounting plate 29.4, which form also a modified inlet locking device together with the screw 27.14a. At the edges of the cell chamber KP conical sealing rings 29.1 are provided which fit the conical grindings 29.3 and exert an initial mechanical tension on the chamber KP opposite to the stresses that occur during the pressure-jump. The sealing rings 29.1 should either be made of relatively hard plastic material, such as hard PVC, or of a soft metal, such as lead. For liquid sealing, however, relatively soft elastic sealing disks 22.6, such as of plastified PVC, synthetic rubber or teflon are used, with no gap to the sealing rings 29.1 (enlarged detail). The hydrostatic compressibility of these materials corresponds almost to water. Thus, at high pressure strain, this soft elastic material fills the space between the upper and lower surfaces of the chamber body KP and the parts 27.12 and 29.4 completely, and the cell will be perfectly sealed. In a preferred version, the upper sealing disk 22.6 may be a closed disk in order to act as the elastic sealing membrane 27.11, too. Filling of the cell is performed as before by removing the valve screw 27.14a.

Parts 29.4 and 29.5 are sealed by a burried O-ring, so exceeding sample solution may be drained off through an oblique channel 27.27.

In FIG. 29 the optical efficiency of the cylindrically curved emission apertures 29.2 may further be improved by attaching lenses to the cell body similar to FIG. 25. Another approach to obtain a high light collecting efficiency in the secondary light path is shown in FIG. 30A, where three or four individual cell windows are used. Wide angle cones such as K3 and K4 of FIG. 5A may be used with pressurized cells, if their profile is modified to withstand high strain. Instead of this, cylindrical windows with reflective walls are used as light-pipe windows KL3 and KL4, e.g. of fused silica, or of sapphire with respect to its high refractive power and high mechanical strength. Coated and uncoated light-pipes may be used, which will be discussed below.

Light-pipe windows in the exit of the absorption light path of a temperature-jump cell are known in order to improve electric screening. (Rev. Sci. Instr. 42, 1643 (1971)). However, when using a light-pipe window as the emission window of a fluorescence cell, it offers the advantage of collecting any light that enters its entrance within the critical angle of the light-pipe. The light then emits from the exit within a cone, and may be collected by a lens or a lens system LL3, and directed onto the emission photodetector D3 (D4). The conditions for imaging the exit onto the photocathode surface will be very similar to the imaging conditions in a system of FIG. 2, where the entrance surface of the cone K3 (K4) or a plane near to this entrance surface is imaged onto the cathode. However, if the photocathode is near to the exit of the light-pipe, the lens system can be also omitted or replaced by a single lens of smaller refractive power. According to FIG. 30A, the light-pipe windows KL3 and KL4 are sealed to the sample chamber 28.14 by conical sealing elements 30.1, e.g. of Telon, which have a short cylindrical shaft and are pressed into conically tapered bores of the cell body 28.8 (or 28.15) by cylindrically relieved threaded mounting rings 30.2. The conical angle is a very sharp one, e.g., 20° with respect to the axis. In order to withstand high pressure, the windows are held in position by small conical tapers at the outsides of the windows and the mounting rings. The taper angle may be 45° in this place. Small O-rings of Teflon or lead may be inserted to reduce local strain.

Depending on the length of the sealings 30.1, on the refractive powers of the light-pipe rods and the sealing material, and on the sealing pressure, coated and uncoated light-pipes may be used for the windows KL3 and KL4. Uncoated light-pipes are optically contacted by the sealings, which reduces the effective aperture angles of the light-pipes near to their entrance. On the other hand, coatings must have a high mechanical strength and must be chemically stable with respect to small amounts of sample solution penetrating the sealings. Some dielectric coatings may be appropriate. As an alternative, the light-pipes may be partially coated with platinum near to their entrance sides. Near to the exit sides, aluminium coating could be applied, too. Sapphire windows will generally need no coatings and give a high light-collecting power.

Light-pipe windows could also be used with the primary light path instead of the disk-shaped windows K1 and K4, in order to reduce the sample volume. With the entrance window K1, however, this would deteriorate the stray light and the imaging qualities of the sample cell, or the light bundle must be as small as to give no light-pipe effect with these windows.

Light-pipe emission windows similar to KL3 and KL4 of FIG. 30A will also be useful in stopped-flow temperature-jump cells of FIG. 37, where large conical windows K3 and K4 cannot be inserted. These windows could also be more generally used with temperature-jump cells, however, measurements of fluorescence polarization cannot be performed. On the other hand, electrical screening between the sample cell and the photodetectors will be simplified, thus favoring applications in simplified apparatus. As above mentioned, the lenses L3 and L4 of FIGS. 1 and 2 could be omitted in simplified and more specialized versions.

As a modification to FIG. 30A, the light-pipes may be made as flat cones instead of cylinders, with an exterior shape varying between the cylindrical windows KL3 and KL4 of FIG. 30A the conical windows K1 and K2 of FIG. 37. Contrary to the latter ones, however, the surfaces of the cones must be polished, and should have a dielectric coating when used in cells where electric fields are involved. Furthermore, they should be longer. Light reflected at the cone walls passes the exit side at an reduced angle with respect to the axis. Thus, a conical light-pipe may be used to give an aperture transformation similar to a light-collecting lens. With respect to a given dielectric coating, the critical aperture angle of a conical light-pipe is larger than that of a cylindrical one, and the light-collecting power is higher for a given entrance surface.

As another alternative to FIG. 30A, FIG. 30B uses short cylinders KS3 and KS4 with conically tapered rims as the emission windows, with lenses 30.3 inserted into the cell body similar to FIG. 25. The cylinders KS3 and KS4 should be made of high refractive material, such as of sapphire, and look similar to those as used as absorption light path windows in shock tube arrangements hitherto. Berichte Bunsenges. Physik.Chemie 75, 1245 (1971). At their inner sides, they are tightened by flat O-rings (rather than round ones as shown in the drawing), e.g. of Teflon. The cell body should preferably be made of stainless steel. The drawing is fairly enlarged, and the relative length of the cylinders should be shortened for pressures of up to 200 atm. Together with a high index of refraction, these windows will pass the emission light with an unexpected large aperture angle, so that the mountings rings must have a special wide angle design (which could be much larger than given in the drawing). Conical lenses K3 and K4 instead of the lenses 30.3, such as of FIGS. 34 and 35, and/or an immersion liquid between the windows KS3 and KS4 and the lenses could be used, too. Therefore, optimized sapphire emission windows for a pressure-jump cell of FIG. 28 will differ considerably from the known shock tube windows.

FLOW-CELLS AND COMBINED STOPPED-FLOW TEMPERATURE-JUMP CELLS

The devices shown in FIGS. 31 to 39 are designed for studying chemical reactions induced by fast mixing of reacting solutions.

FIGS. 31 and 32 are stopped-flow cells with incorporated injection devices.

In the version shown in FIG. 31 the upper part 9.4 of the sample cell is provided with two driving syringes which consist of cylindrical bores 31.1$a$ and 31.1$b$ which are closed at one end by mobile, tightly fitting pistons 31.2. The pistons have a series of notches 31.3 in form of a ratchet. These notches fit into spring-loaded driving pins 31.4 which transmit mechanical forces onto the pistons. These forces may be exerted between a fixed piston 31.5 and a mobile cylinder 31.6 by means of compressed liquid or gas connected via a supply connection 31.7. The mobile cylinder is mechanically connected to the driving pins 31.4. In the backward direction, the driving pins 31.4 can slide to the next respective notch 31.3.

In the shown version the cylindrical bores 31.1a and 31.1b are formed by glass tubes 31.8. On the side which is opposite to the piston 31.2 channels 31.9 join the bores. The bores can be filled through the channels 31.9 with the sample solutions if the pistons 31.2 are pulled back. For this procedure valves 31.10 have to be brought into a position that the channels 31.9 are connected to the supply connection 31.11. In another position of the valves 31.10 the channels 31.9 are separated from the supply connections 31.11 and connected to a mixing chamber X1 via a quick action stop valve 31.12.

The mixing chamber X1 consists of an inner bore 31.13 in a short cylindrical piece of plastic material 31.14 with two grooves 31.15a and 31.15b at the outside. Each groove is connected to its own channel leading to the quick action stop valve 31.12. The inner bore 31.13 is connected to the grooves 31.15a and b by a series of smaller, slightly oblique radial jet bores 31.16 in alternating turns. For mixing, the pistons 31.2 are pushed to the inner side and the solutions are passed to the grooves. The inner bore 31.13 ends in the cell chamber K which, similar to other cell chambers, is made of fused silica or similar and is clamped between two mounting pieces 22.7 and 22.8. Different types of cell chambers, like KA and KB, with larger or smaller volumes or with a different lightpath can be interchanged easily.

A drain channel 31.17 is leading from the cell chamber K to the quick action stop valve 31.12 and from there to an outlet connection 31.18. The quick action stop valves 31.12 stop the supply of the sample solutions to the mixing chamber and the outlet of the waste mixture from the sample chamber simultaneously. Thus the time course of the reaction can be investigated with the reacting mixture in its equilibrating state.

The valves 31.12 are operated by three short pressure pins 31.19 which are fixed to a common disk 31.20. If the valves are closed, each pin presses an elastic sealing element 31.21 onto the respective valve bore which is opposite to the pin and ends at a flat plate. Thus the bores are closed. For opening, the pressure pins 31.19 are lifted from the elastic sealing elements. Then the liquid can leave the bore, it is collected in a circular groove 31.22 around the bore and can flow off. In the shown version a membrane of rubber elastic material is used as elastic sealing element 31.21 which is held down by a plate 31.23 with three larger bores for the pressure pistons. The disk 31.20 with the pressure pistons 31.19 is held down by a strong spring 31.24. It is fixed on the rod 31.26 provided with a notch 31.25. It can be lifted by a button (not shown) in order to open the quick action stop valves. A mobile bolt 31.27, which is loaded by a further spring 31.28, latches into the notch 31.25. When the lifting cylinder 31.6 is operated, the bolt 31.27 releases the notch 31.25 and the quick action stop valves 31.12 are closed. The valve rod 31.26 may be coupled to a contact switch in order to trigger oscilloscope records.

Other simultaneously operated valves can be used, too. A simplified version uses, e.g., a pressure piston and springs in order to close supply tubings made of plastic material or rubber. A separate hydraulic or electromagnetic operation of the quick action stop valve arrangement is also possible.

FIG. 32 shows another flow cell device, in which the waste mixture is collected by an adjustable stopping syringe (FIGS. 32A and B: vertical cross sections in the primary and in the secondary lightpath; FIG. 32C: horizontal cross section in the plane of the driving syringes). The driving pistons 31.2 and the mobile cylinders 31.6 are already mentioned. A reversing valve 32.10 connects the cylinder bores 31.1a and 31.1b either to the supply connections 32.11, which are provided for storage syringes, or to a mixing device X2. The mixing device X2 differs from the mixing chamber X1 by the combination of two smaller mixing chambers X2a which supply the reacting mixture at both ends of the cell chamber K, whereas the waste mixture flows off through a channel 32.17 in the center of the chamber. This channel leads to a collecting cylinder 32.1 with a tightly fitting piston 32.2 which is lifted by the incoming solution until it reaches an adjustable stop position 32.3. The stop position 32.3 is provided with a contact switch 32.4. The collecting cylinder 32.1 will be connected to a drain hose via the valve 32.5 and will be emptied by pressing the piston 32.2 down.

Furthermore, sample cells according to FIGS. 31 and 32 may include characteristics of other cells, e.g. the installation of electrodes and a high-voltage connector 7.11, in order to obtain stopped-flow temperature-jump cells similar to FIGS. 37 and 38.

FLOW-CELLS WITH SEPARATE INJECTION DEVICE

The sample cells of FIGS. 31 and 32 need a very stable support in order to suppress mechanical vibrations which occur during flow experiments. High-pressure lamps are very sensitive to vibrations. The required stability can be obtained, e.g., by mounting the apparatus on a heavy stone table.

As an alternative, flow cells according to FIGS. 33 to 35 with a separate injection device, such as shown in FIG. 36, can be used. The sample cells are connected to the injection device by flexible tubing such as of polyethylene with inner diameters of 1 to 1.5 mm and walls which are 0.5 to 0.7 mm tick. These tubings isolate vibrations of the injection device even at short distances of, e.g., 100 mm very effectively. The injection device is mounted on a separate, mechanically isolated support. Measures for complete suppression of any disturbing effects will be discussed in FIG. 38.

FIGS. 33A and B show a simple flow cell for absorption measurements which is shaped as a curtailed cell of type "A" but which can also be made as a cell of type "B". FIG. 33A is a simplified perspective projection. FIG. 33B is a vertical cross section through the optical axis. FIG. 33C is an illustrative enlarged drawing of the preferred mixing chamber X, which is known construction by Gibson. Sample solutions A and B are supplied at hose connections 8.6a and 8.6b. The solutions flow downward through oblique distribution channels 33.1a and 33.1b, two of which are provided for each solution and lead to opposite entrance bores 33.10 of the mixing chamber body 33.9 (FIG. 33C is turned upside down to give a clear representation). The mixing chamber bore 33.12 has two sections of tangential jet bores 33.11 that give a thorough mixing of both sample solutions. The mixing chamber X is sealed on its bottom side against the body of the cell chamber 33.0 by an O-ring 33.14. The newly mixed solution (AB) flows through a short oblique bore 33.4 into a measuring capillary bore 33.5, where the solution C, which is waste from the preceding experiments, is forced through another oblique bore 33.6 and leaves through a hose connection 8.6c which may be linked to a collecting syringe (e.g. as in FIG. 36C). After the flow is stopped, the time course of the reaction is measured through the two cell windows K1 and K2 in the absorption lightpath of the apparatus. The windows K1 and K2 may be constructed as short cylinders of fused silica, e.g. with diameters of 8 mm and 6 mm thick. They are tightly pressed against perfectly plane surfaces 33.16 by mounting rings 33.7 which can also act as entrance diaphragms. Thin rings of teflon foil are inserted between the mounting rings 33.7 and the windows K1 and K2 (not shown). The diameters of the mixing chamber bore 33.12 and of the oblique bore 33.4 may be 2 mm, but the outlet bore 33.6 may be somewhat smaller in order to provide a flow resistance and avoid cavitation in the capillary bore 33.5. In a design optimized for routine measurements, the measuring capillary bore 33.5 has a diameter of about 2.8 mm and a window distance of 7 mm. This gives a reasonable absorption pathlength and a moderate sample volume, but also a much higher light gathering power than with usual flow cells that have smaller and mostly longer capillary bores. On the other hand, a relatively low condensor magnification is used in FIG. 18. Thus a large "auxiliary light gathering power" is obtained which results in an unusually stable light flux through the cell, but the high-aperture ratios of the monochromator and the cell provide still enough light intensity to give a low photon noise in the ms-range. The lateral limitation of the light beam should be performed by diaphragms S2 and S2' at both sides of the monochromator exit slit $\bar{S}$ as already discussed in FIG. 20. A perfect stability is then obtained by compensating the measuring signal of the detector D2 by the reference detector D1. The bodies 33.0 and 33.2 are inserted into a cylindrical bore 33.15 with stepwise reduced diameters in the brass body 7.3 and are tightly fastened by a metal cap 33.8. In a modified design the cell chamber body 33.0 is inserted into a bore which is coaxial to the axis of chamber capillary 33.5 and is fastened by one of the mounting rings 33.7 via the window K1 or K2, respectively. The bores 33.4, 33.5, and 33.6 and the edges between these bores are polished. The outlet 8.6c is connected to a flexible tubing which is led through a bore in the body 7.3 from the bottom to the top of the cell (not shown).

For higher requirements stainless steel can be used for the cell body 7.3 instead of brass. The mixing chamber X may be made of KEL-F. The same materials are preferred for other flow cells. This indication, however, should be understood as an example and not as a restriction with respect to other materials.

Figure 34A:
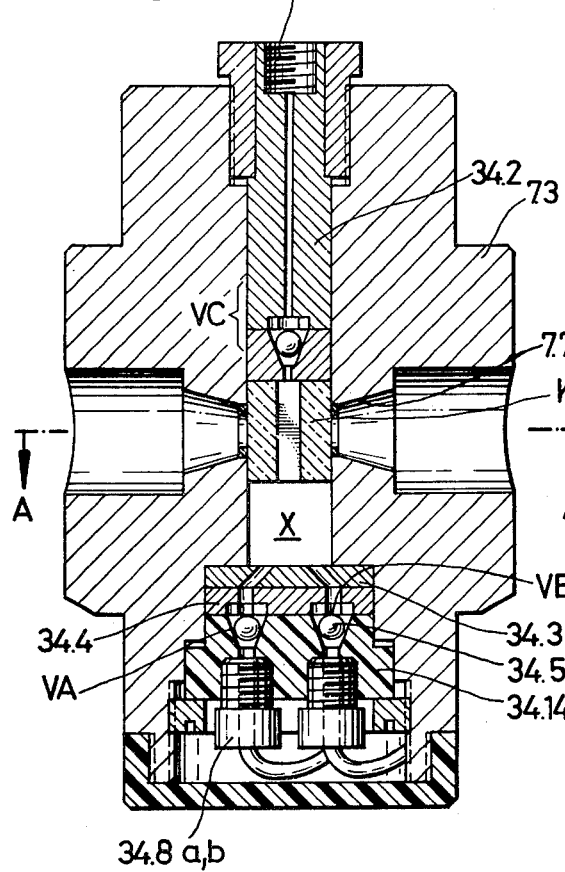
Figure 34B:
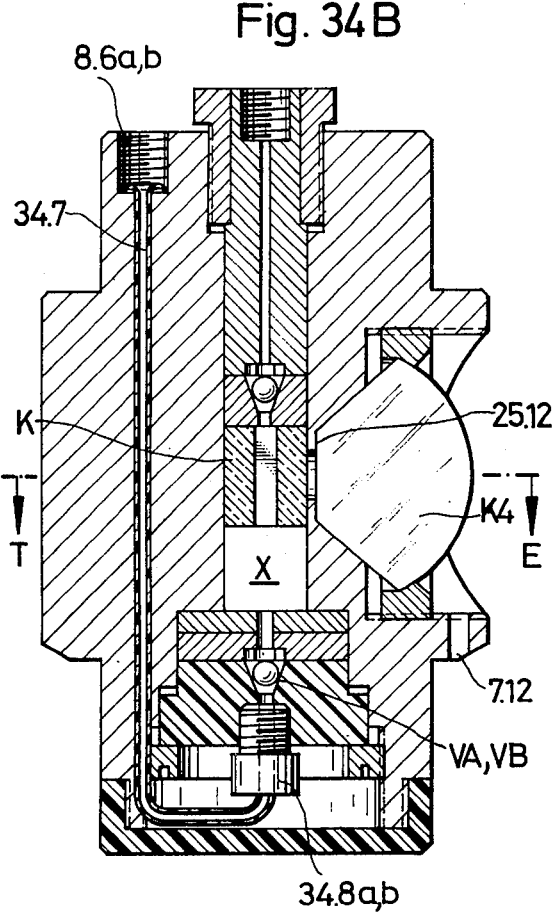
Figure 34C:
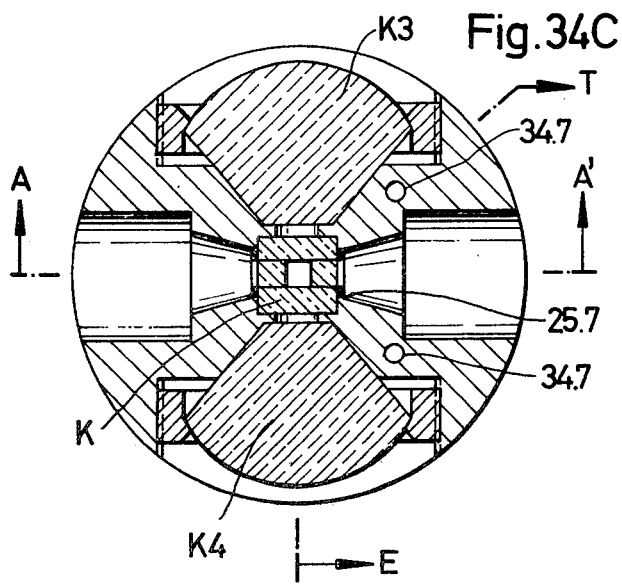
Figure 34D:
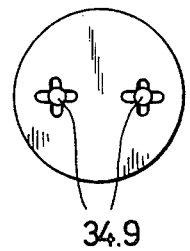

Stopped-flow cells with four (or three) windows for measurements of absorption and fluorescence:

The cell of FIG. 34 is provided with automatic valves and heat exchangers. FIG. 34A is a vertical cross section in the primary lightpath. FIG. 34B is a deflected vertical cross section through one heat exchanger and through half the emission lightpath. FIG. 34C is a horizontal cross section in the plane of the lightpath. FIG. 34D gives a detail of the automatic valves. The capillary cell chamber K may be selected from FIG. 26, e.g. KF or KG. In order to improve the light gathering power in the fluorescence lightpath, conical windows K3 and K4 similar to the lenses 10.8 in FIG. 10 are used. Diaphragms 25.7 and 25.12 should be provided if the cell chamber K is not coated with a black glazing or an equivalent material 26.3. The cell can be further improved by inserting additional windows (K1, K2) into the bores 7.7a in the primary lightpath and by filling the space between the cell chamber K and the windows K1 to K4 with an immersion liquid. - Special features of FIG. 34:

1. Automatic valves: The mixing chamber X (FIG. 33C) is mounted belw the cell chamber K. Two ball valves VA and VB are provided for long-time stopped-flow measurements in order to avoid rediffusion of waste solution mixture back through the mixing chamber and the distribution plate 34.3 into the inlet bores 34.7. The valves consist of valve plates 34.4 and 34.14 and balls 34.5 (e.g. of glass). During the flow the balls 34.5 are lifted against studs in the upper valve plate 34.4, so that their flow resistance is negligible. A lower side view of the valve plate with these studs around the bores 34.9 is shown in FIG. 34D. After the flow has been stopped, the balls return tightly into conical bores in the lower valve plate 34.14. These automatic valves facilitate flow experiments considerably. They avoid errors which otherwise could be caused by manually operated valves because of mechanical vibrations when closing the valves, or errors due to rediffusion if the valves are not operated at all. It follows from the aforementioned statements that these valves are also superior to already used electromagnetic valves and less costly. A further ball valve VC is installed in the outlet bore above the cell chamber K, too.

2. A heat exchanger guarantees that only perfectly thermostatted solutions A and B can flow into the mixing chamber and into the cell chamber K. This heat exchanger has been constructed as follows: the cell body 7.3 consists of brass. The bores 34.7, which serve to link the outer hose connection to the valve connections 34.8a and b, are tightly lined with thin plastic tubings, e.g. of polyethylene. The solution which remains after the flow-experiment in these tubings attains the cell temperature with a very short thermal time constant. The sample volume in the tubings is small compared to the surrounding cell body. Thus initial differences of temperature of about 10° centigrade are reduced to a few tenth of a degree within a period of one or a few minutes. Thermostatting is far superior to many conventional flow apparatus, especially those with a chemically inert cell chamber which is insufficiently thermostatted because of the bad thermal conductivity of the involved materials used in an unfavourable construction. The necessity to use a separate injection device ES, which seemed to be a disadvantage, is also to be an important advantage in biochemical studies: many biochemical substances are stable only at low temperature, but their reactions have to be investigated at higher temperature. The new apparatus, together with sample cells according to FIG. 34 (also FIGS. 35, 37, and 38) allows one to operate the injection device ES at low temperature where the solution is stable even for longer times. The respective sample volume needed for the next flow experiment may thus be brought up to its final temperature only shortly before the experiment.

Figure 35C:
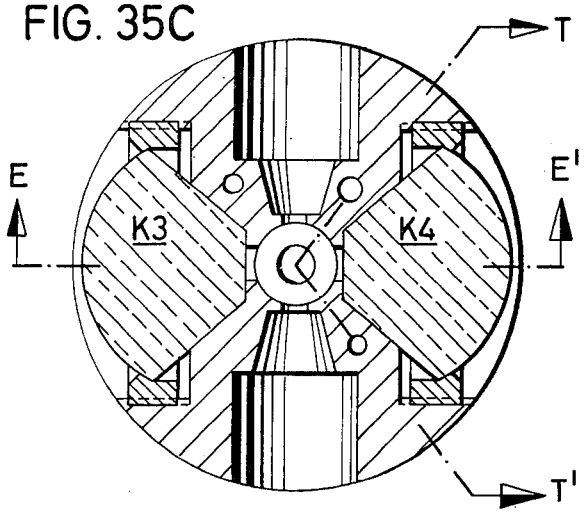
Figure 35D:
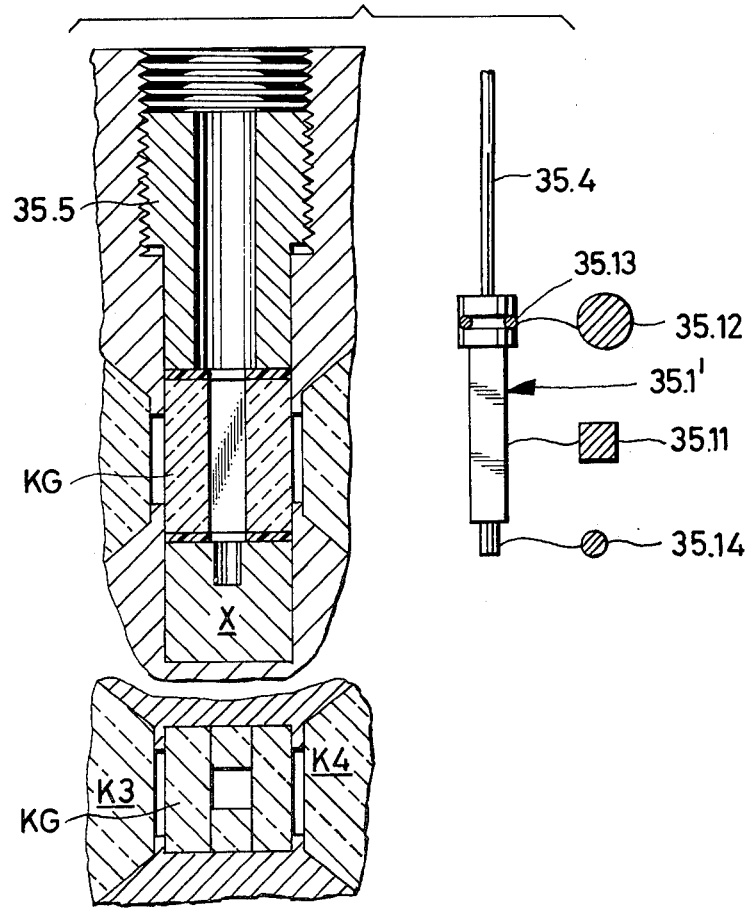

The sample cell of FIG. 35 is a stopped-flow cell provided with an internal stop piston in order to operate with minimal sample volumes. The drawings show how to adapt and improve this known arrangement in a cell used with the new apparatus. FIG. 35A is a vertical cross section in the emission lightpath. FIG. 35B is a deflected vertical cross section which shows a heat exchanger bore 34.7 at the right hand and a thermometer probe 35.8 at the left hand. FIG. 35C is a horizontal cross section. FIG. 35D is a detail of an improved version. The mixing chamber X is arranged below the capillary cell chamber K. Valves VA and VB according to FIG. 34 could be provided, too. The cell chamber K is clamped between sealing disks 35.9 by a threaded mounting cylinder 35.2. Inside the cell chamber a sliding piston 35.1 has been installed which fits tightly either the cell chamber bore itself or the inner bore of the mounting cylinder 35.2. The piston 35.1 is provided with a capillary rod 35.4 moving in an adjustable stopping screw 35.3, which is locked by a nut 35.6. The capillary rod has a valve VC at the outlet connection 8.6c. Prior to each measurement the valve VC is opened, the capillary rod 35.4 and the piston 35.1 are pressed down to the bottom of the cell chamber, and the valve VC is closed again. During flow, the piston is lifted up and stopped by the stopping screw 35.3. Thus the piston acts as a stopping syringe (similar to the syringe Y of FIG. 36C). With a given cell chamber volume this results in the lowest possible amount of sample volume needed for each flow experiment because only a small amount of waste mixture from the preceding experiment mixes up with the newly mixed sample, whereas other stopped-flow systems need at least twice the chamber volume for driving out the waste mixture sufficiently.

The drawings of FIG. 35 give an exaggerated chamber dimension which may be further reduced. According to FIG. 35D, using a modified piston 35.1λ and a cell chamber KG, which are shown together with the mixing chamber and a modified mounting cylinder 35.5, the cell chamber must not have a circular bore. The piston may have a lower part 35.11 with a rectangular cross section, which fits a cell chamber KG of FIG. 26 with a small gap, and a cylindrical upper part 35.12, which fits tightly the mounting cylinder 35.5 (e.g. by a small O-ring 35.13). The piston may also continue in a small cylindrical pin 35.14 at its lower side which intrudes into the center bore of the mixing chamber when the piston is pressed down. This modification gives minimal sample volume and optimal optical performance simultaneously and reduces also rediffusion.

The heat exchanger bores 34.7 may be lined with thin plastic material similar to FIG. 34. In a simplified version the cell body 7.3 is made of stainless steel without lining the bores 34.7. The inlet connections 8.6a and b are connected to an injection device as shown in FIG. 36A and B.

Figure 36C:
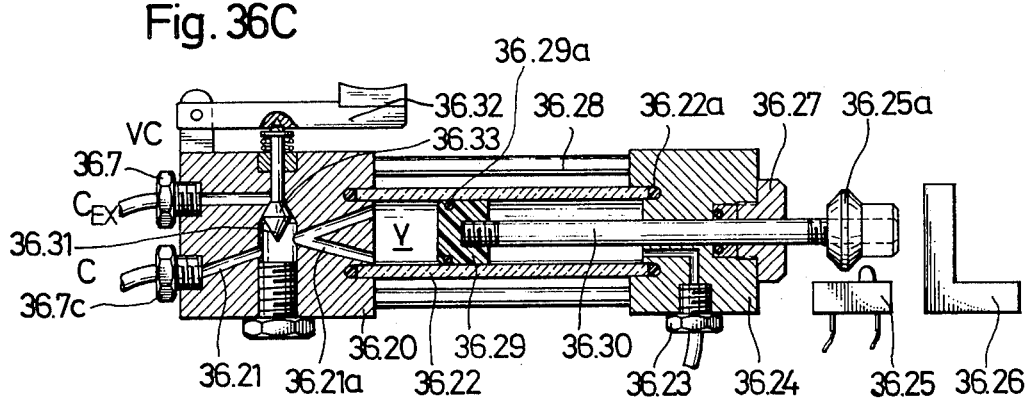
Figure 36D:
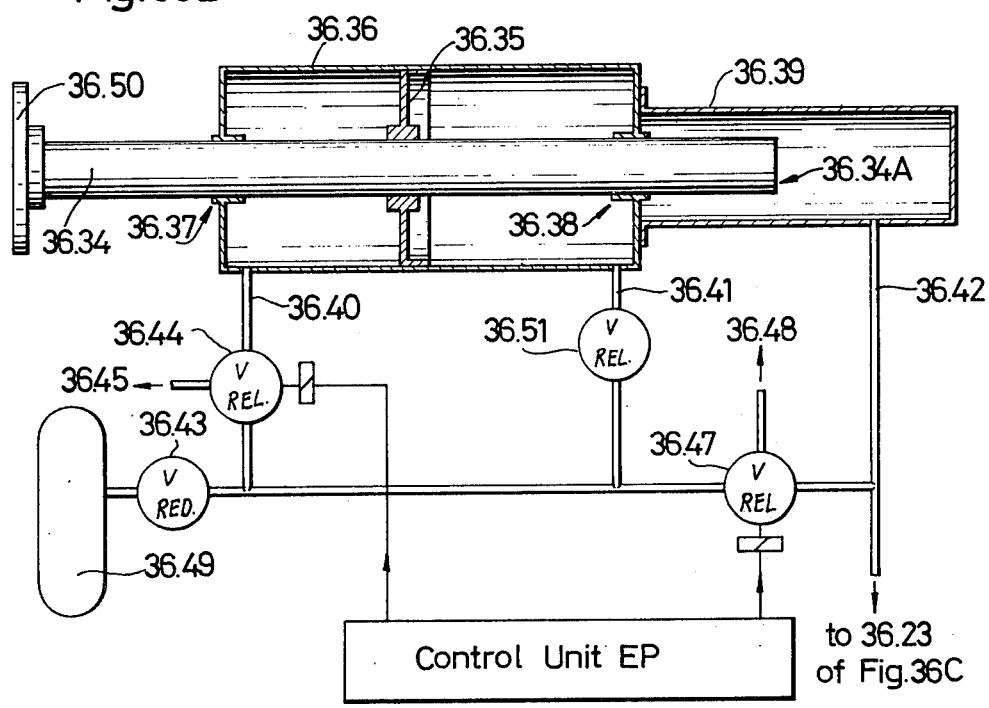

FIGS. 36 shows a version of the injection device ES with driving syringes WA and WB for operating stopped-flow and stopped-flow temperature-jump cells according to FIG. 33 and following with the new apparatus. An added advantage of the separate injection device is the easy interchange of cells optimized for special purposes. FIG. 36A is a right hand view of a valve block (36.3) with valves VA and VB and supply syringes 36.1a and 36.1b. FIG. 36B is an axial cross section of the injection device. FIG. 36C is the corresponding stopping syringe device with a stopping syringe Y and an outlet valve VC. FIG. 36D is an improved version of a pneumatic driving cylinder connected to the excitation unit EP of FIG. 1. Part of the driving cylinder is already shown at the right hand of FIG. 36B.

The injection device of FIGS. 36A and B is constructed as follows: The driving syringes WA and WB have glass shells 36.12, driving pistons 36.11 (e.g. of Teflon with O-rings 36.11a of synthetic rubber), driving rods 36.16, and conical front caps 36.10. The front caps have one or two oblique channels 36.10a in upward and downward directions, where the upper channel gives an important improvement in removing air bubbles when filling the syringes. The lower channel compensates for hydrodynamic pressure differences. The syringes are mounted in a thermostatted holder which consists of a valve block 36.3 with supply connections 36.4 and 36.6 connected to a liquid thermostat (EH of FIG. 1) and with liquid bores 36.15 leading inside a mounting cylinder 36.5 of acrylic glass or equivalent material, which is sealed by O-rings 36.5a, a mounting plate 36.14 with threaded caps 36.13 and sealing O-rings 36.13a for pressing the driving syringes WA and WB against the valve block 36.3, and mounting bolts 36.8. The valve block 36.3 and the mounting plate 36.14 should be made of metal, e.g. of brass, where valve elements 36.2 of inert plastic material are tightly inserted or shrunk into cylindrical bores of the valve block and held in place by a plate 36.17. The valve elements have longitudinal bores 36.9, which match the supply syringes 36.1a and b at the upper sides and hose connections 36.7a and b at the lower sides, and have transverse bores 36.18, which are conically widened at the right sides for matching the conical caps 36.10 and also conically widened in the center for the valve cocks 36.19. This design combines perfect thermostatting and perfect chemical and mechanical properties. The syringes WA and WB can easily be interchanged for various mixing ratios if appropriate threaded caps 36.13 are provided. A third driving syringe for multiple mixing or extreme mixing ratios could also be provided which is replaced by a blind plastic rod if the third syringe is not inserted.

The valves VA and VB are three way valves, which connect the driving syringes WA and WB either to the supply syringes 36.1a and b for filling, or connect them to the hose connections 36.7a and b for flow experiments, or close the connections. The connections 36.7a and b may have bajonet sockets (e.g. connections known under the trademark "Luer-Lock"). If sample cells without a heat exchanger are used, plastic tubings covered with metallic fabric hoses (especially of copper) may be used for the hoses leading to the cell, where metallic plugs are provided both with the injection device and with the sample cell in order to give thermal contact. These hoses should be covered by thermal insulation hoses, e.g. of foamed rubber, and be rather flexible. As an alternative, coaxial plastic tubings are used where the outer ones are liquid thermostatted. The injection device of FIGS. 36.A and B, the pneumatic driving cylinder 36.36 and the stopping syringe device of FIG. 36C are mounted on a suspension bar which is mechanically isolated from the mounting plate of the apparatus. In modifications of the driving syringe unit of FIGS. 36A and B, the valve elements 36.2 are inserted into the valve block 36.3 as cylinders which are coaxially aligned to the axis of the syringes WA and WB, respectively, and the bores 36.9 are formed by separately inserted plastic elements transverse to the syringe axis. The driving syringe unit can also be arranged to have the driving syringes in the vertical direction where the pneumatic driving cylinder acts from below. In this case the supply syringes 36.1a and b and the toggles of the valves VA and VB interchange their positions, so that the supply syringes are aligned with the respective driving syringes. The syringe plugs 36.10 should have one straight centerbore each instead of the oblique bores 36.10a and the inner sides of the plugs should be undercut with a flat hollow cone so that bubbles are collected by the hollow cone and can easily be removed. The syringe pistons 36.11 have elevated flat cones in order to give a minimal dead volume.

In FIG. 36C the stopping syringe Y is formed by a glass cylinder 36.22, which is mounted between a valve block 36.20 and a mounting block 36.24 by means of screw bolts 36.28 and sealing O-rings 36.22a, and by a piston 36.29 (which may be sealed by an O-ring 36.29a) with a piston rod 36.30. The piston rod has an adjustable stop position, e.g. a knurled and locked nut 36.25a and a stop-dog 36.26. The nut actuates also a contact switch 36.25 for triggering signal records. The valve block 36.20 has an inlet hose connection 36.7c, which receives waste sample solution C from the measuring cell, and an outlet connection 36.7, which releases solution $C_{EX}$ when the valve VC is opened and the stopping syringe is emptied. The valve block has two oblique bores 36.21 and 36.21a where the oblique arrangement enables easy remove of air bubbles similar to the oblique bores 36.10a with the syringes WA and WB. The valve VC consists of a spring-loaded valve piston 36.30 together with a conically relieved bore 36.31, which is connected to the inlet 36.7c and to the bore 36.21 at its lower side and to the outlet 36.7 at its upper side. The valve piston 36.30 has a double cone which passes solution and bubbles easily when the valve is opened by pressing the lever 36.32 down.

For operating the stopping syringe unit with the syringe axis in the vertical direction, the valve VC has to be arranged upside with the inlet 36.7c and the outlet 36.7 at the sides. The oblique bores 36.21 and 36.21a have to be replaced by a straight center bore where the valve block is undercut by a flat hollow cone facing the syringe piston. The syringe piston has a flat elevated cone, same as above described for modified syringes WA and WB. The stopping syringe unit of FIG. 33C has been further improved by an arrangement which supplies the total flow system by a static overpressure, in order to remove even very small air bubbles which sometimes stick to the walls of the cell chamber and become a limiting factor in measurements of absorption, fluorescence and scattered light. Furthermore, the bubbles favour effects of cavitation which also limit the sensitivity of fast flow apparatus. The bubbles can be dissolved in the solution if an appropriate overpressure is applied. This is done by sealing the piston rod 36.30 at the mounting block 36.24 by an adjustable sealing 36.27, which serves as a packing gland, and by a pressure hose connection 36.23. Due to the backside sealing of the glass cylinder 36.22, the pressure force is given by the applied static pressure together with the cross sectional difference of the piston 36.22 and the piston rod 36.30.

The overpressure will be normally applied prior to a series of measurements after filling the driving syringes. In an improved design of the pneumatic driving system, as shown in FIG. 36D, the driving cylinder is supplied with a balancing differential pressure force in order to pressurize the total flow system independently on the position of the driving and stopping syringes.

According to FIG. 36D, the pneumatic driving cylinder 36.36 is provided with a double-acting piston 36.35 mounted on a piston rod 36.34 with packing glands 36.37 and 36.38 at both sides of the cylinder. The driving plate 36.50 is mounted onto the left end of the piston rod 36.34. Similar to an already known arrangement, the right hand air inlet 36.41 is directly connected to a pressure reservoir vessel 36.49 via a pressure reducing valve 36.43. The left hand air inlet 36.40 is provided with a fast pressure release valve 36.44 with an outlet 36.45. The pressure release valve 36.44 is controlled electro-magnetically by the pressure control unit EP of FIG. 1. On the pressure release the piston 36.35 and thus the driving plate 36.50 are pushed to the left hand side and drive the driving syringes of FIG. 6B until the flow is stopped by the stopping syringe of FIG. 36C. The piston 36.35 is rebalanced after the valve 36.44 switches back to its normal high-pressure position. This procedure and the needed electronic control circuits have already been described in literature. In order to provide the above mentioned static overpressure, a smaller cylinder 36.39 with a pressure inlet 36.42 is tightly attached to the right hand side of the cylinder 36.36. The inlet 36.42 is connected to the vessel 36.49 by another prssure release valve 36.47 with outlet 36.48. Thus an additional pressure force is active on the right end surface 36.34a of the piston rod 36.34. However, the valve 36.47 is also connected to the rearside pressure inlet 36.23 of the stopping syringe Y. The crosssection of the surface 36.34a is matched to the differential cross section of the stopping syringe with respect to the surfaces of the driving syringes WA and WB. Thus the static overpressure is the same both at the driving syringes and at the stopping syringe and the flow system is balanced. The flow system can be activated as before by releasing the first valve 36.44. The pressure release valve 36.47 has to be released only for emptying the stopping syringe or for refilling the driving syringes. For the latter operation, the driving plate 36.50 can be withdrawn pneumatically by a third pressure release valve 36.51 provided with the pressure inlet 36.41 at the right side. According to the improvement, the piston rod 36.34 should be made as a hollow one in order to obtain small inertial forces and strong mechanical stability. FIG. 37 shows a sample cell for combined stopped-flow temperature-jumps using measurements of absorption: As far as symbols are repeated, they have the same meaning as in the preceding figures. A conical distribution element 37.12 is mounted onto the inlet side of the mixing chamber X according to FIG. 33C, which has the same function as part 33.2. The grounded upper electrode is a stub cone made of stainless steel and has a center bore 37.13 for the mixing chamber X and six oblique distribution bores 37.10 leading radially to the cell chamber. O-rings 37.9 are provided for sealing. This construction provides a uniform flow in the cell chamber even in the case of a larger chamber volume. On the lower side of the cell chamber the waste mixture leaves through a conical gap 37.7 between the cell body 7.3 and the lower electrode 37.8, through a circular channel 37.6, through two or four ascending bores 37.5 connected to an upper circular channel 37.4, which leads to the outlet 8.6c via an oblique channel 37.14 and a sealing element 37.11. The inlet and outlet connections 8.6a, b, and c are, e.g., the aforementioned "Luer-Lock" cones and are mounted in a plate 37.1, which is fixed to the insulating cell body 7.3 by a threaded cap 37.2 and alignment pins 37.15.

The cell of FIG. 37 is inserted into the cell holder HZ with a threaded mounting ring with a flat cone at its lower side, which fits the flat cone 37.16 of the threaded ring 37.2 similar to the aforementioned cones 5.7 and 7.9 and provides an exact positioning of the cell. A preferred chamber volume is, e.g., a cell chamber of 2.5 × 8 × 10 mm height.

The sample cell of FIG. 37 can also be constructed as a four window cell, e.g. for providing two absorption path lengths of, e.g., 2.5 and 8 mm. The measures for using this cell as a fluorescence cell with high light-collecting efficiency in the emission light paths have already been discussed in conjunction with modifications of pressure-jump cells according to FIG. 30A and variations thereof, including cylindrical and conical lightpipe windows KL3 and KL4.

The sample cell of FIG. 38 is a stopped-flow temperature-jump cell provided for measurements of absorption and fluorescence. This cell starts from the basic design of FIG. 25, using many identical or sightly modified parts, e.g. an interchangeable sample cell chamber capillary KG. Similar to FIG. 37, the mixing chamber X is enclosed in the grounded upper electrode, together with oblique distribution channels. The cell is connected to the driving unit of FIG. 36 or similar by hose connections 8.6a and b. The solutions then pass through a fairly large heat exchanger of plastic tubings embedded in a heavy heat exchanger body 38.3 of, say, copper, with bores 38.15. The tubings are partly embedded in heat conducting epoxy (e.g., filled with copper). The waste mixture flows off at the lower side of the cell chamber, travels along oblique channels 38.7 at the outside of the high-voltage electrode, is collected in a annular slot 37.6, and moves upward through a bore 37.5, etc.

In the drawing of FIG. 38, several features and details have been superimposed which normally will not be applied to one individual cell, so they are given as examples:

First, this cell is of type "B" (FIG. 8) which is needed with larger cells only. Next, this cell is armoured with a metal mantle 38.5 and 38.2, which improves mechanical stability and thermal contact of the cell to the cell holder HZ, but may be applied by numerous variations to other measuring cells, too (c.f. FIG. 33). Further, the heat exchanger is somewhat larger than needed with a microcell of, e.g., 50 microliters. It could be also useful with the larger sample volume in FIG. 37. The channels around the high-voltage electrode are obliquely arranged in order to provide a rotary movement of the flow in the annular slot 37.6 and to drive out bubbles that could stick in this slot.

Last not least, the inlet and outlet hose connections are arranged in a way so that the mechanical shock during the flow period will be compensated and cancelled because of the opposite directions of partial flows. For this reason, the outlet flow has been divided into two equal partial flows at the connection 8.6c. The tubings connected to the inlets and outlets must continue for a small distance in the horizontal direction. This compensation will be useful in fast mixing of samples, especially with larger sample chamber volumes.

Practically, a cell of FIG. 25 may be converted into a stopped-flow temperature-jump cell by using only parts of the cell of FIG. 38, i.e. by interchanging the bottom electrode, where the outlet bore 37.5 and 37.5a is just provided in the cell body, by replacing the upper electrode with its bayonet socket by an electrode provided with a mixing chamber, and by adding an additional heat exchanger screwed onto the cell holder.

SLOW TEMPERATURE-JUMP CELL

Classical temperature-jump measurements become critical in the time range longer than a few seconds with respect to cooling of the heated sample solution. On the other hand, switching of liquid thermostatting of a spectrophotometer cell (as above mentioned) is limited to times which are several times longer than the long time limit of the classical temperature-jump methods. The time limits are given by diffusional constants; thus, for a given temperature, no complete matching of both techniques can be expected. This is especially true for fluorescence measurements where fast thermostating microcells cannot be easily designed because of the crossed light paths. Successful matching, however, would require methods which have sufficient overlap.

Attempts have been made to push the sample solution through a heat exchanger the temperature of which differs from the initial temperature of the solution. The effective temperature-jump risetime would then be given by the flow time of the solution through the heat exchanger. It can be shown, however, that no uniform heating can be achieved with a finite heat exchanger volume. Thus, data obtained with this method will not be very accurate.

Figure 39B:
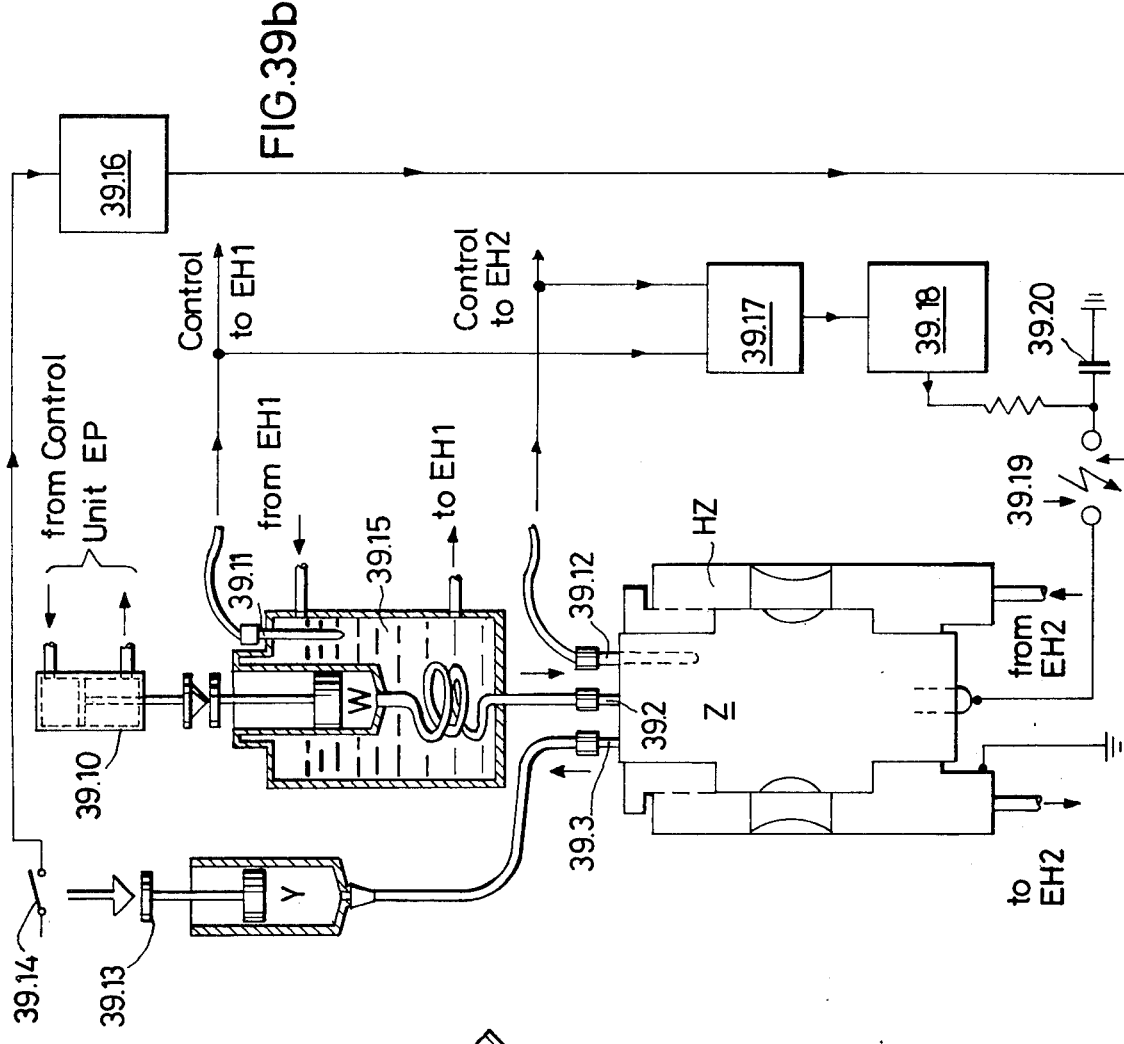
Figure 39A:
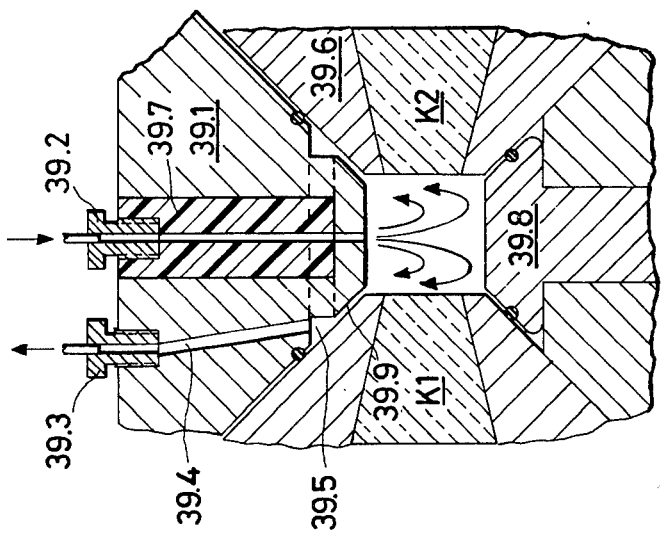

An improved arrangement for performing temperature-jumps in the time range of 10 ms to 1000 secs and longer is shown in FIG. 39. FIG. 39A is the cross section of a special flow temperature-jump cell provided with only one inlet connection 39.2 and one outlet connection 39.3. The incomming solution flows through a thermally insulating plastic piece 39.7 inserted into the grounded electrode 39.1. The solution is injected into the cell chamber through a small cenderal bore in the upper electrode, thus forming a jet driving the present solution effectively out without needing an outlet near to the lower electrode. Instead of this, a gap 39.9 similar to the gap 37.7 is provided around the upper electrode through which the solution passes into a ring channel 39.5, then leaving the cell via an outlet bore 39.4. The upper electrode above the ring channel and the lower electrode are tightly sealed by O-rings. This design resembles to some aspects the cell of FIG. 37 when replacing the mixing chamber by an inlet similar to parts 39.2 and 39.7, however, in the version of FIG. 39A the incomming sample has less thermal contact with the thermostatted upper electrode and has to subdue less flow resistance in the thermostatted upper electrode. (It should be mentioned, however, that a flow temperature-jump cell of FIG. 37 could also be provided with a central inlet jet bore at the upper electrode and an upper ring channel instead of the lower one.)

The complete device for performing the slow temperature jumps shown in FIG. 39B: The sample cell Z is at high temperature $T_2$. The sample solution is stored in a driving syringe W provided with a heat exchanger 39.15, both being at low temperature $T_1 < T_2$. Now the solution is injected by the driving unit 39.10. The old solution in the sample cell chamber, which is at temperature $T_2$, is driven out, flowing into a stopping syringe Y. A few milliseconds later, the spark gap 39.19 is triggered via a contact 39.14 and an control unit 39.16. The high voltage charge stored in the capacitor 39.20 and delivered by the high-voltage power supply 39.18 is automatically adjusted by a thermocontrol unit 39.17, to which two temperature probes 39.11 and 39.12 are connected. Thus the high-voltage pulse energy discharged across the sample solution is such that the injected cold solution is exactly heated to the cell temperature $T_2$. As the cell is on the final and not on the initial temperature of the sample solution, no cooling effects can occur, and measurements extending to infinitely lasting times can be performed. A thermostat EH 1 providing for the temperature T 1 and a thermostat EH 2 providing for the temperature T 2 (both not shown in FIG. 39 B) may be connected to appropriate connection means of the heat exchanger 39.15 and the cell holder HZ, respectively, as indicated in the drawing.

DEVICES AND SAMPLE CELLS FOR FLASHLIGHT EXCITATION

Investigations of chemical reactions using the flashlight photolysis perturbation method may be performed easily with the new apparatus, especially if only one detection light path measuring absorption is needed. The new apparatus should be arranged in the block building technique (see below). The secondary light path, which is used for measurements of fluorescence and scattered light with the other perturbation methods, will then be used for application of the flashlight. The emission photodetectors D3 and D4 are removed (FIGS. 1, 2 or 3). A flashlight excitation unit EF (FIG. 1), together with appropriate condensor elements, such as lenses and mirrors, and spectral filters, is installed in place of one emission photodetector, say D3. A narrow bandfilter F2 is inserted in front of the photodetector D2. As a measuring cell, a conventional spectrophotometer cell (rectangular cuvette with four windows) may be used in a cell adaptor of FIG. 10. In an improvement hereof, one of the two conical lenses 10.8, which is opposite to the flashlight source, has been replaced by a concave mirror. This mirror images the center of the cell or the entrance diaphragm 10.7a, which is near to the flashlight source, onto itself. In order to reduce stray light, the other conical lens 10.8 is either omitted, to its spherical outer surface has to have a curvature so that light reflected from said mirror and reflected again from said spherical lens surface is focussed into the center of the cell. The lens L3 can be removed from the cell holder HZ, or it is used as part of the flashlight illumination optics, as well as the filter holder HP3. Special flashlight cells may also be constructed similar to a temperature-jump cell the cross section of which is shown in FIG. 5A. However, the internal window surfaces should have a slightly withdrawn position so that stray light is reduced. The conical window K4 is further replaced by a glass body with coated reflective outside, which images the center of the cell or the inner surface of the opposite window K3 onto itself. (A cell with a reflecting glass body of this type has been described in the application Ser. No. 487 592, now U.S. Pat. No. 3,972,627). The spherical outer surface of the window K3 should have a radius of curvature so that light reflected from said glass body and again reflected from said special window surface is focussed into the center of the cell. Filters stopping the flashlight wavelength band and passing the monochromator wavelength should be used for the filter F2, especially an arrangement of dichroic mirrors in 45°-positions with respect to the light paths.

In another version the flashlight is introduced from the upper side, e.g. in set-ups using the dual wavelength absorption technique. If spectrophotometer cells are used, the light is introduced by means of a light-pipe rod which is immersed into the sample solution.

Flashlight cells specially designed for flashlight application from the upper side are shown in FIGS. 40 and 41, which are cells of type "C" (FIG. 9).

The cell of FIG. 40 will be used together with an external flashlight source, e.g. with a pulse laser. The cell chamber K is provided for measurements in the primary and in the secondary light path of FIGS. 1 through 3. A liquid filter cell 40.1 has been installed directly above the sample solution. Additional filter glasses and other filter elements can be inserted into a filter chamber 40.2 above the liquid filter cell, or into the cover opening 40.7 of the liquid filter cell. The flashlight is introduced via a prism 40.5 provided with means for azimuthal (40.3) and ascendental (40.4) adjustments. A concave mirror 40.6, which is placed below the sample chamber and coated on its backside, increases the flashlight intensity.

FIG. 41 shows a more compact measuring device which is obtained from the device of FIG. 40 by replacing the prism mounting (40.3, 40.4 and 40.5) by a flashlamp mounting 41.3 with a flashlamp QF. The filter glasses are inserted into the cover opening 40.7 of the filter cell 40.1. A reflector 41.4 is arranged above the flashlamp. A flexible light-pipe 41.5. is connected to the flashlight mounting in order to provide an optical trigger signal which, e.g., is converted into an electrical signal by coupling the light-pipe to the photodetector D1' in FIG. 1. Thus the time course of the flashlight pulse can be measured and compared to the time course of the measuring signal obtained from the photodetector D2.

MECHANICAL OUTLINE OF THE APPARATUS

Details of a version of the sample cell unit EZ have already been described in conjunction with FIG. 4. The sample cell unit of FIG. 4 encloses any standard optical elements of FIG. 2 which follow the monochromator. Replaceable or interchangeable parts, which are mounted onto the bottom plate 4.4 of the sample cell unit, such as the prism bed HH, filter holders HF1 and HF2 with mounting blocks 4.1 and 4.2, should be aligned by alignement pins or small alignement rails. The same holds for the mounting block 4.3 of the beam splitter. Any of these compenents may then be released by releasing a screw (cf. FIG. 12B: screw bore 12.17, alignement pin bores 12.18). E.g., the prism bed and/or the beam divider may be replaced by a fast optical modulator in AC-modulated arrangements, such as for measurements of optical rotary dispersion or circular dichroism. The polarizing prism P may then be mounted in a separate holder, or the prism bed may be moved to the standard position of the beam splitter.

Other components used in extensions of the design of FIG. 2 will be contained in auxiliary housings connected to the sample cell unit EZ, e.g., in FIG. 3: dichroic beam splitter TF', filter F2, and lenses LO', L20, and $\overline{L1}'$.

The light source and the photodetectors should have their own housings, too. Rearrangements of the optical set-up may thus be easily performed; photomultipliers may be replaced by semiconductor photodetectors, etc. Optimum versality and high stability have been obtained by mounting the optical units — i.e. light source, monochromator, sample cell unit, and photodetectors — on optical benches provided with the primary, the secondary, and the reference light paths. These optical benches should be mounted on a shock-isolated mounting plate, which is electrically conducting and serves as a reference earth to the apparatus. Screening between the high-voltage excitation unit ET and the photodetectors and the opto-electronic control unit ED (FIG. 1) is thereby simplified and improved.

In a preferred version, said mounting plate is formed by a plane metal plate, e.g. of aluminum alloy, which is reinforced at its lower side by a mounting frame such as of profiled steel tubings. Mechanical resonances (flexural vibrations) of this construction have been successfully damped out by inserting a thin layer of plastic material between the metal plate and the mounting frame, such as of plastified and self-adhesive PVC. The mounting plate is then mounted on anti-shock suspension elements, e.g., onto a table-like suspension frame of steel tubings, which, in its lower part, contains power supplies and excitation units of the apparatus.

The injection device of FIG. 36 is mounted on a swivel arm or bracket mounting attached to the suspension frame of the apparatus.

What is claimed is:

1. Apparatus for investigating fast chemical reactions by optical detection, said reactions being initiated in a chemical system by an external perturbation, said apparatus comprising means for performing said external perturbation, at least one light path, means for supporting a sample cell in said light path, said sample cell forming a cell chamber for holding a liquid sample of said chemical system, at leat one photodetector, said light path comprising a light source, a monochromator, means for imaging said light source onto the entrance of said monochromator, and means for imaging the exit of said monochromator onto said sample cell chamber, said apparatus comprising also means for directing light from said liquid sample onto said photodetector, the improvement comprising:

(a) a set of at least two different types of sample cells, each of said types having one different means for application of at least one parameter of perturbation, said means comprising:
  (a.1) two electrodes facing opposite sides of said chamber for temperature-jump and field-jump perturbation,
  (a.2) a pressure autoclave and pressure release means for pressure-jump perturbation,
  (a.3) at least one optical window in an auxiliary light path for flash-light perturbation,
  (a.4) a mixing chamber and flow-channels for rapid mixing, and
  (a.5) two electrodes, a mixing chamber, and flow-channels for combined rapid mixing and temperature-jump perturbation; each of said sample cells having a specific sample volume at least two optical windows for application of at least one of the following parameters of observation: optical absorption, fluorescence, scattered light, and parameters of polarization, said sample cells having identical exterior dimensions at least in their middle parts and an identical position of their main optical axis with respect to said exterior dimensions;

(b) at least two different ones of the following perturbation supply means:
  (b.1) a high-voltage pulse source,
  (b.2) a pressure supply,
  (b.3) a flash-light source, and
  (b.4) a stopped-flow drive system;

(c) a metallic sample cell holder mating said sample cells and holding one selected sample cell operatively inserted into said apparatus, said holder comprising:
  (c.1) a hollow structure having a main axis, enclosing said selected sample cell in close mechanical and thermal contact,
  (c.2) threaded fixation means for clamping said sample cell therein,
  (c.3) thermostatting channels connected to a liquid thermostatting system,
  (c.4) window openings for passing said light path in a direction perpendicular to the main axis of said hollow structure, and
  (c.5) means for connecting a high-voltage pulse source at one end of said hollow structure; and (d) a set of changeable optical elements adapting said light path to the optical dimensions of the chamber of said selected sample cell, said elements comprising at least one lens mounted in an axially adjustable holder and at least one diaphragm modifying the free exit aperture of said monochromator.

2. Apparatus according to claim 1, provided with a first and a second light path, said light source and said monochromator being in said first light path, said second light path serving as a secondary light path for fluorescence and scattered light measurements, both light paths crossing in said cell holder and said cell chamber at right angles in a plane vertical to the main axis of said cylindrical structure, said sample cell having at least three optical windows, said second light path further comprising at least one photodetector, means for light filtering and means for directing light emitted from said liquid sample onto said photodetector.

3. Apparatus according to claim 1, provided with a collimating lens and a collecting lens between said monochromator and said cell holder, said lenses imaging said monochromator exit onto said cell chamber.

4. Apparatus according to claim 3, including an axially movable lens holder for mounting one of said lenses, a supporting device for said lens holder, and scales provided with wavelength and cell corrections.

5. Apparatus according to claim 4, further comprising a set of interchangeable collecting lenses, said lenses being used with said movable lens holder and having different focal lengths.

6. Apparatus according to claim 3, further comprising a polarizing prism between said collimating lens and said collecting lens, said prism being mounted in a rotatable prism holder, said holder giving preferred orientation angles and being removable from said light path.

7. Apparatus according to claim 6, provided with an axially movable combined prism and lens holder interchangeable with a single lens holder and a supporting device for said holders, said holders mounting said collecting lens.

8. Apparatus according to claim 6, wherein said prism holder is shaped as an irregular octogon, further comprising a supporting device mating three adjacent surfaces of said octogon, which give preferred orientation angles of the prism: 0°, 35.3°, 45°, 54.7°, and 90°.

9. Apparatus according to claim 6, wherein the light beam between said collimating lens and said collecting lens is slightly convergent towards said collecting lens and said polarizing prism is placed close to the image of the monochromator aperture plane.

10. Apparatus according to claim 6, further comprising a depolarizer in front of said polarizing prism.

11. Apparatus according to claim 10, wherein said depolarizer is mounted on a swivel arm for quick insertation into said light path.

12. Apparatus according to claim 3, further comprising radiant field diaphragms ($S_1$, $S_2$) at both sides of said monochromator exit ($\overline{S}$), said radiant field diaphragms limiting the lateral dimensions of said light path and being imaged onto the entrance aperture and the exit aperture of said sample cell, respectively.

13. Apparatus according to claim 12, wherein the distance of said lenses is approximately equal to the sum of the focal lengths of both lenses, said radiant field diaphragms being in symmetric positions to the monochromator exit and having equal sizes.

14. Apparatus according to claim 12, further comprising a set of interchangeable radiant field diaphragms and a mounting device holding said diaphragms, said device comprising: a set of interchangeable plug-in tubes and a holder for said tubes, said holder fixed to the housing of said monochromator, each of said tubes mounting one individual pair of said diaphragms, said tubes and said holder having an oblong hole transvers to said light path and between said diaphragms, said hole passing an interchangeable slit diaphragm used as the monochromator exit slit, said holder further comprising means locking said slit diaphragm.

15. Apparatus according to claim 3, further comprising a beam splitter in said light path prior to said collecting lens, and a further collecting lens and a reference photodetector in the light path separated by said beam splitter.

16. Apparatus according to claim 15, wherein said beam splitter is formed by a thin plate of fused silica glass, said plate being coated by a raster structure of reflecting elements alternating with transmitting elements, said structure having a raster period between 0.1 and 1 millimeters and dividing the incoming light intensity between the light intensity passed to said cell holder and the separated light intensity passed to said reference photodetector by a ratio of 2:1 to 4:1.

17. Apparatus according to claim 15, wherein the photocathode of said reference photodetector has an oblong shape, the main axis of said photocathode being perpendicular to the axis of the lamp image at the monochromator exit, said further collecting lens being formed by a sphero-cylindrical lens structure and imaging the monochromator aperture plane in a direction parallel and said monochromator exit in a direction perpendicular to said main axis.

18. Apparatus according to claim 1, provided with a measuring photodetector in said light path following said sample cell and a collecting lens between said sample cell and said photodetector, the position of said collecting lens being adjustable in directions transverse to said light path.

19. Apparatus according to claim 18, wherein the photocathode of said measuring photodetector has an oblong shape, the main axis of said photocathode being perpendicular to the lamp image in said sample chamber, said collecting lens being formed by a sphero-cylindrical lens structure and imaging the monochromator aperture plane in a direction parallel and the monochromator exit in a direction perpendicular to said main axis.

20. Apparatus according to claim 1, further comprising an optical shutter in front of said monochromator.

21. Apparatus according to claim 15, further comprising an optical shutter in the light path between said beam splitter and said sample cell holder.

22. Apparatus according to claim 3, further comprising a filter holder between said collimating lens and said collecting lens.

23. Apparatus according to claim 18, further comprising a filter holder (HF2) between said sample cell and said measuring photodetector (D2).

24. Apparatus according to claim 15, wherein said beam splitter is placed between said collimating lens and said collecting lens, further comprising a changeable aperture diaphragm in front of said beam splitter, also comprising a changeable diaphragm for the exit slit of said monochromator.

25. Apparatus according to claim 1, further comprising changeable condensor optics with said light source which permit a different imaging of said light source onto said monochromator entrance, so that the light gathering powers of said monochromator and said sample cell can be arbitrarily fully exploited and partially exploited.

26. Apparatus according to claim 25, said condensor optics comprising a lens system imaging said light source onto said entrance, a radiant field diaphragm with said lens system, and a field lens with said entrance, said lens system comprising a first half facing said light source and a second half facing said entrance, further comprising at least two interchangeable lenses for said second half, said interchangeable lenses mounted in replaceable tubes and having a shorter and a larger focal length, respectively, wherein at least said lens of shorter focal length has its own radiant field diaphragm, said diaphragm facing said first half and having a smaller aperture than the aperture of said lens of larger focal length.

27. Apparatus according to claim 25, said condensor optics comprising at least two sets of lenses, said sets having different focal lengths and being mounted on a rotary device at different distances from said light source facing said light source, said rotary device comprising a revolving plate mounting said sets, an axis mounting said plate, a bearing holding said axis, and stops for alternatively switching said sets into said light path.

28. Apparatus according to claim 27, wherein said stops locate the sets on the plate in the respective light path.

29. Apparatus according to claim 1, further comprising a reversing prism for rotating the light bundle in said light path by 90° around its axis.

30. Apparatus according to claim 29, said apparatus further comprising a condensor lens system imaging said light source onto said entrance, said lens system comprising a first half facing said light source and a second half facing said entrance, said light path being collimated between said halves, further comprising an Amici's reversion prism between said halves, said prism being rotatable around its main axis and rotating the image of said light source onto said entrance by 90°.

31. Apparatus according to claim 2, said sample cell having at least one light-collecting window in said second light path, said second light path further comprising with said window at least one light-collecting lens, a filter holder for holding spectral and polarimetric filters, and a photodetector, said light-collecting cell window having an inner surface that equals approximately the dimension of the inner cross section of said sample cell chamber, said light-collecting window and said light-collecting lens forming an optical system of very high light gathering power, said optical system directing the light emitted from said liquid sample through said filters onto said photodetector.

32. Apparatus according to claim 31, said sample cell further comprising two small-angle conical windows in said first light path, said light-collecting window being a wide-angle cone with a spherically ground outside, the conical angles of said windows extending outside.

33. Apparatus according to claim 31, wherein said light-collecting window is a solid light pipe shaped as a small-angle cone, the conical angle extending outside and being at least zero.

34. Apparatus according to claim 31, wherein said sample cell has four optical windows being arranged in one plane at right angles, said plane being perpendicular to the main axis of said cylindrical structure, said second light path extending in a symmetric arrangement at both sides of said cell holder.

35. Apparatus according to claim 31, wherein said sample cell has three optical windows and a spherical second-surface reflector opposite to said light collecting window, said windows and said reflector being arranged in one plane at right angles, said reflector imaging essentially the center of said sample cell onto itself.

36. Apparatus according to claim 31, wherein four sides of said cell chamber and said optical windows are formed by UV-transmitting glass plates, said plates being fused together by black intermediate layers.

37. Apparatus according to claim 36, further comprising convexly shaped lenses at the outside of said glass plates in said secondary light path.

38. Apparatus according to claim 31, wherein said light-collecting lenses are mounted in said cell holder at closest distance to the body of said sample cell, said lenses being mounted in threaded lens holders.

39. Apparatus according to claim 33, wherein said light-collecting lens is a double-lens system (LL3, LL4), said double-lens system being spaced from said light-collecting window (KL3; KL4) at a distance which is approximately equal to the focal length of said double-lens system, said double-lens system being mounted in a threaded lens holder.

40. Apparatus according to claim 2, further comprising a concave mirror in said first light path behind said sample cell, mounted in a removable holder close to said cell holder.

41. Apparatus according to claim 31, wherein said filter holder is mounted on a revolving device, said revolving device providing a revolving angle of at least 90° and comprising a stopping device which provides stops at least at angles which correspond to intensity ratios of vertically to horizontally polarized light of 1:0, 1:2, and 0:1.

42. Apparatus according to claim 41, further comprising a sample cell compartment, said revolving device comprising a hollow bearing with a rotor and a stator, said stator having an undercut collar into which a collar of said rotor fits, said collar of said stator having a gap, said gap passing a lever fixed to said rotor, said rotor and stator being mounted onto the outside of the wall of said sample cell compartment and extending inside through a hole in said wall, said rotor mounting said stopping device and said filter holder inside said compartment, thereby providing a light-tight rotary movement of said holder actuated from the outside by said lever.

43. Apparatus according to claim 1, having a first and a second monochromatic light path, both light paths comprising a light source, a monochromator and means for imaging said light source onto said monochromator and further imaging onto said sample cell chamber, said light paths transmitting said sample cell chamber, said apparatus further comprising at least one measuring photodetector with each of said light paths, and means for directing light from said liquid sample onto said photodetectors.

44. Apparatus according to claim 43, further comprising individual beam splitters and reference photodetectors with both light paths.

45. Apparatus according to claim 43, wherein both light paths have a common light source, common condensor optics, and a common monochromator, said monochromator having one input slit and a first and a second exit slit, said first slit being in fixed position and imaged onto said cell chamber, said second exit slit being in adjustable position with respect to said first exit slit, said second exit being provided with a flexible light pipe the exit of which is imaged onto said cell chamber.

46. Apparatus according to claim 45, said flexible light pipe having a rectangular entrance and a round exit.

47. Apparatus according to claim 43, said sample cell having four windows and said second light path crossing said first light path at right angle.

48. Apparatus according to claim 43, said two light paths being superimposed to each other by dichroic mirrors (TF, TF') and transmitted through said sample cell in parallel directions, said two light paths being again separated by dichroic mirrors (TF, TF') transmitted through spectral filters (F2, F2') and directed onto said individual measuring photodetectors measuring absorption (D2, D2').

49. Apparatus according to claim 48, said two light paths transmitting said sample cell in opposite directions, and said dichroic mirrors serving also as reference beam splitters.

50. Apparatus according to claim 49, said two light paths transmitting said sample cell in equal directions and originating from the same light source via different condensor systems, said second monochromator being formed by a band-pass filter.

51. Apparatus according to claim 43, said two light paths being superimposed to each other by a dichroic mirror and transmitted through said sample cell in parallel directions, said sample cell having at least three windows, one of said light paths being used for measuring absorption, the other one being used for fluorescence excitation, the absorption light being transmitted through a spectral filter and directed onto its photodetector, the fluorescence light emitted at right angle being transmitted through at least one spectral filter and directed onto at least one fluorescence emission photodetector.

52. Apparatus according to claim 51, wherein said two superimposed light paths transmit radiation with respect to said sample cell in opposite directions.

53. Apparatus according to claim 3, modified for fluorescence measurements using the front-on technique, wherein said sample cell has at least one lens-shaped window, said window being placed in said light path and directed towards said monochromator, said collecting lens in front of said cell holder being removed from the said light path and replaced by a light-collecting lens of large aperture, which is inserted into said cell holder close to said sample cell, said light-collecting lens imaging the monochromator aperture plane onto said cell chamber, said light-collecting lens also collecting fluorescence light emitted from said liquid sample and directing it onto a dichroic mirror inserted into said light path, being inclined by 45° to said light path and reflecting said fluorescence light onto one emission photodetector.

54. Apparatus according to claim 1, wherein said cell holder, said sample cell, and optical elements, which optically follow said monochromator, are contained within a light-tight sample cell compartment, said photodetectors being mounted outside in separate housings and connected to said compartment by light-tight flanges.

55. Apparatus according to claim 54, wherein said standard optical elements have holders and supporting devices, said holders and supporting devices mounted with alignment means and released from said compartment by releasing screws.

56. Apparatus according to claim 55, modified for measurements of optical rotation and circular dichroism, wherein said beam splitter is removed and a polarizing optical modulator is inserted into said light path.

57. Apparatus according to claim 1, provided with movable mirrors for quick interchange of said light source and said photodetector.

58. Apparatus according to claim 1, assembled in the block-building technique, wherein the optical functional units are mounted on optical benches on a shock-insolated mounting plate, said mounting plate being electrically conducting and serving as a reference earth to said apparatus.

59. Apparatus according to claim 58, wherein said mounting plate is formed by a plane plate of light metal, mounted on a steel frame, further comprising a thin layer of shock-insulting and damping plastic material between said plate and said frame, and anti-shock suspension elements mounting said steel frame on a supporting frame.

60. Apparatus according to claim 36, wherein said sample cell is designed for use as a temperature-jump cell, said apparatus further comprising a high-voltage pulse source, said sides of said cell chamber forming a diced glass body, said sample cell further comprising an outer body made of insulating material, two electrodes, and two gaskets, said outer body mounting said glass body by said gaskets and having window openings, said light-collecting window being armoured by a plane-convex lens mounted in said outer body, said electrodes mounted onto the bottom and the cover side of said outer body, said bottom and said cover side made as an insulated and a grounded high-voltage connector, respectively, said cover being detachable for filling said cell chamber.

61. Apparatus according to claim 60, the axial ends of said glass body being ground as hollow half-spheres, said electrodes diving into said half-spheres.

62. Apparatus according to claim 1, wherein said sample cell is designed for use as a rapid-mixing cell, said apparatus further comprising a stopped-flow drive unit, said sample cell further comprising: a mixing chamber with at least two entrance ports and one exit port, two inlet tubing connectors and one outlet tubing connector, at least two inlet channels connecting said inlet connectors to said entrance ports and one outlet channel connecting said cell chamber to said outlet connector, said exit port being closely connected to said cell chamber, said channels made in chemically inert material, said apparatus further comprising flexible tubings connecting said connectors to said drive unit, said tubings insulating mechanical shocks caused by operation of said drive unit from the optical components of said apparatus.

63. Apparatus according to claim 62, said sample cell further comprising a metal outer body and an inner body of chemically inert material, said inner body comprising said channels and said cell chamber, further comprising an intermediate channel between said exit port and said cell chamber, said cell chamber formed by a capillary bore longitudinally transversed by said light path and by two UV-transmitting cylindrical windows, said windows having a larger diameter as said bore and mounted at both sides of said bore by threaded mounting rings, said bore, said intermediate channel, and said outlet channel forming a Z-type arrangement.

64. Apparatus according to claim 62, comprising a first light path and means for measurements of transmitted light and a second light path and means for measurements of emitted light, said sample cell having at least three windows and at least one light-collecting window in said second light path, said sample cell further comprising: a cylindrical outer body, a cell chamber formed by a capillary of UV-transmitting material, threaded means mounting said capillary and said mixing chamber, gaskets, and a plane-convex lens with said light-collecting window, the axis of said capillary being centered to the main axis of said body, said mixing chamber contacting one end side of said capillary, said outer body mounting said lens.

65. Apparatus according to claim 64, wherein the outside of said capillary is partly covered by a black light-absorbing glaze, said glaze having openings in reference to said light paths.

66. Apparatus according to claim 64, said body forming diaphragm openings close to said capillary in reference to said light paths.

67. Apparatus according to claim 64, said capillary being formed by four plates of fused silica, said plates being fused together by black intermediate layers, forming a glass body of rectangular cross section.

68. Apparatus according to claim 67, said glass body having in opposite directions thin and thick plates, respectively, further comprising pieces of black filling glass inside, said pieces and said plates forming a Z-shaped flow capillary, the center part of said flow capillary being transversed by said light paths.

69. Apparatus according to claim 67, characterized by a set of glass bodies having identical outer cross sections but various dimensions inside.

70. Apparatus according to claim 64, said mixing chamber facing the lower end side of said capillary, said sample cell having at least two ball valves between said inlet flow channels and said mixing chamber, each of said ball valves comprising: a ball of chemically inert material, a lower valve plate with a conical bore accepting said ball, and an upper valve plate with noses stopping said ball.

71. Apparatus according to claim 64, said inlet flow channels being formed by thin plastic tubings embedded into said outer body in close thermal contact, said channels acting as heat exchangers, each of said channels having at least a volume which equals the volume of said cell chamber.

72. Apparatus according to claim 64, said sample cell further comprising a plunger movable in said capillary and an adjustable stop with said plunger, said outlet flow channel being formed by a thin metal capillary, said metal capillary moving in said stop, said stop being mounted in said outer body.

73. Apparatus according to claim 62, wherein said sample cell is designed for use as a combined rapid-mixing temperature-jump cell, said apparatus further comprising a high-voltage pulse source, said sample cell further comprising an insulating cell body, a grounded upper electrode connected to a metal cover, and an insulated lower electrode connected to a high-voltage connector, said mixing chamber mounted inside said grounded electrode, said grounded electrode comprising a symmetric arrangement of small capillaries leading into said cell chamber, and gaskets, said insulated electrode comprising a draining gap, said gap connected to said outlet channel, said outlet channel passing a section of said grounded electrode.

74. Apparatus according to claim 73, comprising a first and a second light path, said sample cell having at least three windows and at least one light-collecting window in said second light path, said sample cell further comprising: a cell chamber formed by capillary body of UV-transmitting material, threaded means mounting said capillary, and a plane-convex lens with said light-collecting window, the axis of said capillary being centered to the axis of said cell body, said cell body mounting said lens.

75. Apparatus according to claim 74, said sample cell comprising a set of replaceable electrodes with and without said mixing chamber and said small capillaries, and with and without said gap, respectively, for alternative use as a combined rapid-mixing temperature-jump cell and as a pure temperature-jump cell.

76. Apparatus according to claim 36, wherein said sample cell is designed for use as a rapid-mixing cell, said cell forming an integral unit with said stopped-flow drive unit, said integral unit comprising: two drive syringes, a piston actuator actuated via an external tubing by an auxiliary pressurized medium, mechanical coupling means coupling said syringes to said actuator, a mixing chamber facing said cell chamber, said mixing chamber having two entrance ports and one exit port, said exit port connected directly to said cell chamber, a stopping syringe with an adjustable stop provided with a switch, three three-way valves, two inlet and one outlet connector, and internal channels between said valves, said syringes, said mixing chamber, said cell chamber, and said inlet and outlet connectors, said valves alternatively switching said drive syringes to said inlets and said stopping syringe to said outlet, respectively, and to said mixing chamber and to said cell chamber, respectively.

77. Apparatus according to claim 1, the main axis of said cylindrical structure being vertically arranged, wherein said cell holder and sample cells for temperature-jump and field-jump perturbation by a high-voltage DC-pulse have complementary high-voltage connectors at their lower sides, sample cells for supply of hydraulic perturbation energy and for supply of reacting sample solutions have pressure resistant tube connections at their upper sides, and sample cells for supply of optical perturbation energy have at least one auxiliary optical window in the upper half-plane perpendicular to the direction of said light path.

78. Apparatus according to claim 77, said apparatus having a first light path measuring monochromatic absorption and a second light path provided with interchangeable lenses and filters, said apparatus further comprising a flash-light source and means for alternative installation of a photodetector and said flash-light source in said second light path.

79. Apparatus according to claim 77, wherein said cell holder has a system of holes and gaps and a hose connection for supply of purging gas to the windows of said sample cell and to optical elements mounted into the walls of said cell holder, said holes and gaps extending in upward direction and being interconnected by a circular channel.

80. Apparatus according to claim 1, wherein said sample cells have a rotary body and said cell holder has a cylindrical bore, the main axis of said bore being vertical, said cell holder further comprising alternative means for clamping small and large sample cells, the upper part of said bore being threaded for clamping small sample cells by a threaded mounting ring, the upper side of said cell holder having tap holes, said tap holes fitting screws for mounting a flange of large sample cells.

81. Apparatus according to claim 80, wherein said mounting ring comprises a threaded outer ring, an inner ring axially movable in said outer ring, and a spring disk element between said rings, said inner ring pressing on a metal cover of said small sample cells.

82. Apparatus according to claim 80, wherein said cell holder has a flat cone and slot blocks at the circumference of said cylindrical structure, said sample cells have complementary cones and slots at the lower sides of their middle parts, said cones and slot blocks centering and positioning said sample cells.

83. Apparatus according to claim 77, said sample cells having a slim bore in their upper parts, said bore fitting a temperature sensing probe with a very small air gap.

84. Apparatus according to claim 77, wherein said sample cells have rotational lower and middle parts and a box-shaped upper part.

85. Apparatus according to claim 1, further comprising an adapter mating rectangular spectrophotometer cuvettes, said adapter comprising: a cylindrical metal body having identical outer dimensions as said sample cells at least in its middle part, at least one hole of rectangular cross section in said body, and at least two window openings with said hole, the axis of said hole coinciding with the cylindrical axis of said body, said cross section having two sides parallel to said light path, the axis of said openings having an identical position with respect to said outer dimensions as the main optical axis of said sample cells.

86. Apparatus according to claim 85, comprising a first and a second light path, said light source and said monochromator arranged in said first light path, said light paths and the main axis of said cylindrical structure being perpendicular to each other, said adapter comprising at least three window openings, the axis of adjacent openings being perpendicular to each other and to the axis of said hole.

87. Apparatus according to claim 86, said adapter further comprising a plane-convex lens with at least one window.

88. Apparatus according to claim 85, said adapter further comprising a lift mechanism formed with said hole, said lift having at least two stops and accepting two cuvettes in superimposed positions.

89. Apparatus according to claim 85, said metal body comprising an outer part, a revolving inner part with a handle, and a stopping device, said outer part having a cylindrical bore in excentric position with respect to said outer dimensions, said inner part mating said cylindrical bore and comprising at least two rectangular bores in a symmetric arrangement, said stopping device having one stop position with each of said rectangular bores, said device centering the position of said rectangular bore to the main axis of said body.

90. Apparatus according to claim 1, wherein the hollow structure enclosing the selected sample cell is a cylindrical structure.

91. Apparatus according to claim 1, wherein the hollow structure is formed to have a cylindrical opening; and an adapter is provided having an outer surface matching the cylindrical opening and an inner cross-sectional area matching the cross section of the sample cell.

92. Apparatus according to claim 91, wherein the inner cross-sectional area is square.

93. Apparatus according to claim 1, for use with rectangular spectrophotometric cuvettes, said apparatus having a first light path measuring monochromatic absorption and a second light path provided with interchangeable lenses and filters, said apparatus further comprising a flash-light source and means for alternative installation of a photo detector and said flash-light source in said second light path.

94. Apparatus according to claim 93, wherein the hollow structure is formed to have a cylindrical opening; and an adapter is provided having an outer surface matching the cylindrical opening and an inner cross-sectional area matching the cross sectin of the sample cell.

95. Apparatus for investigating fast chemical reactions by optical detection, said reactions being initiated in a chemical system by an external perturbation, said apparatus comprising means for performing said external perturbation, at least one light path, means for supporting a sample cell in said light path, said sample cell forming a cell chamber for holding a liquid sample of said chemical system, at least one photodetector, said light path comprising a light source, a monochromator, means for imaging said light source onto the entrance of said monochromator, and means for imaging the exit of said monochromator onto said sample cell chamber, said apparatus comprising also means for directing light from said liquid sample onto said photodetector, the improvement comprising:

(a) a set of at least two different types of sample cells, each of said types having one different means for application, said means comprising:
  (a.1) two electrodes facing opposite sides of said chamber for temperature-jump perturbation, and means for the application of at least one additional parameter of perturbation comprising:
  (a.2) a pressure autoclave and pressure release means for pressure-jump perturbation,
  (a.3) at least one optical window in an auxiliary light path for flash-light perturbation,
  (a.4) a mixing chamber and flow-channels for rapid mixing, and
  (a.5) two electrodes, a mixing chamber, and flow-channels for combined rapid mixing and temperature-jump perturbation; each of said sample cells having a specific sample volume, and at least two optical windows for application of at least one of the following parameters of observation: optical absorption, fluorescence, scattered light, and parameters of polarization, said sample cells having identical exterior dimensions at least in their middle parts and an identical position of their main optical axis with respect to said exterior dimensions, and at least two further optical windows similar to said two first-mentioned optical windows and capable of passing optical radiation therethrough;

(b) at least two different ones of the following perturbation supply means comprising:
  (b.1) a high-voltage pulse source, and at least one of:
  (b.2) a pressure supply,
  (b.3) a flash-light source, and
  (b.4) a stopped-flow drive system; said flash-light source being located to pass its emitted flash radiation through said two further windows;

(c) a metallic sample cell holder holding said sample cells and holding one selected sample cell operatively inserted into said apparatus, said holder comprising:
  (c.1) a hollow structure enclosing said selected sample cell.
  (c.2) Threaded fixation means for clamping said sample cell therein,
  (c.3) thermostatting channels connected to a liquid thermostatting system,
  (c.4) window openings for passing said light path in a direction perpendicular to the cylindrical axis of said hollow structure,
  (c.5) means for connecting a high-voltage pulse source at one end of said hollow structure, and
  (c.6) said structure including means defining an inner cross section matching the cross section of the selected sample cell and fitting around said cell in close mechanical and thermal contact therewith to place said holder and said sample cell in close mechanical and thermal contact; and (d) a set of changeable optical elements adapting said light path to the optical dimensions of the chamber of said selected sample cell, said elements comprising at least one lens mounted in an adjustable holder and at least one diaphragm modifying the free exit aperture of said monochromator.

96. Apparatus according to claim 95, wherein the hollow structure enclosing said selected sample cell is a cylindrical structure.

97. Apparatus according to claim 95, wherein said apparatus has a first light path measuring monochromatic absorption and a second light path provided with interchangeable lenses and filters, said apparatus further comprising means for alternative installation of a photodetector and said flash-light source in said second light path.

98. Apparatus according to claim 97, wherein said means defining the inner cross section matching the cross section of the sample cell comprises an adapter mating rectangular spectrophotometer cuvettes, said adapter comprising: a cylindrical metal body having identical outer dimensions as said sample cells at least in its middle part, at least one hole of rectangular cross section in said body, and at least two window openings with said hole, the axis of said hole coinciding with the cylindrical axis of said body, said cross section having two sides parallel to said light path, the axis of said openings having an identical position with respect to said outer dimensions as the main optical axis of said sample cells.

99. Apparatus according to claim 95, said set of sample cells further comprising a combined flow temperature-jump cell having one flow inlet bore and one flow outlet bore, two electrodes, and at least two optical windows for optical observation, said combined cell being operatively inserted into said cell holder, said flow inlet being connected to a drive syringe containing a liquid sample of said chemical system, said flow outlet being connected to a stopping syringe, said drive syringe being thermostatted by a first thermostat and said cell holder being thermostatted by a second thermostat, said first thermostat being set to a lower temperature than said second thermostat, said apparatus further comprising two temperature sensing probes measuring the temperature difference between said driving syringe and said sample cell, means controlling the high-voltage pulse energy delivered by said pulse source relative to said temperature difference, means actuating said driving syringe, and means triggering said pulse source by said stopping syringe, whereby the high-voltage pulse is released to said electrodes immediately after said stopping syringe has stopped.

100. Apparatus according to claim 99, wherein said controlling means adjust said high-voltage pulse energy automatically to heat a liquid sample contained in the cell chamber of said combined sample cell by a temperature-jump that equals said temperature difference.

101. Apparatus according to claim 99, wherein said inlet flow bore has its axis centered with respect to the cell chamber of said combined sample cell and produces a flow jet when said driving syringe is actuated, said sample cell further comprising an outlet channel symmetrically arranged around said inlet bore and connected to said outlet bore.

* * * * *